(12) United States Patent
Lippard et al.

(10) Patent No.: US 7,138,520 B2
(45) Date of Patent: Nov. 21, 2006

(54) COORDINATION COMPLEXES HAVING TETHERED THERAPEUTIC AGENTS AND/OR TARGETING MOIETIES, AND METHODS OF MAKING AND USING THE SAME

(75) Inventors: Stephen J. Lippard, Cambridge, MA (US); Carmen M. Barnes, Cambridge, MA (US); Ariel Haskel, East Brunswick, NJ (US); Katie R. Barnes, Melrose, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/755,855

(22) Filed: Jan. 12, 2004

(65) Prior Publication Data

US 2004/0235712 A1    Nov. 25, 2004

Related U.S. Application Data

(60) Provisional application No. 60/505,088, filed on Sep. 23, 2003, provisional application No. 60/439,729, filed on Jan. 13, 2003.

(51) Int. Cl.
C07F 15/00 (2006.01)
C07C 49/15 (2006.01)
(52) U.S. Cl. .......... 540/3; 568/367; 568/368; 568/369; 568/370; 568/371; 568/372; 556/137
(58) Field of Classification Search .......... None
See application file for complete search history.

(56) References Cited

U.S. PATENT DOCUMENTS

| | | | |
|---|---|---|---|
| 4,234,500 A | 11/1980 | Hoeschele et al. | 556/17 |
| 4,271,085 A | 6/1981 | Amundsen et al. | 556/137.6 |
| 4,284,579 A | 8/1981 | Meischen et al. | 556/19 |
| 4,291,027 A | 9/1981 | Hoeschel et al. | 514/76 |
| 4,416,878 A | 11/1983 | Klosa | 514/186 |
| 4,428,943 A | 1/1984 | Meischen et al. | 514/119 |
| 4,457,926 A | 7/1984 | Amundsen et al. | 514/184 |
| 4,462,998 A | 7/1984 | Amundsen et al. | 514/184 |
| 4,505,928 A | 3/1985 | Amundsen et al. | 514/492 |
| 4,560,781 A | 12/1985 | Totani et al. | 556/137 |
| 4,577,018 A | 3/1986 | Hlavka et al. | 544/225 |
| 4,590,001 A | 5/1986 | Stjernholm | 530/394 |
| 4,659,849 A | 4/1987 | Drobnik et al. | 556/137 |
| 4,732,893 A | 3/1988 | Pasini et al. | 514/185 |
| 4,760,155 A | 7/1988 | Heffernan et al. | 556/136 |
| 4,760,156 A | 7/1988 | Heffernan et al. | 556/136 |
| 4,793,986 A | 12/1988 | Serino et al. | 424/1.53 |
| 4,843,161 A | 6/1989 | Lippard et al. | 546/10 |
| RE33,071 E | 9/1989 | Stjernholm | 530/394 |

(Continued)

FOREIGN PATENT DOCUMENTS

EP    1 262 778    4/2002

(Continued)

OTHER PUBLICATIONS

P. Berdagué, et al. J. Chem. Soc. Chem. Commun. (1994), pp. 1589-1590.*

(Continued)

*Primary Examiner*—Cecilia J. Tsang
*Assistant Examiner*—Andrew D. Kosar
(74) *Attorney, Agent, or Firm*—Foley Hoag LLP

(57) ABSTRACT

In part, the present invention is directed to coordination complexes comprising a therapeutic agent. In one aspect, the subject compositions comprise a platinum metal center and a covalently attached therapeutic agent.

23 Claims, 23 Drawing Sheets

BEP1  n = 1
BEP2  n = 2
BEP3  n = 3
BEP4  n = 4
BEP5  n = 5

U.S. PATENT DOCUMENTS

| | | | |
|---|---|---|---|
| 4,870,062 A | 9/1989 | Kurono et al. | 514/63 |
| 4,873,226 A * | 10/1989 | Talroy et al. | 514/46 |
| 4,912,100 A | 3/1990 | Ohno et al. | 514/184 |
| 4,921,963 A | 5/1990 | Skov et al. | 548/101 |
| 4,937,262 A | 6/1990 | Davidson | 514/492 |
| 4,952,676 A | 8/1990 | Heffernan et al. | 530/391.5 |
| 4,956,454 A | 9/1990 | Heffernan et al. | 424/179.1 |
| 4,980,347 A | 12/1990 | Ohno et al. | 514/186 |
| 4,992,553 A | 2/1991 | Von Angerer et al. | 546/12 |
| 5,026,694 A | 6/1991 | Skov et al. | 514/184 |
| 5,028,726 A | 7/1991 | Farrell | 556/137 |
| 5,104,895 A | 4/1992 | Spinelli et al. | 514/492 |
| 5,194,644 A | 3/1993 | Brunner et al. | |
| 5,198,564 A | 3/1993 | Quianhuan | 556/137 |
| 5,225,207 A | 7/1993 | Barreau et al. | 424/649 |
| 5,238,955 A | 8/1993 | Brunner et al. | |
| 5,256,653 A | 10/1993 | Keppler et al. | 514/79 |
| 5,380,897 A | 1/1995 | Hoeschele et al. | 556/137 |
| 5,409,915 A | 4/1995 | Farrell et al. | 514/187 |
| 5,484,612 A | 1/1996 | Brown | 424/649 |
| 5,498,780 A | 3/1996 | Yokoi et al. | 514/492 |
| 5,519,155 A | 5/1996 | Barnard et al. | 556/137 |
| 5,547,982 A | 8/1996 | Abrams et al. | 514/492 |
| 5,561,042 A | 10/1996 | Weis et al. | 435/6 |
| 5,624,919 A | 4/1997 | Farrell | 514/184 |
| 5,633,243 A | 5/1997 | Sugimura et al. | 514/184 |
| 5,714,327 A | 2/1998 | Houthoff et al. | 435/6 |
| 5,744,497 A | 4/1998 | Valsecchi et al. | 514/492 |
| 5,770,591 A | 6/1998 | Farrell | 514/187 |
| 5,902,826 A | 5/1999 | Mogi et al. | 514/492 |
| 5,985,566 A | 11/1999 | Houthoff et al. | 435/6 |
| 6,011,166 A | 1/2000 | Valsecchi et al. | 556/137 |
| 6,022,892 A | 2/2000 | Farrell et al. | 514/492 |
| 6,060,616 A | 5/2000 | Farrell et al. | 556/137 |
| 6,113,934 A | 9/2000 | Farrell et al. | 424/405 |
| 6,130,245 A | 10/2000 | Shaw | 514/492 |
| 6,133,038 A | 10/2000 | Houthoff et al. | 436/84 |
| 6,248,531 B1 | 6/2001 | Houthoff et al. | 435/6 |
| 6,313,333 B1 | 11/2001 | Da Re et al. | 556/137 |
| 6,333,422 B1 | 12/2001 | Sohn et al. | 556/17 |
| 6,340,770 B1 * | 1/2002 | Kwon et al. | 556/137 |
| 6,384,081 B1 * | 5/2002 | Berman | 514/621 |
| 6,469,066 B1 * | 10/2002 | Dosch et al. | 514/557 |
| 6,605,734 B1 | 8/2003 | Roy et al. | 556/9 |
| 6,692,734 B1 | 2/2004 | Stewart et al. | 424/78.27 |
| 6,806,289 B1 * | 10/2004 | Lippard et al. | 514/492 |
| 6,825,330 B1 | 11/2004 | Braman et al. | 536/23.1 |
| 2004/0006051 A1 | 1/2004 | Berube | 514/169 |

FOREIGN PATENT DOCUMENTS

| | | |
|---|---|---|
| EP | 0 169 645 | 1/2006 |
| WO | WO 96/35696 | 11/1996 |
| WO | WO 00/27847 | 5/2000 |
| WO | WO 03/017993 | 3/2003 |

OTHER PUBLICATIONS

J. Altman, et al. Inorg. Chem. (1991) 30, pp. 4085-4088.*

Arap, Wadih, et al., "Cancer Treatment by Targeted Drug Delivery to Tumor Vasculature in a Mouse Model," Science, vol. 279, Jan. 16, 1998, pp. 377-380.

Brown, Steven J., et al., "Ixrl, a Yeast Protein That Binds to Platinated DNA and Confers Sensitivity to Cisplatin," Science, vol. 261, Jul. 30, 1993, pp. 603-605.

Chen, Lie, et al., "Reduction of the anti-cancer drug analogue cis, trans, cis-[PtCl$_2$(OCOCH$_3$)$_2$(NH$_3$)$_2$] by L-cysteine and L-methionine and its crystal structure," J. Chem. Soc., Dalton Trans., 1999, pp. 1209-1212.

Cohen, Seth M., et al., "Cisplatin: From DNA Damage to Cancer Chemotherapy," Progress in Nucleic Acid Research and Molecular Biology, vol. 67, 2001, pp. 93-130.

Dhara, S.C., A Rapid Method for the Synthesis of cis-[Pt(NH$_3$)$_2$Cl$_2$], Indian Journal of Chemistry, vol. 8, No. 2, Feb. 1970, pp. 193-194.

Ellerby, H. Michael, et al., "Anti-cancer activity of targeted pro-apoptotic peptides," Nature Medicine, vol. 5, No. 9, Sep. 1999, pp. 1032-1038.

Folkman, Judah, "What Is the Evidence That Tumors Are Angiogenesis Dependent?", Journal of the National Cancer Institute, vol. 82, No. 1, Jan. 3, 1990, pp. 4-6.

Folkman, Judah, Alternative Strategies for Biologic Therapy, Chapter 30, Antiangiogenesis, pp. 743-753.

Folkman, Judah, et al., "Minireview, Angiogenesis," The Journal of Biological Chemistry, vol. 267, No. 16, Issue of Jun. 5, 1992, pp. 1031-1034.

Giandomenico, Christen M., et al., Carboxylation of Kinetically Inert Platinum (IV) Hydroxy Complexes. An Entrée into Orally Active Platinum(IV) Antitumor Agents, Inorganic Chemistry, vol. 34, No. 5, 1995, pp. 1015-1021.

Hambley, T.W., et al., "Modifying the Properties of Platinum (IV) Complexes in Order to Increase Biological Effectiveness," Journal of Inorganic Biochemistry, 77 (1999), pp. 3-12.

Hammes, Hans-Peter, et al., "Subcutaneous Injection of a Cyclic Peptide Antagonist of Vitronectin Receptor-Type Integrins Inhibits Retinal Neovascularization," Nature Medicine, vol. 2, No. 5, May 1996, pp. 529-533.

Hart, Stephen L, et al., "Cell Binding and Internalization by Filamentous Phage Displaying a Cyclic Arg-Gly-Asp-containing Peptide," The Journal of Biological Chemistry, vol. 269, No. 17, Issue of Apr. 29, 1994, pp. 12468-12474.

Healy, Judith M., et al., "Peptide Ligands for Integrin $\alpha\beta_3$ Selected from Random Phage Display Libraries," Biochemistry, vol. 34, No. 12, 1995, pp. 3948-3955.

Houston, Parul, et al., "Homing markers for atherosclerosis: applications for drug delivery, gene delivery and vascular imaging," Federation of European Biochemical Societies, 2001, pp. 73-77.

Huang, Juch-Chin, et al., "HMG-domain proteins specifically inhibit the repair of the major DNA adduct of the anticancer drug cisplatin by human excision nuclease," Proc. Natl. Acad. Sci. USA, vol. 91, Oct. 1994, pp. 10394-10398.

Jamieson, Elizabeth R., et al., "Structure, Recognition, and Processing of Cisplatin—DNA Adducts," Chemical Reviews, 1999, pp. 2467-2498.

Kartalou, Maria, et al., "Recognition of cisplatin adducts by cellular proteins," Mutation Research 478 (2001), pp. 1-21.

Koivunen, Erkki, et al., "Isolation of a Highly Specific Ligand for the $\alpha_3\beta_1$ Integrin from a Phage Display Library," The Journal of Cell Biology, vol. 124, No. 5, Feb. 1994, pp. 373-380.

Koivunen, Erkki, et al., "Selection of Peptides Binding to the $\alpha_3\beta_1$ Integrin from Phage Display Library," The Journal of Biological Chemistry, vol. 268, No. 27, Issue of Sep. 25, 1993, pp. 20205-20210.

Koivunen, Erkki, et al., "Phage Libraries Displaying Cyclic Peptides with Different Ring Sizes: Ligand Specificities of the RGD-Directed Integrins," Bio/Technology, vol. 13, Mar. 1995, pp. 265-270.

Lee, Keng-Boon, et al., "Transcription-coupled and DNA damage-dependent ubiquitination of RNA polymerase II in vitro," PNAS, vol. 99, No. 7, Apr. 2, 2002, pp. 4239-4244.

Lee, Young-A, et al., "Synthesis and Oral Antitumor Activity of Tetrakis (carboxylato) platinum (IV) Complexes," J. Med. Chem., vol. 43, No. 7, 2000, pp. 1409-1412.

Lemma, Kelemu, et al., "Kinetics and Mechanism for Reduction of the Anticancer Prodrug trans,trans,trans-[PtCl$_2$(OH)$_2$(c-C$_6$H$_{11}$NH$_2$)(NH$_3$)] (JM335) by Thiols," Inorganic Chemistry, vol. 39, No. 8, 2000, pp. 1728-1734.

Lemma, Kelemu, et al., "Kinetics and Mechanism for reduction of anticancer-active tetrachloroam(m)ine platinum(IV) compounds by glutathione," Journal of Biological Inorganic Chemistry, vol. 5, No. 3, Jun. 2000, pp. 300-306.

Lemma, Kelemu, et al., "Kinetics and mechanism for reduction of halo-and haloam(m)ine platinum(IV) complexes by L-ascorbate," Inorganica Chimica Acta, 331,2002, pp. 98-108.

Maclusky, Neil J., et al., "Actions of an Estradiol-17-Fatty Acid Ester in Estrogen Target Tissues of the Rat: Comparison with Other C-17 Metabolites and a Pharmacological C-17 Ester," Endocrinology, vol. 124, No. 1, 1989, pp. 318-324.

Orme, Mark W., et al., "Synthesis of β-Estradiol-3-Benzoate-17-(Succinyl-12A-Tetracycline): A Potential Bone-Seeking Estrogen," *Bioorganic & Medicinal Chemistry Letters,* vol. 4, No. 11, 1994, pp. 1375-1380.

Pasqualini, Renata, et al., "Organ targeting in vivo using phage display peptide libraries," Nature, vol. 380, Mar. 28, 1996, pp. 364-366.

Qing, He, et al., "Sterioid hormones induce HMGI overexpression and sensitize breast cancer cells to cisplatin and carboplatin," PNAS, vol. 97, No. 11, May 23, 2000, pp. 5768-5772.

Rajotte, Daniel, et al., "Molecular Heterogeneity of the Vascular Endothelium Revealed by In Vivo Phage Display," J. Clin. Invest., vol. 102, No. 2, Jul. 1998, pp. 430-437.

Reedijk, Jan, "The mechanism of action of platinum anti-tumor drugs," *Pure & Appl. Chem.,* vol. 59, No. 2, 1987, pp. 181-192.

Rosenberg, Barnett, et al., "Inhibiton of Cell Division in *Escherichia coli* by Electrolysis Products from a Platinum Electrode," Nature, vol. 205, Feb. 13, 1965, pp. 698-698.

Ruoslahti, Erkki, "Specialization of Tumour Vasculature," Nature Reviews, vol. 2, Feb. 2002, pp. 83-90.

Shi, Tiesheng, et al., "Reduction of *trans*-dichloro- and *trans*-dibromo-tetracyano-platinate (IV) by L-methionine," *J. Chem.Soc., Dalton Trans.,* 1997, pp. 2073-2077.

Shi, Tiesheng, et al., "Kinetics and Methanism for Reduction of *trans*-Dichlorotetracyanoplatinate(IV) by Thioglycolic Acid, L-Cysteine, DL-Penicillamine, and Glutathione in Aqueous Solution," *Inorganic Chemistry,* vol. 35, No. 12, 1996, pp. 3498-3503.

Takahara, Patricia M., et al., "Crystal Structure of the Anticancer Drug Cisplatin Bound to Duplex DNA," *J. Am. Chem. Soc.,* vol. 118, No. 49, 1996, pp. 12309-12321.

Treiber, Daniel K., et al., Cisplatin—DNA adducts are molecular decoys for the ribosomal RNA transcription factor hUBF (human upstream binding factor), *Proc. Natl. Acad. Sci.,* vol. 91, Jun. 1994, pp. 5672-5676.

Trepel, M., et al., "Exploring vascular heterogeneity for gene therapy targeting," *Gene Therapy,* 2000.

Trimmer, Elizabeth E., et al., "Cisplatin," Essays in Biochemistry, vol. 34, 1999, pp. 191-211.

Wong, Ernest, et al., "Current Status of Platinum-based Antitumor Drugs," *Chem. Rev.* vol. 99, No. 9, 1999, pp. 2451-2466.

Ziegler, Christopher J., et al., "High-throughput synthesis and screenign of platinum drug candidates," *J. Biol. Inorg. Chem.,* 2000, pp. 774-783.

* cited by examiner

BEP1 n = 1
BEP2 n = 2
BEP3 n = 3
BEP4 n = 4
BEP5 n = 5

HMGB1 Control

Estrogen

BEP

1

Synthesis of BEP, an Estrogen-Tethered Cisplatin Precursor

MCF-7 cells
no hormone

BEP, 2h

A

B

COORDINATION COMPLEXES HAVING TETHERED THERAPEUTIC AGENTS AND/OR TARGETING MOIETIES, AND METHODS OF MAKING AND USING THE SAME

RELATED APPLICATION INFORMATION

This application claims the benefit of priority under 35 U.S.C. section 119(e) to U.S. Provisional Patent Applications 60/439,729, filed Jan. 13, 2003; and 60/505,088, filed Sep. 23, 2003, both of which are hereby incorporated in their entirety.

GOVERNMENT SUPPORT

The subject invention was made in part with support from the U.S. Government under a grant from the National Cancer Institute. Accordingly, the U.S. Government has certain rights in this invention.

INTRODUCTION

Advances in understanding the roles of metals in cell regulation, and the ability to characterize proteins and model metal/ligand interactions in drug design have lead to the development of metal coordination complexes as useful therapeutic agents. The success of cisplatin and its congeners is but one example of such a therapeutically effective coordination complex. The ability to synthesize sophisticated metal complexes and advances in controlling the reactivity of metals in vitro and in vivo have lead to an increasing number of effective therapeutic coordination complexes tailored to provide clinically useful pharmacokinetic properties.

One example in which coordination complexes have found application as therapeutic agents is cancer. Cancer arises in many instances in which a normal cell undergoes neoplastic transformation and becomes a malignant cell. Transformed (malignant) cells escape normal physiologic controls specifying cell phenotype and restraining cell proliferation. Transformed cells in an individual's body thus proliferate, forming a tumor (also referred to as a neoplasm). When a tumor is found, the clinical objective is to destroy malignant cells selectively while mitigating any harm caused to normal cells in the individual undergoing treatment.

Despite decades of intense research, cancer continues to be one of the most devastating and yet unsolved diseases with no definitive cure. Tumor cells are characterized by their fast and indefinitely proliferation eventually metastasizing throughout the body. Tumors cannot grow without blood supply and to do so they promote the formation of new blood vessels. This fundamental process is known as angiogenesis. Angiogenesis is also initiated by local hypoxia (1% $O_2$), causing the up-regulation of the gene hif1α (hypoxy inducible factor 1 α) which encodes angiogenic proteins. Angiogenesis is activated for a brief period of time during reproduction, development and wound repair and then completely inhibited. The right balance between angiogenic molecules (i.e. growth factors) and angiogenic inhibitors allows the regulation of the process. On the other hand, it is the wrong balance between angiogenic molecules and inhibitors that drives many diseases. For example, tumors continuously release angiogenic molecules in order to activate the formation of new capillary blood vessels which ultimately connect the tumor to the vascular system, thus allowing the tumor to grow indefinitely and providing a gateway for tumor cells to enter the vasculature and to metastasize to other organs.

Chemotherapy is often based on the use of drugs that are selectively toxic (cytotoxic) to cancer cells. Several general classes of chemotherapeutic drugs have been developed. A first class, antimetabolite drugs, includes drugs that interfere with nucleic acid synthesis, protein synthesis, and other vital metabolic processes. Another class, genotoxic drugs, inflicts damage on cellular nucleic acids, including DNA. Two widely used genotoxic anticancer drugs that have been shown to damage cellular DNA by producing crosslinks therein are cisplatin [cis-diamminedichloroplatinum(II)] and carboplatin [diammine(1,1-cyclobutanedicarboxylato)-platinum(II)]. Cisplatin and carboplatin currently are used in the treatment of selected, diverse neoplasms of epithelial and mesenchymal origin, including carcinomas and sarcomas of the respiratory, gastrointestinal and reproductive tracts, of the central nervous system, and of squamous origin in the head and neck. Cisplatin currently is preferred for the management of testicular carcinoma and in many instances produces a lasting remission. In cisplatin chemistry, one of the significant areas of research has involved the clinical difference, as exemplified in a variety of in vitro assays, indicating that trans-diamminedichloroplatinum(II) (trans-DDP) a regioisomer of cisplatin, is not an effective chemotherapeutic.

The repair of damage to cellular DNA is an important biological process carried out by a cell's enzymatic DNA repair machinery. Unrepaired lesions in a cell's genome may impede DNA replication, impair the replication fidelity of newly synthesized DNA or hinder the expression of genes needed for cell survival. Thus, genotoxic drugs generally are considered more toxic to actively dividing cells that engage in DNA synthesis than to quiescent, nondividing cells. Indeed, cells carrying a genetic defect in one or more elements of the enzymatic DNA repair machinery have been observed to be extremely sensitive to cisplatin. Normal cells of many body tissues, however, are quiescent and commit infrequently to re-enter the cell cycle and divide. Greater time between rounds of cell division generally is afforded for the repair of DNA damage in normal cells inflected by chemotherapeutic genotoxins. As a result, some selectivity is achieved for the killing of cancer cells. Many treatment regimes reflect attempts to improve selectivity for cancer cells by co-administering chemotherapeutic drugs belonging to two or more of these general classes.

In some tissues, however, normal cells divide continuously. Thus, skin, hair follicles, buccal mucosa and other tissues of the gut lining, sperm and blood-forming tissues of the bone marrow remain vulnerable to the action of genotoxic drugs, including cisplatin. These and other classes of chemotherapeutic drugs can also cause severe adverse side effects in drug-sensitive organs, such as the liver and kidneys. These and other adverse side effects seriously constrain the dosage levels and lengths of treatment regimens that can be prescribed for individuals in need of cancer chemotherapy. Such constraints can prejudice the effectiveness of clinical treatment. For example, the drug or drug combination administered must contact and affect cancer cells at times appropriate to impair cell survival. Genotoxic drugs are most effective for killing cancer cells that are actively dividing when chemotherapeutic treatment is applied. Conversely, such drugs are relatively ineffective for the treatment of slow growing tumors. Carcinoma cells of the breast, lung and colorectal tissues, for example, typically double as slowly as once every 100 days. Such slowly growing tumors present difficult chemotherapeutic targets.

Moreover, cancer cells may acquire resistance to genotoxic drugs through diminished uptake or other changes in drug metabolism, such as those that occur upon drug-induced gene amplification or expression of a cellular gene for multiple drug resistance (MDR). Resistance to genotoxic drugs may also be acquired by activation or enhanced expression of enzymes in the cancer cell's enzymatic DNA repair machinery. Therapies that employ combinations of drugs, or drugs and radiation, attempt to overcome these limitations. The pharmacokinetic profile of each chemotherapeutic drug in such a combinatorial regime, however, will in all likelihood differ. In particular, permeability of neoplastic tissue for each drug may be different. Thus, it may be difficult to achieve genotoxically effective concentrations of multiple chemotherapeutic drugs in target tissues.

Endothelial cells line capillary blood vessels, and contain all the genetic information needed to repair and form new capillary networks. They also control the passage of materials into and out of the blood stream.

Endothelial cells lining blood vessels express organ-specific markers and this heterogeneity at the molecular level of the vascular system can potentially be used for the specific binding of chemotherapeutic agents. Endothelial cells in angiogenic vessels express their own set of integrin and aminopeptidase-N cell-surface receptors, which differ from the non-angiogenic set of markers. Integrins, which are heterodimers composed of α and β subunits (e.g. $\alpha_v\beta_3$, $\alpha_v\beta_5$) are known to mediate cell adhesion and are involved in cell migration. Aminopeptidase-N (APN) is a 140-kDa protein, which has been associated with cell migration and tumor invasion. These molecular addresses are known to recognize and internalize short amino acid sequences into the cells. During the last decade, phage display libraries have been used to select in vivo for peptides recognized by the vascular endothelium of normal tissues and malignant tumors. Recovery of the phage form the tumors led to the identification of two peptide sequences CNGRCVSG-CAGRC (SEQ ID NO: 1) and CDCRGDCFC (SEQ ID NO: 2). The three-amino acids peptide sequences Asn—Gly—Arg (NGR) and Arg—Gly—Asp (RGD), either containing cysteins or not, were found to interact specifically with integrins, APN receptors and additionally internalized into tumor cells. Phage containing these peptides homed to human breast carcinoma, human Kaposi's sarcoma and mouse melanoma. Additionally these peptide sequences were successfully used as a vehicle to selectively delivering in vivo and in vitro a pro-apoptotic peptide and the anticancer drug doxorubicin.

In part, the present invention is directed towards coordination complexes that contain a covalently attached therapeutic agent. In part, the present invention is directed towards coordination complexes that contain a covalently attached targeting moiety. In a further part, the coordination complexes of the present invention may contain both a covalently attached therapeutic agent and a covalently attached targeting moiety.

SUMMARY OF INVENTION

In part, the present invention is directed to coordination complexes that contain a therapeutic agent, and methods of making and using the same. After release of the therapeutic agent from the coordination complex, both the resulting therapeutic agent and the coordination complex formed after such release are intended to be therapeutically active. The therapeutic agent is covalently attached to the metal ion, either bonded directly or by the use of a tether. In certain embodiments, release of the therapeutic agent from the metal ion of the subject coordination complex is precipitated by a redox change at the metal ion to which the therapeutic agent is covalently attached.

In part, the present invention is directed to coordination complexes that contain a targeting moiety, and methods of making and using the same. After release of the targeting moiety from the coordination complex, the resulting coordination complex formed after such release is intended to be therapeutically active. The targeting moiety is covalently attached to the metal ion, either bonded directly or by the use of a tether. In certain embodiments, release of the targeting moiety from the metal ion of the subject coordination complex is precipitated by a redox change at the metal ion to which the targeting moiety is covalently attached.

In part, the present invention is directed to coordination complexes that contain a therapeutic agent and a targeting moiety, and methods of making and using the same. After release of the therapeutic agent from the coordination complex, both the resulting therapeutic agent and the coordination complex formed after such release are intended to be therapeutically active. The therapeutic agent and targeting moiety are covalently attached to the metal ion, either bonded directly or by the use of a tether. In certain embodiments, release of the therapeutic agent and targeting moiety from the metal ion of the subject coordination complex is precipitated by a redox change at the metal ion to which the therapeutic agent and targeting moiety are covalently attached.

The present invention contemplates the use of different metal ions, different therapeutic agents, and different targeting moieties in the inventive coordination complexes. In any embodiment, a subject coordination complex may contain one or more metal ions, one or more therapeutic agents, and one or more targeting moieties.

The subject compositions, and methods of making and using the same, may achieve a number of desirable results and features, one or more of which (if any) may be present in any particular embodiment of the present invention: (i) the subject coordination complexes are capable of delivering two therapeutically effective agents, the coordination complex itself and the released therapeutic agent; (ii) the timing of release of the therapeutic agent and/or the targeting moiety from the coordination complex may be controlled by judicious choice of the ligands of the metal ion of the coordination complex; (iii) the therapeutic agent and the coordination complex formed upon release of the therapeutic agent are simultaneously delivered; (iv) the release of the therapeutic agent from the coordination complex is precipitated by a redox change at the metal ion; (v) the therapeutic agent or targeting moiety is attached directly to the metal ion or through a tether; (vi) the released therapeutic agent causes sensitization of the target cells to the coordination complex and vice-versa; and (vii) targeted delivery of the coordination complex.

In one embodiment, the present invention relates to a compound comprising: (a) a platinum metal center, (b) two cis labile ligands bonded to the platinum metal center, and (c) one or more therapeutic agents and/or targeting moieties covalently attached to the platinum metal center, wherein the therapeutic agent is not covalently attached to the platinum metal center through the cis labile ligands. In a further embodiment, the two cis labile ligands are halides. In a further embodiment, the halides are chlorides. In a further embodiment, the therapeutic agent is a steroid. In a further embodiment, the steroid is estrogen. In one embodiment, the targeting moiety is a peptide. In a further embodiment, the peptide comprises asparagine, glycine, and arginine. In a further embodiment, the peptide comprises alanine, glycine, and arginine. In a further embodiment, the peptide comprises arginine, glycine, and aspartic acid. In a further embodiment, the peptide comprises alanine and arginine. In one embodiment, the targeting moiety comprises biotin.

In one embodiment, the therapeutic agent is covalently attached to the metal center through a tether. In another embodiment, the therapeutic agent is covalently attached to the metal center by coordinate bond. In a further embodiment, the therapeutic agent is a steroid. In a further embodiment, the steroid is estrogen. In one embodiment, the targeting moiety is covalently attached to the metal center through a tether. In another embodiment, the targeting moiety is covalently attached to the metal center by coordinate bond. In a further embodiment, the targeting moiety is a peptide. In a further embodiment, the targeting moiety comprises biotin.

In still other embodiments, the subject compositions have the structures described in the claims below, all of which claims are hereby incorporated by reference in their entirety into this Summary.

In a further embodiment, the platinum metal center comprises two cis non-labile ligands bonded to it, and wherein the therapeutic agent is not covalently attached to the platinum metal center through the cis non-labile ligands.

In a further embodiment, the compound has the following formula:

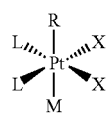

wherein:
  X, independently for each occurrence, represents a labile covalently bonded ligand, or both of X taken together are bridged and represent a bidentate ligand;
  L, independently for each occurrence, represents a ligand bonded to the platinum metal center through a covalent bond, or both of L taken together are bridged and represent a bidentate ligand;
  M represents a therapeutic agent, a targeting moiety, or a labile covalently bonded ligand; and
  R represents a therapeutic agent or a targeting moiety.

In a further embodiment, the present invention relates to a compound of formula I and the attendant definitions wherein M is a non-labile covalently bonded ligand and not a therapeutic agent or targeting moiety.

In a further embodiment, the present invention relates to a compound of formula I and the attendant definitions wherein the compound is charged.

In a further embodiment, the present invention relates to a compound of formula I and the attendant definitions wherein M is a therapeutic agent and is the same as R.

In a further embodiment, the present invention relates to a compound of formula I and the attendant definitions wherein M is a targeting moiety and is the same as R.

In a further embodiment, the present invention relates to a compound of formula I and the attendant definitions wherein M is a therapeutic agent and is different than R.

In a further embodiment, the present invention relates to a compound of formula I and the attendant definitions wherein M is a targeting moiety and is different than R.

In a further embodiment, the present invention relates to a compound of formula I and the attendant definitions wherein X, independently for each occurrence, is selected from the group consisting of halide, —O-alkyl, —O-aryl, alkyl, and aryl.

In a further embodiment, the present invention relates to a compound of formula I and the attendant definitions wherein both of X are Cl.

In a further embodiment, the present invention relates to a compound of formula I and the attendant definitions wherein at least one L is $NH_3$.

In a further embodiment, the present invention relates to a compound of formula I and the attendant definitions wherein both of X taken together represent

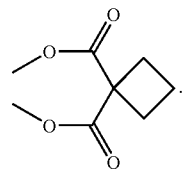

In a further embodiment, the present invention relates to a compound of formula I and the attendant definitions wherein both of X taken together represent

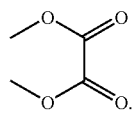

In a further embodiment, the present invention relates to a compound of formula I and the attendant definitions wherein L is cyclohexyamine.

In a further embodiment, the present invention relates to a compound of formula I and the attendant definitions wherein both of L taken together represent

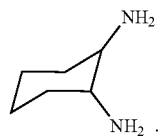

In a further embodiment, the present invention relates to a compound of formula I and the attendant definitions wherein R is covalently attached to the platinum metal center through a tether.

In a further embodiment, the present invention relates to a compound of formula I and the attendant definitions wherein R is a tethered steroid.

In a further embodiment, the present invention relates to a compound of formula I and the attendant definitions wherein the steroid is estrogen.

In a further embodiment, the present invention relates to a compound of formula I and the attendant definitions wherein the steroid is progesterone.

In a further embodiment, the present invention relates to a compound of formula I and the attendant definitions wherein R is a tethered peptide.

In a further embodiment, the present invention relates to a compound of formula I and the attendant definitions wherein R comprises asparagine, glycine, and arginine.

In a further embodiment, the present invention relates to a compound of formula I and the attendant definitions wherein R comprises a biotin moiety.

In a further embodiment, the present invention relates to a compound of formula I and the attendant definitions wherein the tether comprises an amide moiety.

In a further embodiment, the present invention relates to a compound of formula I and the attendant definitions wherein both of X are Cl, both of L are $NH_3$, R is a tethered steroid wherein the steroid is estrogen, and the tether comprises an amide moiety.

In a further embodiment, the present invention relates to a compound of formula I and the attendant definitions wherein both of X are Cl, both of L are $NH_3$, R is a tethered peptide comprising asparagine, glycine, and arginine, and the tether comprises an amide moiety.

In a further embodiment, the present invention relates to a compound of formula I and the attendant definitions wherein both of X are Cl, both of L are $NH_3$, R comprises a tethered biotin moiety, and the tether comprises an amide moiety.

In a further embodiment, the present invention relates to a compound of formula I and the attendant definitions wherein both of X are Cl, both of L are $NH_3$, both R and M are tethered steroids wherein the steroids are estrogen, and the tethers comprise an amide moiety.

In a further embodiment, the present invention relates to a compound of formula I and the attendant definitions wherein both of X are Cl, both of L are $NH_3$, both R and M are tethered peptides comprising asparagine, glycine, and arginine, and the tethers comprise an amide moiety.

In a further embodiment, the present invention relates to a compound of formula I and the attendant definitions wherein both of X are Cl, both of L are $NH_3$, both R and M comprise a tethered biotin moiety, and the tethers comprise an amide moiety.

In a further embodiment, the present invention relates to a compound of formula I and the attendant definitions wherein both of X are Cl, both of L are $NH_3$, both R and M are tethered steroids wherein one steroid is estrogen and the other steroid is not, and the tethers comprise an amide moiety.

In a further embodiment, the present invention relates to a compound of formula I and the attendant definitions wherein both of X are Cl, both of L are $NH_3$, R is a tethered peptide comprising asparagine, glycine, and arginine, M is a non-labile covalently bonded ligand, and the tether comprises an amide moiety.

In a further embodiment, the present invention relates to a compound of formula I and the attendant definitions wherein both of X are Cl, both of L are $NH_3$, R comprises a tethered biotin moiety, M is a non-labile covalently bonded ligand, and the tether comprises an amide moiety.

In a further embodiment, the present invention relates to a compound of formula I and the attendant definitions wherein both of X taken together represent

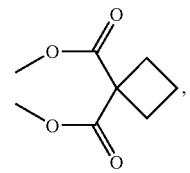

both of L are $NH_3$, both R and M are tethered steroids wherein the steroids are estrogen, and the tethers comprise an amide moiety.

In a further embodiment, the present invention relates to a compound of formula I and the attendant definitions wherein both of X taken together represent

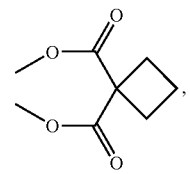

both of L are $NH_3$, both R and M are tethered peptides comprising asparagine, glycine, and arginine, and the tethers comprise an amide moiety.

In a further embodiment, the present invention relates to a compound of formula I and the attendant definitions wherein both of X taken together represent

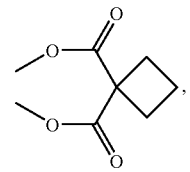

both of L are $NH_3$, both R and M comprise a tethered biotin moiety, and the tethers comprise an amide moiety.

In a further embodiment, the present invention relates to a compound of formula I and the attendant definitions wherein both of X taken together represent

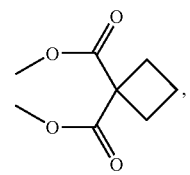

both of L are $NH_3$, and both R and M are tethered steroids, wherein one steroid is estrogen and the other is not, and the tethers comprise an amide moiety.

In a further embodiment, the present invention relates to a compound of formula I and the attendant definitions wherein both of X taken together represent

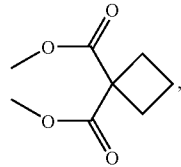

both of L are NH$_3$, R is a peptide comprising asparagine, glycine, and arginine, M is a non-labile covalently bonded ligand, and the tether comprises an amide moiety.

In a further embodiment, the present invention relates to a compound of formula I and the attendant definitions wherein both of X taken together represent

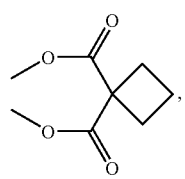

both of L are NH$_3$, R comprises a tethered biotin moiety, M is a non-labile covalently bonded ligand, and the tether comprises an amide moiety.

In a further embodiment, the present invention relates to a compound of formula I and the attendant definitions wherein both of X taken together represent

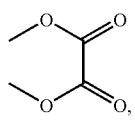

both of L are NH$_3$, and both R and M are tethered steroids wherein the steroids are estrogen, and the tethers comprise an amide moiety.

In a further embodiment, the present invention relates to a compound of formula I and the attendant definitions wherein both of X taken together represent

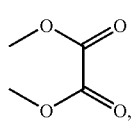

both of L are NH$_3$, both R and M are tethered peptides comprising asparagine, glycine, and arginine, and the tethers comprise an amide moiety.

In a further embodiment, the present invention relates to a compound of formula I and the attendant definitions wherein both of X taken together represent

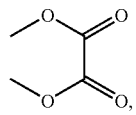

both of L are NH$_3$, both R and M comprise a tethered biotin moiety, and the tethers comprise an amide moiety.

In a further embodiment, the present invention relates to a compound of formula I and the attendant definitions wherein both of X taken together represent

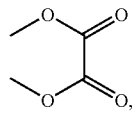

both of L are NH$_3$, and both R and M are tethered steroids wherein one steroid is estrogen and the other steroid is not, and the tethers comprise an amide moiety.

In a further embodiment, the present invention relates to a compound of formula I and the attendant definitions wherein both of X taken together represent

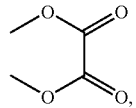

both of L are NH$_3$, R is a peptide comprising asparagine, glycine, and arginine, M is a non-labile covalently bonded ligand, and the tether comprises an amide moiety.

In a further embodiment, the present invention relates to a compound of formula I and the attendant definitions wherein both of X taken together represent

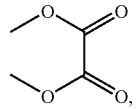

both of L are NH$_3$, R comprises a tethered biotin moiety, M is a non-labile covalently bonded ligand, and the tether comprises an amide moiety.

In a further embodiment, the present invention relates to a compound of formula I and the attendant definitions wherein both of X are Cl, both of L taken together represent

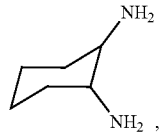

and both R and M are tethered steroids wherein the steroids are estrogen, and the tethers comprise an amide moiety.

In a further embodiment, the present invention relates to a compound of formula I and the attendant definitions wherein both of X are Cl, both of L taken together represent

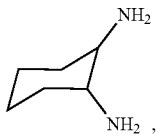

and both R and M are tethered peptides comprising asparagine, glycine, and arginine, and the tethers comprise an amide moiety.

In a further embodiment, the present invention relates to a compound of formula I and the attendant definitions wherein both of X are Cl, both of L taken together represent

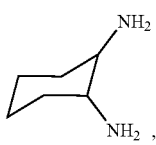

and both R and M comprise tethered biotin moieties, and the tethers comprise an amide moiety.

In a further embodiment, the present invention relates to a compound of formula I and the attendant definitions wherein both of X are Cl, both of L taken together represent

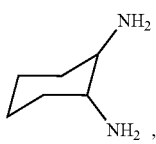

and both R and M are tethered steroids wherein one steroid is estrogen and the other steroid is not, and the tethers comprise an amide moiety.

In a further embodiment, the present invention relates to a compound of formula I and the attendant definitions wherein both of X are Cl, both of L taken together represent

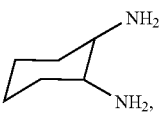

R is a tethered peptide comprising asparagine, glycine, and arginine, M is a non-labile covalently bonded ligand, and the tether comprises an amide moiety.

In a further embodiment, the present invention relates to a compound of formula I and the attendant definitions wherein both of X are Cl, both of L taken together represent

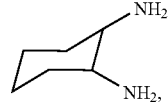

R comprises a tethered biotin moiety, M is a non-labile covalently bonded ligand, and the tether comprises an amide moiety.

In a further embodiment, the present invention relates to a compound of formula I and the attendant definitions wherein both of X taken together represent

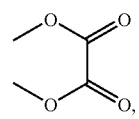

both of L taken together represent

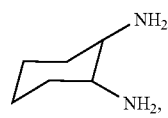

both R and M are tethered steroids wherein the steroids are estrogen, and the tethers comprise an amide moiety.

In a further embodiment, the present invention relates to a compound of formula I and the attendant definitions wherein both of X taken together represent

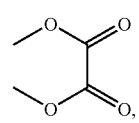

both of L taken together represent

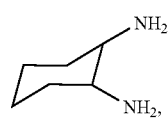

both R and M are tethered peptides comprising asparagine, glycine, and arginine, and the tethers comprise an amide moiety.

In a further embodiment, the present invention relates to a compound of formula I and the attendant definitions wherein both of X taken together represent

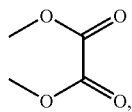

both of L taken together represent

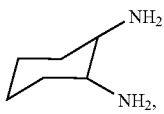

both R and M comprise tethered biotin moieties, and the tethers comprise an amide moiety.

In a further embodiment, the present invention relates to a compound of formula I and the attendant definitions wherein both of X taken together represent

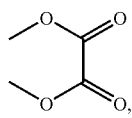

both of L taken together represent

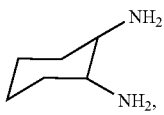

both R and M are tethered steroids wherein one steroid is estrogen and the other steroid is not, and the tethers comprise an amide moiety.

In a further embodiment, the present invention relates to a compound of formula I and the attendant definitions wherein both of X taken together represent

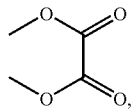

both of L taken together represent

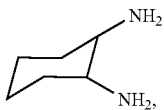

R is a tethered peptide comprising asparagine, glycine, and arginine, M is a non-labile covalently bonded ligand, and the tether comprises an amide moiety.

In a further embodiment, the present invention relates to a compound of formula I and the attendant definitions wherein both of X taken together represent

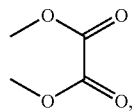

both of L taken together represent

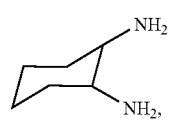

R comprises a tethered biotin moiety, M is a non-labile covalently bonded ligand, and the tether comprises an amide moiety.

In another aspect, the present invention provides methods of making the subject coordination complexes. In certain methods, combinatorial synthetic methods may be used.

In another embodiment the present invention relates to a compound comprising a platinum metal center, two cis labile ligands covalently bonded to the platinum metal center, two cis non-labile ligands covalently bonded to the platinum metal center, and at least one therapeutic agent covalently attached to the platinum metal center, wherein the platinum is in a +4 oxidation state, and wherein upon reduction of the platinum metal center to a +2 oxidation state the therapeutic agent is released from the platinum metal center.

In another embodiment, the present invention relates to a compound comprising a platinum metal center in the +4 oxidation state and a therapeutic agent covalently bonded to the platinum metal center. In a further embodiment, after release of the therapeutic agent from the platinum metal center, the compound comprising the platinum metal center is therapeutically effective.

In another embodiment, the present invention relates to a compound comprising a platinum metal center in the +4 oxidation state and a targeting moiety covalently bonded to the platinum metal center. In a further embodiment, after release of the targeting moiety from the platinum metal center, the compound comprising the platinum metal center is therapeutically effective.

In another embodiment, the present invention relates to a coordination complex comprising a metal ion and a therapeutic agent covalently attached to the metal ion, wherein reduction or oxidation of the metal ion precipitates release of the therapeutic agent from the metal ion, and wherein after release of the therapeutic agent from the metal ion, the coordination complex comprising the metal ion after release of the therapeutic agent is therapeutically effective.

In another embodiment, the present invention relates to a coordination complex comprising a metal ion and a targeting moiety covalently attached to the metal ion, wherein reduction or oxidation of the metal ion precipitates release of the targeting moiety from the metal ion, and wherein after release of the targeting moiety from the metal ion, the coordination complex comprising the metal ion after release of the targeting moiety is therapeutically effective.

In another embodiment, the present invention relates to a composition comprising any of the compounds of the present invention and a pharmaceutically effective excipient.

In another embodiment, the present invention relates to a method of treating a disease or condition comprising administering to a subject any of the compounds of the present invention or a mixture thereof. In certain instances, the disease or condition is cancer.

In a further embodiment, the subject methods of treatment comprise the release of the therapeutic agent from the platinum metal center, and wherein the cancer cells have receptors for the released therapeutic agent.

In a further embodiment, the method of treating cancer comprises the released therapeutic agent causing increased expression of HMGB1 to sensitize the cancer cells to the platinum metal center compound.

In a further embodiment, the method of treating cancer comprises selecting subjects having cancer cells that express a receptor for the therapeutic agent. In a further embodiment, the cancer cells express estrogen ER(+) receptors. In a further embodiment, prior to administering the compound comprising the platinum metal center, at least some of the cancer cells of the cancer to be treated are first determined to express a receptor for the therapeutic agent.

In another embodiment, the present invention relates to a method of treating cancer, comprising (a) screening one or more patients for cancer cells that display a receptor for a therapeutic agent; (b) selecting those patients that have cancer cells containing such a receptor; and (c) administering to the selected patients any of the subject coordination complexes of claims 1–24 or a combination thereof, wherein the compound administered comprises the therapeutic agent or a functional equivalent.

In another embodiment the present invention relates to a method of improving a drug comprising a compound of the present invention comprising (a) measuring the therapeutic effectiveness for a subject coordination complex of claim 21, (b) synthesizing or obtaining a derivative of the compound of claim 21 by varying the ligands on the platinum metal center or varying the composition of the tether to increase the time between release and optionally activation of the therapeutic agent and hydrolization of the cis labile ligands to form an active platinum metal compound, and (c) comparing the therapeutic effectiveness of the subject coordination complex of claim 21 to the therapeutic effectiveness of the derivative.

In other embodiments, this invention contemplates a kit including subject compositions, and optionally instructions for their use. Uses for such kits include, for example, therapeutic applications.

In another aspect, the compositions of the present invention may be used in the manufacture of a medicament for any number of uses, including for example treating any disease or other treatable condition of a patient. In still other aspects, the present invention is directed to a method for formulating coordination complexes of the present invention in a pharmaceutically acceptable carrier.

These embodiments of the present invention, other embodiments, and their features and characteristics, will be apparent from the description, drawings and claims that follow.

DETAILED DESCRIPTION OF INVENTION

Introduction

Figure 1:
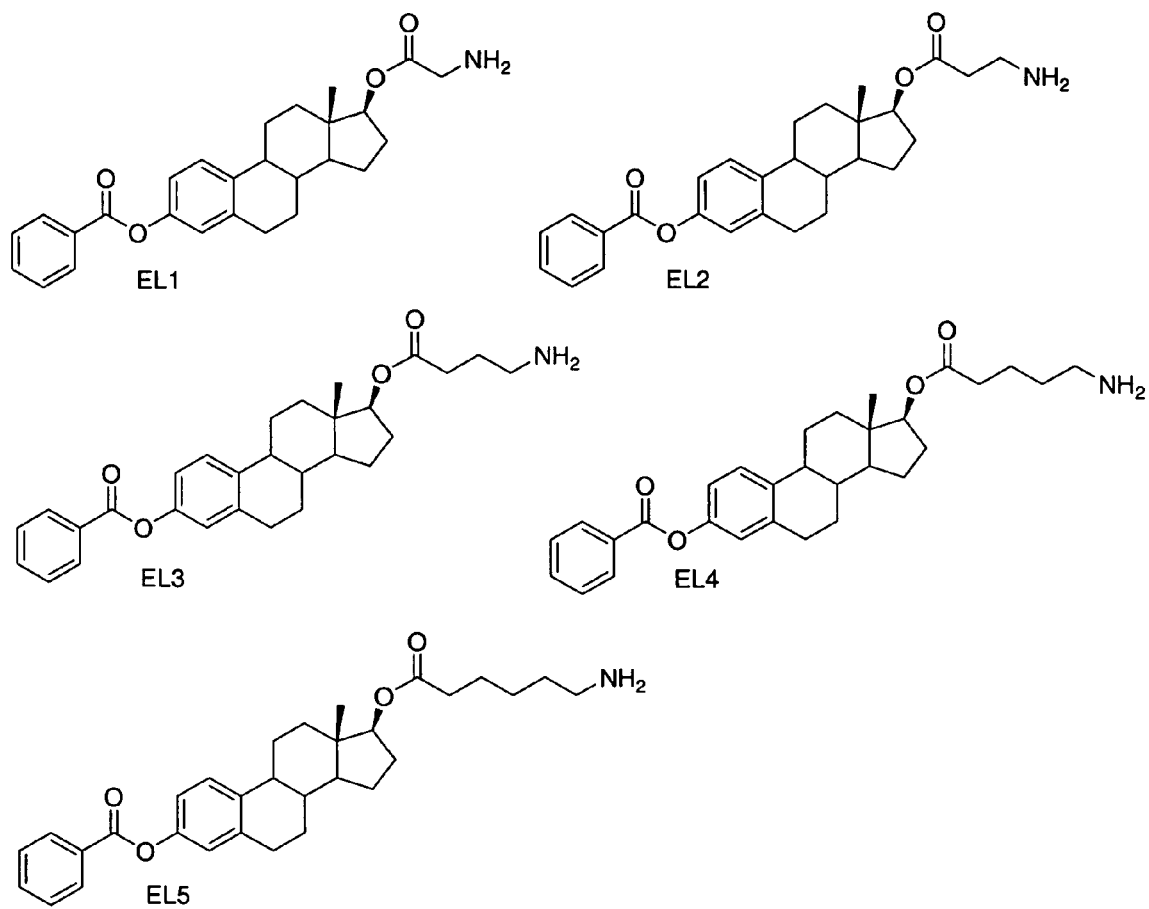
FIG. 1 depicts the amide modified estrogens EL1–EL5.

In part, the present invention is directed towards coordination complexes that have a covalently attached therapeutic agent and/or covalently attached targeting moiety. Upon release of the therapeutic agent or targeting moiety from a metal ion of the coordination complex, the resulting coordination complex is intended to be therapeutically effective. Upon release of the therapeutic agent the therapeutic agent is intended to be therapeutically effective as well.

In certain embodiments, release of the therapeutic agent and/or targeting moiety from the metal ion of the subject coordination complex is precipitated by a redox change at the metal ion to which the therapeutic agent and targeting moiety are covalently attached. In certain instances, the redox change may cause the therapeutic agent and targeting moiety to be released, whereas in other instances, the redox change could make it more likely that the therapeutic agent and targeting moiety are subsequently released from the metal ion. For example, a redox change at the metal ion may directly cause the therapeutic agent or targeting moiety to dissociate from the metal ion immediately. An example of such an instance is a redox change that causes a change in coordination geometry for the metal ion that reduces the number of ligands, thereby causing the therapeutic agent and targeting moiety to dissociate and thus be released. Alternatively, such a redox change may increase the likelihood that the therapeutic agent and targeting moiety disassociate over time or are displaced by another ligand. For example, a redox change could make substitution at the metal ion more likely whereas before the redox change substitution was not as likely. In addition and without limitation, for all of the subject coordination complexes, it may be the case that a covalently attached therapeutic agent and targeting moiety are released over time after administration without any redox change at the metal ion, notwithstanding whether a redox changes causes or increases the likelihood of release of the therapeutic agent and targeting moiety.

Without intending to limit the scope of the invention in any way, it is believed that in the case of the therapeutic agent the use of a redox change at the metal center to precipitate release of a covalently attached therapeutic agent will take advantage of the reducing environment found in cells. By this mechanism, for certain subject coordination complexes, release of a covalently attached therapeutic agent will occur (or be more likely to occur) in the cell upon reduction of the metal ion to which the therapeutic agent is covalently attached. By this means, two therapeutic agents, the released therapeutic agent and the coordination complex formed, will be generated in the same cell simultaneously. It may be the case that the two therapeutic agents, the released therapeutic agent and the coordination complex, may act on the same disease or condition or on a different disease or condition. Likewise, they may act synergistically or independently. For example and without limitation, as described below for the subject coordination complexes containing platinum as the metal ion and estrogen as the therapeutic agent, the released therapeutic agent (for this example, estrogen) may be used to increase the therapeutic effectiveness of the coordination complex (for this example, cisplatin) formed upon release.

Based in part on the approach described above, coordination complexes containing platinum and a therapeutic agent have been prepared. Based in part on the approach described above, coordination complexes containing platinum and a targeting moiety have also been prepared. One well-known coordination complex that is used to treat cancer is cisplatin. The utility of cisplatin as an anticancer treatment was discovered serendipitously over three decades ago. Today testicular cancer is treated by cisplatin with greater than 90% success rates. In addition, cisplatin is also used against head and neck, ovarian, bladder, lung, and breast tumors. Cisplatin can cause severe side effects, however, and is most effective against a narrow range of cancers; it is often rendered inactive due to intrinsic or acquired drug resistance.

Cisplatin can interact with RNA, proteins or sulfur-containing biomolecules, but DNA has been shown to be its primary biological target. The 1,2-intrastrand d(GpG) and d(ApG) cross-links are known to account for 90% of DNA-cisplatin interactions. In addition, cisplatin has been observed to form a small number of 1,3-intrastrand and interstrand cross-links with DNA. Cisplatin-DNA adducts have been shown to inhibit DNA replication, block transcription by RNA polymerase II and ultimately trigger programmed cell death, or apoptosis.

The 1,2-intrastrand cross-link has been shown to induce a pronounced bend in the DNA helix. The resulting wide and shallow minor groove opposite the platinum adduct are believed to serve as a recognition structure for a number of cellular proteins, including DNA repair proteins, histones, and HMG-domain proteins such as HMGB1. The cellular proteins that recognize platinum-DNA adducts may play a role in the mechanism of action of cisplatin cytotoxicity, as manifested by two main hypotheses that have evolved. One hypothesis asserts that cisplatin-damaged DNA 'hijacks' proteins away from their natural binding sites, leading to cellular stress and eventually cell death. The second hypothesis suggests that binding by cellular proteins shields cisplatin adducts from nucleotide excision repair (NER), allowing them to persist and drive apoptosis. These two hypotheses are not mutually exclusive. In support of the 'repair-shielding' hypothesis, it has been demonstrated that HMG-domain proteins shield cisplatin adducts from repair in vitro and in cells. Recent work has revealed that estrogen receptor-positive, ER (+), cells, when exposed to estrogen, are sensitized by a factor of two towards cisplatin treatment. Estrogen is known to induce over expression of HMGB1, a protein that shields cisplatin-adducts from NER.

In one embodiment of the present invention, subject coordination complexes comprising a covalently attached therapeutic agent and platinum have been prepared. For these complexes, platinum(IV) has been used. As illustrated in Scheme 1, and without intending to limit the scope of the invention in any way, the subject platinum(IV) coordination complexes are expected to be reduced to platinum(II) upon entering the reducing environment of the cell. The resultant platinum(II) complex, cisplatin, is expected to interact with DNA as described above. As shown for one such coordination complex in Scheme 1, upon reduction of BEPn to platinum(II), the covalently attached therapeutic agent, in this example estrogen with a tether, is expected to be released as the platinum(II) coordination complex forms the favored square planar geometry. The tether of the therapeutic agent, here in this example the ester linkers that covalently link estrogen to the metal ion, are expected to be hydrolyzed by intracellular esterases. The therapeutic agent in the form of free estrogen is then expected to bind to the ER, leading to HMGB1 upregulation and increased cell sensitivity to cisplatin. As described above, for this example, the covalently attached therapeutic agent, estrogen, and the coordination complex formed upon release of the therapeutic agent, cisplatin, are expected to act synergistically. For clarity, it is understood that this description of the activity of these platinum(IV) coordination complexes is not intended to limit the scope of the present invention.

Scheme 1.
Reduction of proposed platinum (IV) complexes to platinum (II) upon entering the reducing environment of the cell.

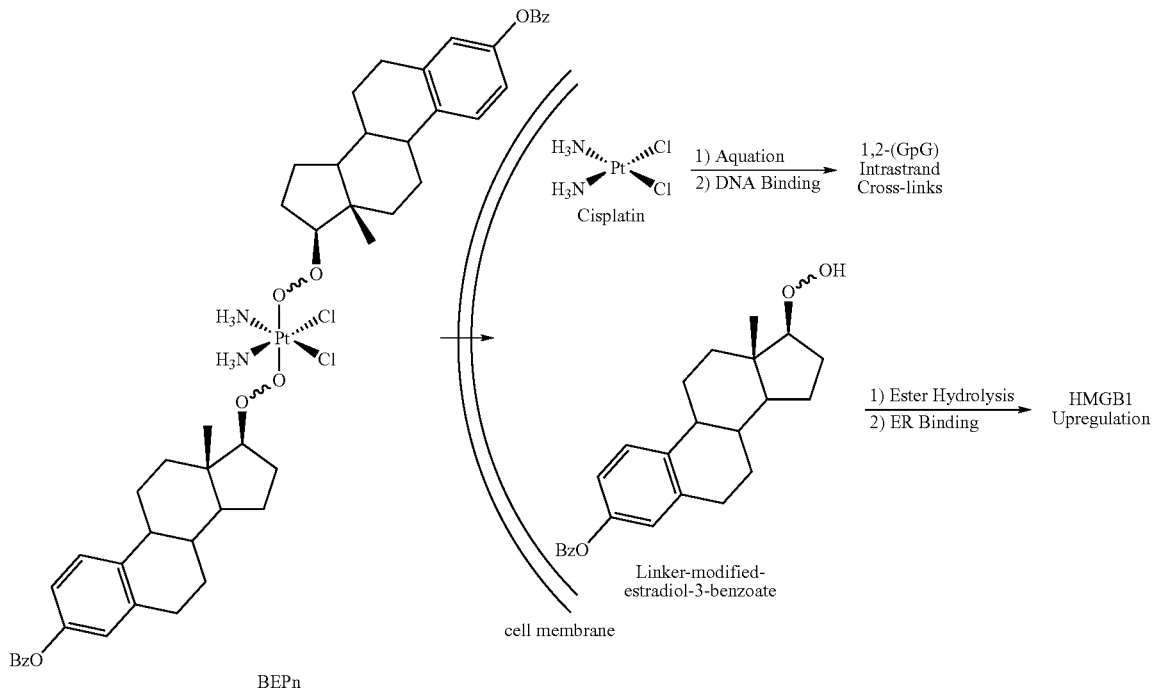

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The term "including" is used herein to mean "including but not limited to". "Including" and "including but not limited to" are used interchangeably.

The term "ligand" is art-recognized and refers to a species that interacts in some fashion with another species. In one example, a ligand may be a Lewis base that is capable of forming a coordinate bond with a Lewis Acid. In other examples, a ligand is a species, often organic, that forms a coordinate bond with a metal ion. Ligands, when coordinated to a metal ion, may have a variety of binding modes know to those of skill in the art, which include, for example, terminal (i.e., bound to a single metal ion) and bridging (i.e., one atom of the Lewis base bound to more than one metal ion).

The terms "labile" and "non-labile" are art-recognized and are usually used in this context in reference to a ligand bonded to a metal ion. Without intending to limit or modify the definition for the term as it is known in the art, a labile ligand may be understood to be a ligand whose bond to the metal ion is expected to break under certain circumstances. For example, for cisplatin, it has been shown that the chloride ligands will be replaced with water in vivo, so in this instance, the chloride ligands are termed labile. In contrast, under those same conditions, the amine ligands of cisplatin are not termed labile, for they are believed to remain coordinated to the platinum metal ion; hence, the amine ligands are non-labile. Likewise, in the example shown in Scheme 1, the therapeutic agent estrogen is not a labile ligand when bound to platinum(IV), whereas the coordinate bond is expected to break upon reduction to platinum(II).

The term "cis" is art-recognized and refers to, as used herein, the arrangement of two atoms or groups around a central metal atom such that the atoms or groups are next to each other.

The term "trans" is art-recognized and refers to, as used herein, the arrangement of two atoms or groups around a central metal atom such that the atoms or groups are not next to each other and are on opposite sides of the central metal atom.

The terms "Lewis acid" and "Lewis acidic" are art-recognized and refer to chemical moieties which can accept a pair of electrons from a Lewis base as defined above.

The terms "Lewis base" and "Lewis basic" are art-recognized and generally refer to a chemical moiety capable of donating a pair of electrons under certain reaction conditions. It may be possible to characterize a Lewis base as donating a single electron in certain complexes, depending on the identity of the Lewis base and the metal ion, but for most purposes, however, a Lewis base is best understood as a two electron donor. Examples of Lewis basic moieties include uncharged compounds such as alcohols, thiols, and amines, and charged moieties such as alkoxides, thiolates, carbanions, and a variety of other organic anions. In certain examples, a Lewis base may consist of a single atom, such as oxide ($O^{2-}$). In certain, less common circumstances, a Lewis base or ligand may be positively charged. A Lewis base, when coordinated to a metal ion, is often referred to as a ligand. Further description of ligands relevant to the present invention is presented herein.

The term "chelating agent" is art-recognized and refers to a molecule, often an organic one, and often a Lewis base, having two or more unshared electron pairs available for donation to a metal ion. The metal ion is usually coordinated by two or more electron pairs to the chelating agent. The terms, "bidentate chelating agent", "tridentate chelating agent", and "tetradentate chelating agent" are art-recognized and refer to chelating agents having, respectively, two, three, and four electron pairs readily available for simultaneous donation to a metal ion coordinated by the chelating agent. Usually, the electron pairs of a chelating agent forms coordinate bonds with a single metal ion; however, in certain examples, a chelating agent may form coordinate bonds with more than one metal ion, with a variety of binding modes being possible.

The term "coordination" is art-recognized and refers to an interaction in which one multi-electron pair donor coordinatively bonds (is "coordinated") to one metal ion.

The term "coordinate bond" is art-recognized and refers to an interaction between an electron pair donor and a coordination site on a metal ion leading to an attractive force between the electron pair donor and the metal ion. The use of this term is not intended to be limiting, in so much as certain coordinate bonds may also be classified as having more or less covalent character (if not entirely covalent character) depending on the nature of the metal ion and the electron pair donor.

The term "coordination site" is art-recognized and refers to a point on a metal ion that can accept an electron pair donated, for example, by a liquid or chelating agent.

The term "free coordination site" is art-recognized and refers to a coordination site on a metal ion that is vacant or occupied by a species that is weakly donating. Such species is readily displaced by another species, such as a Lewis base.

The term "coordination number" is art-recognized and refers to the number of coordination sites on a metal ion that are available for accepting an electron pair.

The term "coordination geometry" is art-recognized and refers to the manner in which coordination sites and free coordination sites are spatially arranged around a metal ion. Some examples of coordination geometry include octahedral, square planar, trigonal, trigonal biplanar and others known to those of skill in the art.

The term "covalent bond" is art-recognized and refers to a bond between two atoms where electrons are attracted electrostatically to both nuclei of the two atoms, and the net effect of increased electron density between the nuclei counterbalances the internuclear repulsion. The term covalent bond includes coordinate bonds when the bond is with a metal ion.

The term "covalently attached", when used in reference to a subject coordination complex, refers to the attachment of a therapeutic agent to a metal ion in the coordination complex. As described in detail herein, the therapeutic agent, or modified form e.g., deprotonated, may form a coordinate bond directly with the metal ion, or alternatively, the therapeutic agent may be modified by a tether that forms the coordinate bond to the metal ion.

The term "complex" is art-recognized and refers to a compound formed by the union of one or more electron-rich and electron-poor molecules or atoms capable of independent existence with one or more electronically poor molecules or atoms, each of which is also capable of independent existence. Examples of complexes include associations between antigen/antibodies, lectin/avidin, target polynucleotide/probe oligonucleotide, antibody/anti-antibody, receptor/ligand, enzyme/ligand, polypeptide/polypeptide, polypeptide/polynucleotide, polypeptide/co-factor, polypeptide/substrate, polypeptide/inhibitor, polypeptide/small molecule, and the like. "Member of a complex" refers to one moiety of the complex, such as an antigen or ligand. "Protein complex" or "polypeptide complex" refers to a complex comprising at least one polypeptide.

A "coordination complex" is one type of a complex, in which there is a coordinate bond between a metal ion and an electron pair donor. For example, cisplatin is a coordination complex. A transition metal complex is a coordination complex in which the metal ion is a transition metal ion. In general, the terms "compound," "composition," "agent" and the like discussed herein include complexes, coordination complexes and transition metal complexes. As a general matter, the teachings of *Advanced Inorganic Chemistry* by Cotton and Wilkinson are referenced as supplementing the definitions herein in regard to coordination complexes and related matters.

In certain circumstances, a coordination complex may be understood to be composed of its constitutive components. For example, a coordination complex may have the following components: (i) one or more metal ions, which may or may not be the same atom, have the same charge, coordination number or coordination geometry and the like; and (ii) one or more Lewis bases that form coordinate bonds with the metal ion(s). Examples of such Lewis bases include chelating agents and ligands.

If a transitional metal complex is charged, in that the transition metal ion and any Lewis bases, in the aggregate, are not neutral, then such a complex will usually have one or more counterions to form a neutral compound. Such counterions may or may not be considered part of the coordination complex depending on how the term coordination complex is used. Counterions generally do not form coordinate bonds to the metal ion, although they may be associated, often in the solid state, with the metal ion or Lewis bases that make up the coordination complex. Some examples of counterions include monoanions such as nitrate, chloride, tetrafluoroborate, hexafluorophosphate, and monocarboxylates having the general formula $RCOO^-$, and dianions such as sulfate. In some cases, coordination complexes themselves may serve as counterions to another coordination complex, as in Magnus (green) salt $[Pt(NH_3)_4]^{2+}[PtCl_4]^{2-}$.

The same chemical moiety may be either a ligand or a counterion to a coordination complex. For example, the anionic ligand chloride may be either coordinately bound to a metal ion or may act as a counterion without any need for bond formation. The exact form observed for chloride in any coordination complex will depend on a variety of factors, including theoretical considerations, such as kinetic versus thermodynamic effects, and the actual synthetic procedures utilized to make the coordination complex, such as the extent of reaction, acidity, concentration of chloride. These considerations are applicable to other counterions as well.

Additionally, a coordination complex may be solvated. Solvation refers to molecules, usually of solvent and often water, that associate with the coordination complex in the solid state. Again, as for counterions, such solvation molecules may or may not be considered part of the coordination complex depending on how the term coordination complex is used.

The term "tether" is art-recognized and refers to, as used herein, a chemical linking moiety between a metal ion center and another chemical moiety, often a therapeutic agent. As such, the tether may be considered part of the chemical moiety (e.g., therapeutic agent).

The term "steroid" is art-recognized and refers to any of numerous naturally occurring or synthetic fat-soluble organic compounds having as a basis 17 carbon atoms arranged in four rings and including the sterols and bile acids, adrenal and sex hormones, certain natural drugs such as digitalis compounds, and the precursors of certain vitamins.

The term "therapeutic agent" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject. Examples include steroids and esters of steroids (e.g., estrogen, progesterone, testosterone, androsterone, cholesterol, norethindrone, digitoxigenin, cholic acid, deoxycholic acid, and chenodeoxycholic acid), boron-containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, and kedarcidin chromophore), heavy metal complexes (e.g., cisplatin), hormone antagonists (e.g., tamoxifen), non-specific (non-antibody) proteins (e.g., sugar oligomers), oligonucleotides (e.g., antisense oligonucleotides that bind to a target nucleic acid sequence (e.g., mRNA sequence)), peptides, photodynamic agents (e.g., rhodamine 123), radionuclides (e.g., I-131, Re-186, Re-188, Y-90, Bi-212, At-211, Sr-89, Ho-166, Sm-153, Cu-67 and Cu-64), toxins (e.g., ricin), and transcription-based pharmaceuticals. In certain embodiments for treating or preventing the establishment or growth of a tumor, the therapeutic agent may be a radionuclide, toxin, hormone antagonist, heavy metal complex, oligonucleotide, chemotherapeutic nucleotide, peptide, non-specific (non-antibody) protein, a boron compound or an enediyne. In other embodiments for treating or preventing the establishment or growth of a bacterial infection, the therapeutic agent may be an antibiotic, radionuclide or oligonucleotide. In still other embodiments for treating or preventing the establishment or growth of a viral infection, the therapeutic agent may be an antiviral compound, radionuclide or oligonucleotide. In yet other embodiments for treating or preventing the establishment or growth of a fungal infection, the therapeutic agent may be an antifungal compound, radionuclide or oligonucleotide.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compounds of the present invention, such as the subject coordination complex, may be administered in a sufficient amount to produce a at a reasonable benefit/risk ratio applicable to such treatment.

The terms "combinatorial library" or "library" are art-recognized and refer to a plurality of compounds, which may be termed "members," synthesized or otherwise prepared from one or more starting materials by employing either the same or different reactants or reaction conditions at each reaction in the library. There are a number of other terms of relevance to combinatorial libraries (as well as other technologies). The term "identifier tag" is art-recognized and refers to a means for recording a step in a series of reactions used in the synthesis of a chemical library. The term "immobilized" is art-recognized and, when used with respect to a species, refers to a condition in which the species is attached to a surface with an attractive force stronger than attractive forces that are present in the intended environment of use of the surface, and that act on the species. The term "solid support" is art-recognized and refers to a material which is an insoluble matrix, and may (optionally) have a rigid or semi-rigid surface. The term "linker" is art-recognized and refers to a molecule or group of molecules connecting a support, including a solid support or polymeric support, and a combinatorial library member. The term "polymeric support" is art-recognized and refers to a soluble or insoluble polymer to which a chemical moiety can be covalently bonded by reaction with a functional group of the polymeric support. The term "functional group of a polymeric support" is art-recognized and refers to a chemical moiety of a polymeric support that can react with an chemical moiety to form a polymer-supported amino ester.

The term "synthetic" is art-recognized and refers to production by in vitro chemical or enzymatic synthesis.

The term "meso compound" is art-recognized and refers to a chemical compound which has at least two chiral centers but is achiral due to a plane or point of symmetry.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" is art-recognized and refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" is art-recognized and refers to molecules with identical chemical constitution and containing more than one stereocenter, but which differ in configuration at only one of these stereocenters.

The term "$ED_{50}$" is art-recognized and refers to the dose of a drug or other compound or coordination complex which produces 50% of its maximum response or effect, or alternatively, the dose which produces a pre-determined response in 50% of test subjects or preparations.

The term "$LD_{50}$" is art-recognized and refers to the dose of a drug or other compound or coordination complex which is lethal in 50% of test subjects.

The term "therapeutic index" is art-recognized and refers to the therapeutic index of a drug or other compound or coordination complex defined as $LD_{50}/ED_{50}$.

The term "structure-activity relationship" or "(SAR)" is art-recognized and refers to the way in which altering the molecular structure of a drug or other compound or coordination complex alters its interaction with a receptor, enzyme, nucleic acid or other target and the like.

The term "agonist" is art-recognized and refers to a compound or coordination complex that mimics the action of natural transmitter or, when the natural transmitter is not known, causes changes at the receptor complex in the absence of other receptor ligands.

The term "antagonist" is art-recognized and refers to a compound or coordination complex that binds to a receptor site, but does not cause any physiological changes unless another receptor ligand is present.

The term "competitive antagonist" is art-recognized and refers to a compound or coordination complex that binds to a receptor site; its effects may be overcome by increased concentration of the agonist.

The term "partial agonist" is art-recognized and refers to a compound or coordination complex that binds to a receptor site but does not produce the maximal effect regardless of its concentration.

The term "aliphatic" is art-recognized and refers to a linear, branched, cyclic alkane, alkene, or alkyne. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$–$C_{30}$ for straight chain, $C_3$–$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like. Exemplary substituted alkyls are described below. Cycloalkyls may be further substituted with alkyls, alkenyls, alkoxys, alkylthios, aminoalkyls, carbonyl-substituted alkyls, —CN, and the like.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

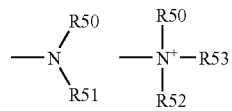

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "ammine" is art-recognized are refers to a compound containing an ammonia moiety or moieties coordinated to a metal ion. The term "ammonia" is art-recognized an refers to an amine group substituted with hydrogens.

The term "acylamino" is art-recognized and refers to a moiety that may be represented by the general formula:

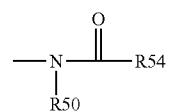

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

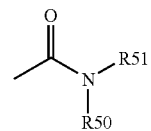

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S—alkyl, —S—alkenyl, —S—alkynyl, and —S—(CH$_2$)$_m$—R61, wherein m and R61 are defined above. Representative alkylthio groups include methylthio, ethyl thio, and the like.

The term "carbonyl" is art recognized and includes such moieties as may be represented by the general formulas:

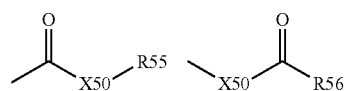

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O—alkyl, —O—alkenyl, —O—alkynyl, —O—(CH$_2$)$_m$—R61, where m and R61 are described above.

The term "sulfonate" is art recognized and refers to a moiety that may be represented by the general formula:

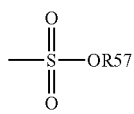

in which R57 is an electron pair, hydrogen, alkyl, cycloalkyl, or aryl.

The term "sulfate" is art recognized and includes a moiety that may be represented by the general formula:

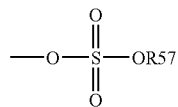

in which R57 is as defined above.

The term "sulfonamido" is art recognized and includes a moiety that may be represented by the general formula:

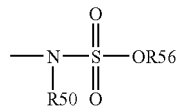

in which R50 and R56 are as defined above.

The term "sulfamoyl" is art-recognized and refers to a moiety that may be represented by the general formula:

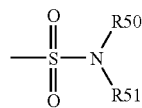

in which R50 and R51 are as defined above.

The term "sulfonyl" is art-recognized and refers to a moiety that may be represented by the general formula:

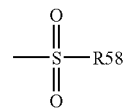

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

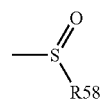

in which R58 is defined above.

The term "phosphoryl" is art-recognized and may in general be represented by the formula:

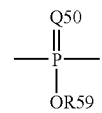

wherein Q50 represents S or O, and R59 represents hydrogen, a lower alkyl or an aryl. When used to substitute, e.g., an alkyl, the phosphoryl group of the phosphorylalkyl may be represented by the general formulas:

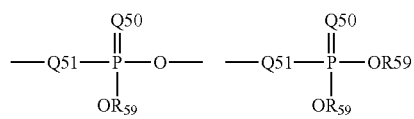

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

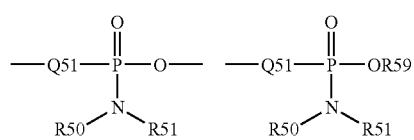

wherein Q51, R50, R51 and R59 are as defined above.

The term "phosphonamidite" is art-recognized and may be represented in the general formulas:

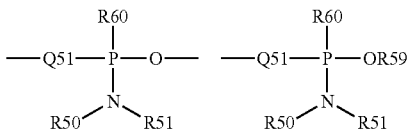

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, *Handbook of Chemistry and Physics*, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds that may be substituted or unsubstituted.

The term "protecting group" is art-recognized and refers to temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed by Greene and Wuts in *Protective Groups in Organic Synthesis* ($2^{nd}$ ed., Wiley: New York, 1991).

The term "hydroxyl-protecting group" is art-recognized and refers to those groups intended to protect a hydrozyl group against undesirable reactions during synthetic procedures and includes, for example, benzyl or other suitable esters or ethers groups known in the art.

The term "carboxyl-protecting group" is art-recognized and refers to those groups intended to protect a carboxylic acid group, such as the C-terminus of an amino acid or peptide or an acidic or hydroxyl azepine ring substituent, against undesirable reactions during synthetic procedures and includes. Examples for protecting groups for carboxyl groups involve, for example, benzyl ester, cyclohexyl ester, 4-nitrobenzyl ester, t-butyl ester, 4-pyridylmethyl ester, and the like.

The term "amino-blocking group" is art-recognized and refers to a group which will prevent an amino group from participating in a reaction carried out on some other functional group, but which can be removed from the amine when desired. Such groups are discussed by in Ch. 7 of Greene and Wuts, cited above, and by Barton, *Protective Groups in Organic Chemistry* ch. 2 (McOmie, ed., Plenum Press, New York, 1973). Examples of suitable groups include acyl protecting groups such as, to illustrate, formyl, dansyl, acetyl, benzoyl, trifluoroacetyl, succinyl, methoxysuccinyl, benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonyl-aminocarbonyl. Preferred amino-blocking groups are benzyl (—CH$_2$C$_6$H$_5$), acyl [C(O)R1] or SiR1$_3$ where R1 is $C_1$–$C_4$ alkyl, halomethyl, or 2-halo-substituted-($C_2$–$C_4$ alkoxy), aromatic urethane protecting groups as, for example, carbonylbenzyloxy (Cbz); and aliphatic urethane protecting groups such as t-butyloxycarbonyl (Boc) or 9-fluorenylmethoxycarbonyl (FMOC).

The definition of each expression, e.g. lower alkyl, m, n, p and the like, when it occurs more than once in any structure, is intended to be independent of its definition elsewhere in the same structure.

The term "electron-withdrawing group" is art-recognized, and refers to the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, March, *Advanced Organic Chemistry* 251–59 (McGraw Hill Book Company: New York, 1977). The Hammett constant values are generally negative for electron donating groups ($\sigma(P)=-0.66$ for NH$_2$) and positive for electron withdrawing groups ($\sigma(P)=0.78$ for a nitro group), $\sigma(P)$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "amino acid" is art-recognized and refers to all compounds, whether natural or synthetic, which include both an amino functionality and an acid functionality, including amino acid analogs and derivatives.

The terms "amino acid residue" and "peptide residue" are art-recognized and refer to an amino acid or peptide molecule without the —OH of its carboxyl group.

The term "amino acid residue" further includes analogs, derivatives and congeners of any specific amino acid referred to herein, as well as C-terminal or N-terminal protected amino acid derivatives (e.g. modified with an N-terminal or C-terminal protecting group).

The names of the natural amino acids are abbreviated herein in accordance with the recommendations of IUPAC-IUB.

A "reversed" or "retro" peptide sequence as disclosed herein refers to that part of an overall sequence of covalently-bonded amino acid residues (or analogs or mimetics thereof) wherein the normal carboxyl-to amino direction of peptide bond formation in the amino acid backbone has been reversed such that, reading in the conventional left-to-right direction, the amino portion of the peptide bond precedes (rather than follows) the carbonyl portion. See, generally, Goodman et al. *Accounts of Chem. Res.* 12:423 (1979).

The reversed orientation peptides described herein include (a) those wherein one or more amino-terminal residues are converted to a reversed ("rev") orientation (thus yielding a second "carboxyl terminus" at the left-most portion of the molecule), and (b) those wherein one or more carboxyl-terminal residues are converted to a reversed ("rev") orientation (yielding a second "amino terminus" at the right-most portion of the molecule). A peptide (amide) bond cannot be formed at the interface between a normal orientation residue and a reverse orientation residue.

Therefore, certain reversed peptide compounds of the invention may be formed by utilizing an appropriate amino acid mimetic moiety to link the two adjacent portions of the sequences depicted above utilizing a reversed peptide (reversed amide) bond.

The reversed direction of bonding in such compounds will generally, in addition, require inversion of the enantiomeric configuration of the reversed amino acid residues in order to maintain a spatial orientation of side chains that is similar to that of the non-reversed peptide. The configuration of amino acids in the reversed portion of the peptides is usually (D), and the configuration of the non-reversed portion is usually (L). Opposite or mixed configurations are acceptable when appropriate to optimize a binding activity.

The term "nucleic acid" is art-recognized and refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

The terms "gene" or "recombinant gene" are art-recognized and refer to a nucleic acid comprising an open reading frame encoding a polypeptide, including both exonic and (optionally) intronic sequences.

The term "gene construct" is art-recognized and refers to a vector, plasmid, viral genome or the like which includes an "coding sequence" for a polypeptide or which is otherwise transcribable to a biologically active RNA (e.g., antisense, decoy, ribozyme, etc), can transfect cells, in certain embodiments mammalian cells, and may cause expression of the coding sequence in cells transfected with the construct.

The term "homology" is art-recognized and refers to sequence similarity between two peptides or between two nucleic acid molecules.

The term "operably linked" is art-recognized and refers to the relationship between two nucleic acid regions, means that they are functionally related to each other.

The term "antisense" nucleic acid is art-recognized and refers to oligonucleotides which specifically hybridize (e.g., bind) under cellular conditions with a gene sequence, such as at the cellular mRNA and/or genomic DNA level, so as to inhibit expression of that gene, e.g., by inhibiting transcription and/or translation. The binding may be by conventional base pair complementarily, or, for example, in the case of binding to DNA duplexes, through specific interactions in the major groove of the double helix.

The term "host cell" is art-recognized and refers to a cell transduced with a specified transfer vector. The cell is optionally selected from in vitro cells such as those derived from cell culture, ex vivo cells, such as those derived from an organism, and in vivo cells, such as those in an organism. "Recombinant host cells" refers to cells which have been transformed or transfected with vectors constructed using recombinant DNA techniques.

The terms "recombinant protein," "heterologous protein" and "exogenous protein" are art-recognized and are used interchangeably to refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

The term "regulatory element" is art-recognized and refers to nucleotide sequences (such as DNA sequences) that induce or control transcription of protein coding sequences with which they are operably linked. Examples of regulatory elements categorized by function include initiation signals, enhancers, promoters and the like. Exemplary regulatory elements are described in Goeddel; *Methods in Enzymology* 185 (1990). In certain embodiments, transcription of a gene or other DNA is under the control of a promoter sequence (or other regulatory element) which controls the expression of a coding sequence in a cell-type in which expression is intended. A variety of promoters categorized by function are known. The term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a urogenital origin, e.g., renal cells, or cells of a neural origin, e.g., neuronal cells. The term also covers so-called "leaky" promoters, which regulate expression of a selected DNA primarily in one tissue, but cause expression in other tissues as well. The term "inducible" promoter refers to a promoter which is under environmental or developmental regulation. The term "constitutive" promoter refers to a promoter which is active under most environmental and developmental conditions.

The term "transfection" is art-recognized and refers to the introduction of a nucleic acid, e.g., an expression vector, into a recipient cell, which in certain embodiments may be by nucleic acid-mediated gene transfer. "Transformation," as used with respect to transfected nucleic acid, is an art-recognized term and refers to a process in which a cell's genotype is changed as a result of the cellular uptake of exogenous nucleic acid.

The term "transfer vector" is art-recognized and refers to a first nucleic acid molecule to which a second nucleic acid has been linked, and includes for example plasmids, cosmids or phages (as discussed in grater detail below). In certain embodiments of the present invention, the therapeutic agent is the second nucleic acid. One type of transfer vector is an episome, i.e., a nucleic acid capable of extra-chromosomal replication.

In certain embodiments, a transfer vector may be an "expression vector," which refers to a replicable DNA construct used to express DNA which encodes the desired protein and which includes a transcriptional unit comprising an assembly of (i) genetic element(s) having a regulatory role in gene expression, for example, promoters, operators, or enhancers, operatively linked to (ii) a DNA sequence encoding a desired protein which is transcribed into mRNA and translated into protein, and (iii) appropriate transcription and translation initiation and termination sequences. In certain embodiments, the therapeutic agent is the DNA sequence. The choice of promoter and other regulatory elements generally varies according to the intended host cell. In general, expression vectors of utility in recombinant DNA techniques are often in the form of "plasmids," which refer to circular double stranded DNA loops which, in their vector form are not bound to the chromosome. The invention is intended to include such other forms of expression vectors which serve equivalent functions and which become known in the art subsequently hereto.

Certain transfer vectors may contain regulatory elements for controlling transcription or translation, which may be generally derived from mammalian, microbial, viral or insect genes. The ability to replicate in a host, usually conferred by an origin of replication, and a selection gene to facilitate recognition of transformants, may additionally be incorporated.

The design of any transfer vector may depend on such factors as the choice of the host cell to be transformed and/or the type of protein desired to be expressed. Moreover, the vector's copy number, the ability to control that copy number and the expression of any other proteins encoded by the vector, such as antibiotic markers (e.g., ampicillin), may also be considered.

The term "transgenic animal" is art-recognized and refers to any animal, often a non-human mammal, a bird or an amphibian, in which one or more of the cells of the animal contain nucleic acid introduced by way of human intervention, such as by transgenic techniques well known in the art. Such nucleic acid may be referred to as a "transgene." The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. A transgene may be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene may also be present in a cell in the form of an episome. A transgene may include one or more regulatory elements and any other nucleic acid, such as introns, that may be necessary for optimal expression of a selected nucleic acid. In certain embodiments, a transgene comprises a nucleic acid sequence of interest and one or more regulatory elements for controlling transcription of the nucleotide sequence encoded by such nucleic acid sequence, e.g., the regulatory element is operably linked to a nucleic acid.

In certain embodiments, the transgene or other therapeutic agent may be a "gene therapy construct," which is an expression vector which may alter the phenotype of a cell when taken up by the cell, or a gene construct. In certain embodiments, the gene therapy construct may be a "recombinant coding sequence" which encodes a polypeptide, or is transcribable to an antisense nucleic acid, a ribozyme, or any other RNA product which alters the phenotype of the cell in which it is produced. "Recombinant gene" refers to a genetic construct including a "recombinant coding sequence."

The term "antibody" is art-recognized and refers to whole antibodies, e.g., of any isotype (IgG, IgA, IgM, IgE, etc.), and includes fragments thereof which are also specifically reactive with a vertebrate, e.g., mammalian, protein. Antibodies may be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')$_2$, Fab', Fv, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal or other purified preparations of antibodies and recombinant antibodies.

"Human monoclonal antibodies" or "humanized" murine antibodies, as the terms are used herein, refer to murine monoclonal antibodies "humanized" by genetically recombining the nucleotide sequence encoding the murine Fv region (i.e., containing the antigen binding site) or the complementarity-determining regions thereof with the nucleotide sequence encoding at least a human constant domain region and an Fc region, e.g., in a manner similar to that disclosed in European Patent Application Publication No. 0,411,893 A3. Some additional murine residues may also be retained within the human variable region framework domains to ensure proper target site binding characteristics. In certain embodiments, humanized antibodies may decrease the immunoreactivity of the antibody or polypeptide in the host recipient, permitting an increase in the half-life and a reduction in the possibility of adverse immune reactions.

An "imaging agent" shall mean a composition capable of generating a detectable image upon binding with a target and shall include radionuclides (e.g., In-111, Tc-99m, I-123, I-125 F-18, Ga-67, Ga-680); for Positron Emission Tomography (PET) and Single Photon Emission Tomography (SPECT), unpair spin atoms and free radicals (e.g., Fe, lanthanides, and Gd); and contrast agents (e.g., chelated (DTPA) manganese) for Magnetic Resonance Imaging (MRI). Imaging agents are discussed in greater detail below.

The term "small molecule" is art-recognized and refers to a composition which has a molecular weight of less than about 2000 amu, or less than about 1000 amu, and even less than about 500 amu. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a small molecule that is often identified as being an organic or medicinal compound, and does not include molecules that are exclusively nucleic acids, peptides or polypeptides.

A "target" shall mean a site to which targeted constructs bind. A target may be either in vivo or in vitro. In certain embodiments, a target may be a tumor (e.g., tumors of the brain, lung (small cell and non-small cell), ovary, prostate, breast and colon as well as other carcinomas and sarcomas). In other embodiments, a target may be a site of infection (e.g., by bacteria, viruses (e.g., HIV, herpes, hepatitis) and pathogenic fungi (Candida sp.). In still other embodiments, a target may refer to a molecular structure to which a targeting moiety binds, such as a hapten, epitope, receptor, dsDNA fragment, carbohydrate or enzyme. Additionally, a target may be a type of tissue, e.g., neuronal tissue, intestinal tissue, pancreatic tissue etc, or any cell type.

"Target cells", which may serve as a target, include prokaryotes and eukaryotes, including yeasts, plant cells and animal cells. Alternatively, the target cells may form part of the tissue in an animal. Thus, target cells may include, for example, the cells lining the alimentary canal, such as the oral and pharyngeal mucosa, cells forming the villi of the small intestine, cells lining the large intestine, cells lining the respiratory system (nasal passages/lungs) of an animal (which may be contacted by inhalation of the subject invention), dermal/epidermal cells, cells of the vagina and rectum, cells of internal organs including cells of the placenta and the so-called blood/brain barrier, brain cells, etc.

The term "targeting moiety" refers to any molecular structure which assists a compound or other molecule in binding or otherwise localizing to a particular target, a a target area, entering target cell(s), binding to a target receptor, etc. For example, targeting moieties may include peptides, lipids (including cationic, neutral, and steroidal lipids, virosomes, and liposomes), antibodies, lectins, ligands, sugars, steroids, hormones, nutrients, and proteins may serve as targeting moieties. Other examples of targeting moieties are described in more detail below.

The term "isolated", as used herein with reference to proteins and other biological materials, refers to a preparation of protein or material that is essentially free from contaminating proteins and other materials that normally would be present in association with the protein or material, e.g., in the cellular milieu in which the protein or complex is found endogenously. Thus, an isolated protein is isolated from cellular components that normally would "contaminate" or interfere with the study of the protein in isolation, for instance while screening for inhibitors thereof. It is to be understood, however, that an "isolated" complex may incorporate other proteins the modulation of which, by the subject protein or protein complex, is being investigated.

The terms "label" or "labeled" refer to incorporation of a detectable marker into a molecule, such as a polypeptide, small molecule or subject composition. Various methods of labeling polypeptides and other molecules are known in the art and may be used. Examples of labels include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance and other complications.

The terms "antineoplastic" and "antineoplastic agent" are art-recognized, and describe therapeutic agents that prevent the development, maturation, or spread of cells characterized by abnormal malignant growth, e.g., for treating or preventing cancer.

The term "interact" as used herein is meant to include detectable relationships or associations (e.g. biochemical interactions) between molecules, such as interactions between protein-protein, protein-nucleic acid, nucleic acid-nucleic acid and protein-small molecule or nucleic acid-small molecule in nature.

The term "modulation" is art-recognized and refers to up regulation (i.e., activation or stimulation), down regulation (i.e., inhibition or suppression) of a response, or the two in combination or apart.

The term "treating" is art-recognized and refers to curing as well as ameliorating at least one symptom of any condition or disease.

The term "prophylactic" or "therapeutic" treatment is art-recognized and refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

A "patient," "subject" or "host" to be treated by the subject method may mean either a human or non-human animal.

The term "mammal" is known in the art, and exemplary mammals include humans, primates, bovines, porcines, canines, felines, and rodents (e.g., mice and rats).

The term "bioavailable" is art-recognized and refers to a form of the subject invention that allows for it, or a portion of the amount administered, to be absorbed by, incorporated to, or otherwise physiologically available to a subject or patient to whom it is administered.

The term "pharmaceutically-acceptable salts" is art-recognized and refers to the relatively non-toxic, inorganic and organic acid addition salts of compounds, including, for example, coordination complexes of the present invention.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "systemic administration," "administered systemically," "peripheral administration" and "administered peripherally" are art-recognized and refer to the administration of a subject supplement, composition, therapeutic or other material other than directly into the central nervous system, such that it enters the patient's system and, thus, is subject to metabolism and other like processes, for example, subcutaneous administration.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

Contemplated equivalents of the compounds described herein include compounds which otherwise correspond thereto, and which have the same general properties thereof (such as other coordination complexes comprising tethered therapeutic agents), wherein one or more simple variations of substituents are made which do not adversely affect the characteristics of the compounds of interest. In general, the compounds of the present invention may be prepared by the methods illustrated in the general reaction schema as, for example, described below, or by modifications thereof, using readily available starting materials, reagents and conventional synthesis procedures. In these reactions, it is also possible to make use of variants which are in themselves known, but are not mentioned here.

Metal Ions

The present invention contemplates the use of a variety of different metal ions. The metal atom may be selected from those that have usually at least four, five, six, seven or more coordination sites. In certain embodiments, the metal ion in the subject coordination complex will be redox active. A non-limiting list of metal ions for which the present invention may be employed (including exemplary and non-limiting oxidation states for them) includes $Co^{3+}$, $Cr^{3+}$, $Hg^{2+}$, $Pd^{2+}$, $Pt^{2+}$, $Pd^{4+}$, $Pt^{4+}$, $Rh^{3+}$, $Ir^{3+}$, $Ru^{3+}$, $Co^{2+}$, $Ni^{2+}$, $Cu^{2+}$, $Zn^{2+}$, $Cd^{2+}$, $Pb^{2+}$, $Mn^{2+}$, $Fe^{3+}$, $Fe^{2+}$, Tc, $Au^{3+}$, $Au^+$, $Ag^+$, $Cu^+$, $MoO_2^{2+}$, $Ti^{3+}$, $Ti^{4+}$, $CH_3Hg^+$, and $Y^{+3}$.

The metal ion to be used in the subject invention depends in part on the use to which the resulting coordination complex may be put. For example, platinum(II) may be used in those coordination complexes that may be used as therapeutics to treat cancer, neoplasms and other diseases or conditions. Alternatively, other metal ions may be used for the same or other diseases or conditions.

A variety of starting materials including or precursor metal reagents, may be used to prepare the subject coordination complexes.

Ligands

A number of ligands known to those of skill in the art may be used in the subject coordination complexes. For example, ligands for binding metal ions will generally include functional groups capable of interaction with a metal center, e.g., heteroatoms such as nitrogen, oxygen, sulfur, and phosphorus.

More specifically, ligands of the present invention will usually include organic electron donor moieties. Metal cations that necessarily (by definition) are Lewis acidic are able to bind various Lewis basic entities, including those that are negatively charged. Accordingly, in certain embodiments, the subject ligands with one or more functional groups having an electron pair donor (Lewis base) capable of coordination with the transition metal. In general, the functional group will be a strongly acidic group, e.g., with a pKa less than about 7, and more preferably less than 5, which can produce a conjugate base that, under the reaction conditions, is a strong enough Lewis base to donate an electron pair to a metal atom to form a coordinate bond with the cationic form of the metal. However, the degree of this Lewis acid-to-Lewis base interaction is a function not only of the particular metal center coordinated to a functional group, but also of the Lewis base itself, because the latter may vary in the degree of basicity as well as in size and steric accessibility.

The types of Lewis base functional groups capable of forming coordinate complexes with metal ions are too numerous to categorize here, and are known to those of skill in the art. In many embodiments, ligands will include bases which bear atoms from Periodic Groups 15 and 16. Lewis bases from Group 15 contain nitrogen, phosphorous, arsenic, antimony or bismuth atoms as electron pair donors.

Lewis bases from Group 16 contain oxygen, sulfur, or selenium atoms as electron pair donors.

Exemplary Lewis basic moieties which may be used as ligands include amines (primary, secondary, and tertiary) and aromatic amines, amino groups, amido groups, nitro groups, nitroso groups, amino alcohols, nitriles, imino groups, isonitriles, cyanates, isocynates, phosphates, phosphonates, phosphites, (substituted) phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls, and sulfinyls.

In yet other embodiments, the functional group may be an aryl group, alkenyl group, alkynyl group or other moiety which may bind the metal atom in either a σ- or π-coordinated fashion.

As a further illustration, exemplary ligands include bifunctional compounds such as amino acids, hydroxy acids, hydroxy thiols, mercapto amines, and the like. Other exemplary modular components include nucleic acids and nucleic acid analogs and derivatives, diacids, diamines, and the like.

If desired, one functionality of a ligand may be selectively protected or blocked to permit reaction of an unblocked functional group. Thus, for example, amino acid ligands may be blocked and deblocked according to known procedures for selective peptide synthesis. After coordination to the metal ion, the ligand may be modified, e.g., capped or blocked to prevent further reaction. Alternatively, a ligand may be so modified in vivo.

Other suitable structural moieties include the following Lewis base functionalities: arsine, stilbines, thioethers, selenoethers, teluroethers, thioketones, imines, phosphinimine, pyridines, pyrazoles, imidazoles, furans, oxazoles, oxazolines, thiophenes, thiazoles, isoxazoles, isothrazoles, amides, alkoxy, aryoxy, selenol, tellurol, siloxy, pyrazoylborates, carboxylate, acyl, amidates, triflates, thiocarboxylate and the like.

Other suitable ligands include structural moieties that are bidentate ligands, including diimines, pyridylimines, diamines, imineamines, iminethioether, iminephosphines, bisoxazoline, bisphosphineimines, diphosphines, phosphineamine, salen and other alkoxy imine ligands, amidoamines, imidothioether fragments and alkoxyamide fragments, and combinations of the above ligands.

Still other suitable ligands include tridentate ligands, including 2,5-diiminopyridyl ligands, tripyridyl moieties, triimidazoyl moieties, tris pyrazoyl moieties, and combinations of the above ligands.

Other suitable ligands include amino acids or comprise oligopeptides and the like.

Any of the ligands used in the present invention be substituted in a manner that does not materially interfere with their use as contemplated by the present invention.

Tethers

The therapeutic agents defined previously may either be directly attached to the metal center or attached to the metal center through a tether. Direct attachment is through a Lewis base functional group on the therapeutic agent. Later, when the subject coordination complex crosses the cell membrane, the surrounding environment induces release of the therapeutic agent. When the therapeutic agent is not coordinated directly to the metal center, a variety of tethers can be used to link the therapeutic agent to the metal center. Generally, the tether is a hydrocarbon chain of various possible lengths containing at least one functional group which allows for release of the therapeutic agent under the right conditions. Functional groups which can be used in tethers include ester, amide, amine, and anhydride moieties. In one embodiment of the present invention it is envisioned that the release rate of the therapeutic agent can be adjusted by modifying the nature, i.e. the type of functional group or carbon chain length, of the tether.

As a non-limiting example of a coordination complex comprising a suitable tether, the Pt(IV) complex (2) developed by Kutikov may be used for coupling a therapeutic agent and/or a targeting moiety.

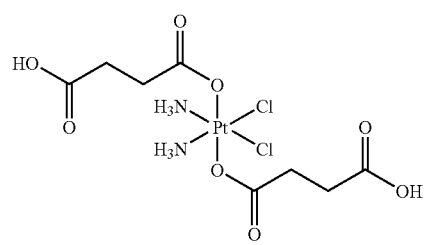

Complex 2 can be synthesized from cisplatin in an overall yield of 11% according to scheme 2.

Scheme 2.
Synthesis of complex 2.

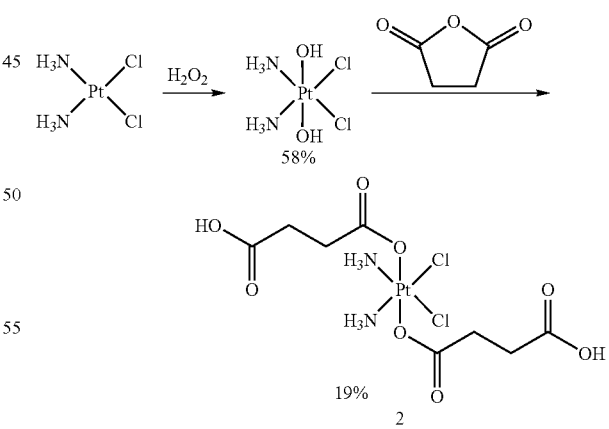

The yield for the succinic anhydride ring opening step was greatly improved to >60% by decreasing the amount of solvent (DMSO) as reported by Mukhopadhyay. The two carboxylic acids in 2 are used as handles to mono- and di-substituted platinum complexes with therapeutic agents and/or targeting moities.

Targeting Moieties

A number of targeting moieties known to those of skill in the art may be used in the subject coordination complexes.

Non-limiting examples of targeting moieties suitable for the subject coordination complexes of the present invention include peptides. The syntheses of the peptide sequences NGR—$NH_2$, $NH_2$CNGRC-GG (SEQ ID NO: 3) and RGD—$NH_2$ were performed by using an Advanced Chemtec batch peptide synthesizer. Scheme 3 depicts the automated steps taken for the synthesis of NGR—$NH_2$ but the same is applicable for the synthesis of any peptide sequence. A Rink amide resin was used as the solid support, which incorporates an $NH_2$ moiety to the C-terminus of the first loaded amino acid when the peptide is cleaved out of the resin, thus the obtained peptides contain an amide-capped C-terminus. The overall synthesis consists of coupling each the amino acids to either the Fmoc-deprotected resin or another amino acid by DIC/HOBt. In each case this is followed by the cleavage of the Fmoc on the coupled amino acid by piperidine (20%)/DMF.

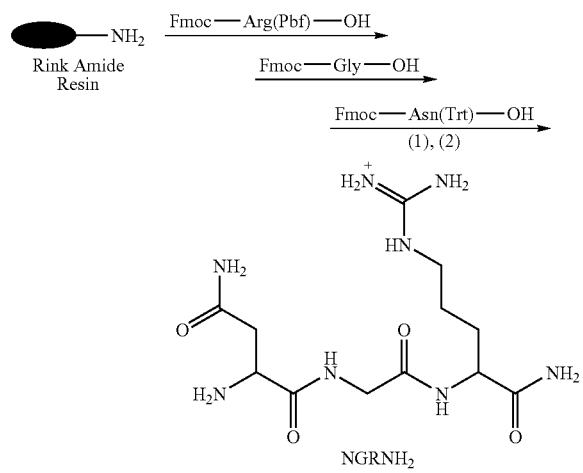

Scheme 3.
Solid phase NGR-$NH_2$ synthesis.

Automated synthetic steps: (1) DIC/HOBt, DMF, (2) 20% piperidine.

The synthesis of all three peptides was accomplished successfully based on the MALDI-TOF data summarized in Table 1.

TABLE 1

| Peptide | m/z observed | m/z calculated |
|---|---|---|
| NGR-$NH_2$ | 345.89 | 345.37 |
| $NH_2$CNGRC-GG (SEQ ID NO: 3) | 665.13 | 665.77 |
| RGD-$NH_2$ | 346.94 | 346.36 |

The purification of the peptide containing two cysteins proved to be difficult, thus isolation of the pure product was not pursued at this point. Additionally, the fact that sulfur atoms are known to strongly coordinate platinum may complicate the coupling step to the complex.

Figure 7:
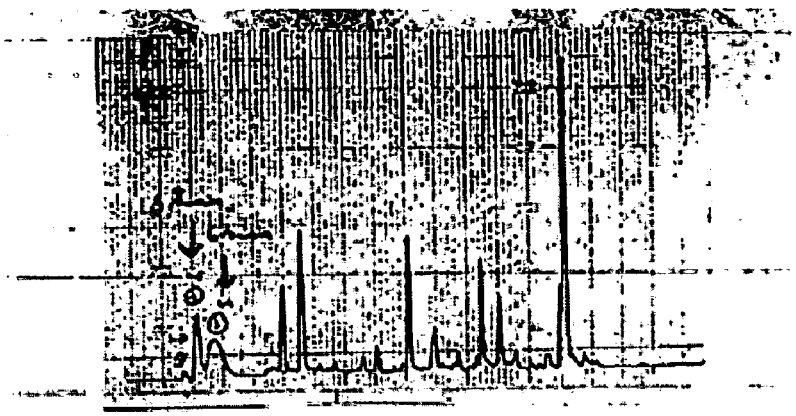
FIG. 7 depicts an HPLC chromatograph for purified NGR—$NH_2$.
Figure 8:
FIG. 8 depicts an HPLC chromatograph for purified RGD—$NH_2$.
Figure 9:
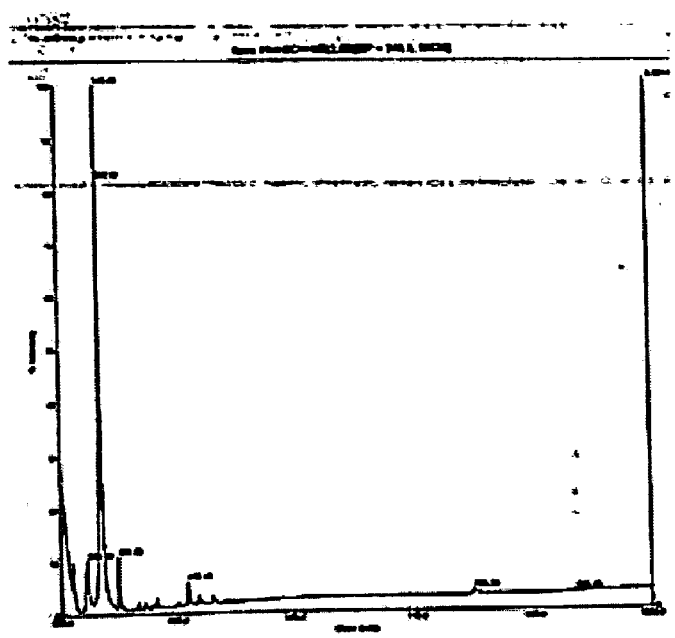
FIG. 9 depicts a mass spectrum for purified NGR—$NH_2$.
Figure 10:
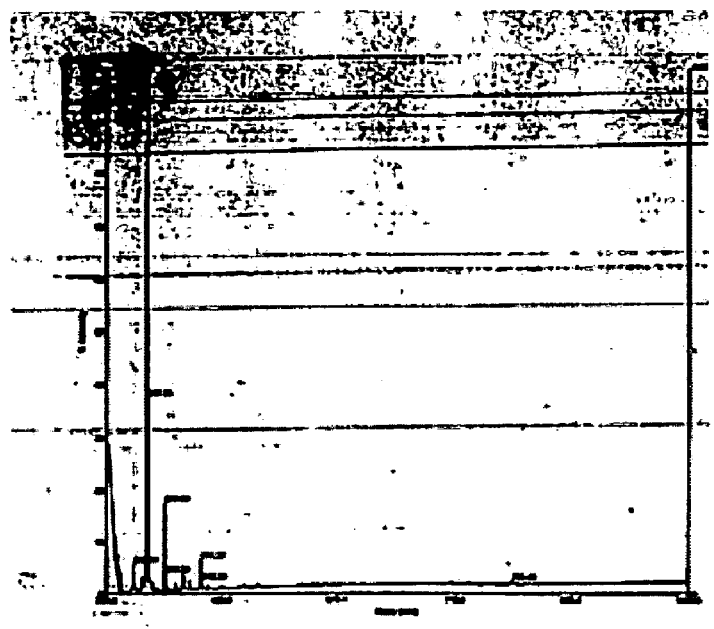
FIG. 10 depicts a mass spectrum for purified NGD—$NH_2$.

The purification of the NGR—$NH_2$ and RGD—$NH_2$ peptides by C18-HPLC was successful. For each peptide two peaks were collected from the HPLC (FIGS. 7 and 8) which corresponded to products with the desired mass (FIGS. 9 and 10). For NGR—$NH_2$, the collected peaks had retention times of 4.8 and 6.4 minutes and for RGD—$NH_2$, 4.8 and 5.6 minutes.

Figure 11:
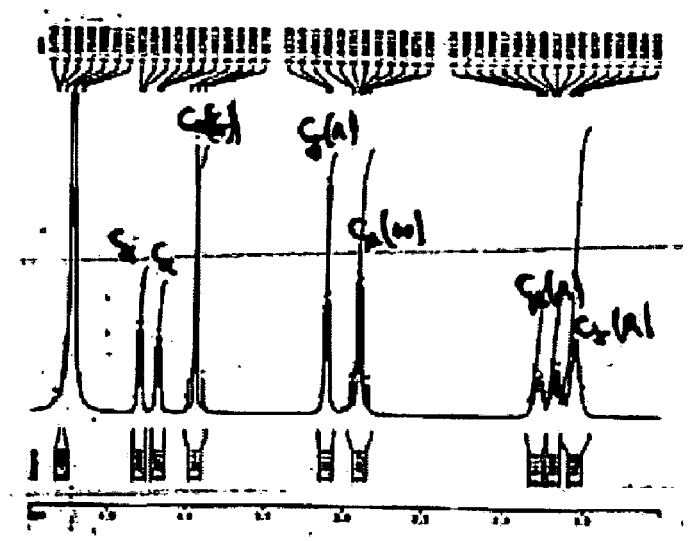
FIG. 11 depicts an $^1H$ NMR spectrum in $D_2O$ of a collected HPLC peak for NGR—$NH_2$.
Figure 12:
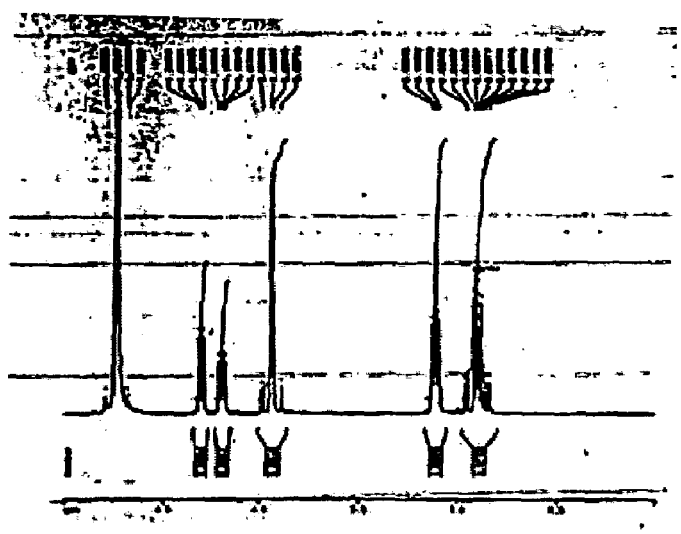
FIG. 12 depicts depicts an $^1H$ NMR spectrum in $D_2O$ of a collected HPLC peak for NGR—$NH_2$.

The $^1$H— and $^{13}$C-NMR spectra in $D_2O$ of both collected peaks for NGR—$NH_2$ were recorded in order to see if they correspond to the same isomer. The only difference in the $^1$H-NMR spectrum was the signal corresponding to the $C_\beta$—H of Asn, which only for the peak collected at 6.4 minutes was resolved as two sets of doublets (FIGS. 11 and 12).

Figure 13:
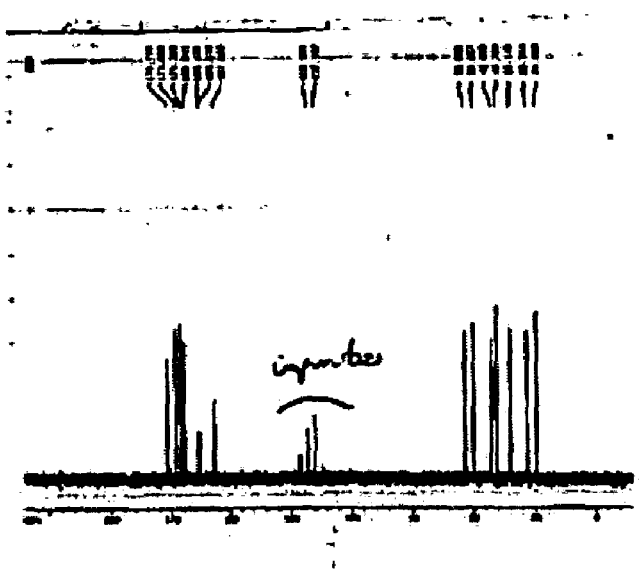
FIG. 13 depicts the $^{13}C$-NMR spectrum for the HPLC peak collected at 6.4 minutes for NGR—$NH_2$ showing some impurities at ~163 and 117 ppm.

Additionally, the $^{13}$C-NMR spectrum for the peak collected at 6.4 minutes showed some impurities at ~163 and 117 ppm which appear slightly in the peak collected at 5.6 minutes (FIG. 13). Based on these results one possible explanation may be that the detected impurities may become trapped in the peptide leading to a partial folding. NMR studies for the peptide RGD—$NH_2$ were not pursued but it is believed to behave similarly.

Other suitable peptide targeting moieties are listed in Table 2 along with the corresponding targeted organ.

TABLE 2

Peptide targeting moieties and the organ targeted.

| Peptide Sequence | Organ |
|---|---|
| GGG | Bone marrow |
| GFS | Bone marrow |
| LWS | Bone marrow |
| ARL | Bone marrow |
| FGG | Bone marrow |
| GVL | Bone marrow |
| SGT | Bone marrow |
| EGG | Fat |
| LLV | Fat |
| LSP | Fat |
| EGR | Fat |
| FGV | Fat |
| LVS | Muscle |
| GER | Muscle |
| AGG | Prostate |
| EGR | Prostate |
| GER | Prostate |
| GVL | Prostate |
| SMSIARL (SEQ ID NO: 4) | Prostate |
| GRR | Skin |
| GGH | Skin |

TABLE 2-continued

Peptide targeting moieties and the organ targeted.

| Peptide Sequence | Organ |
| --- | --- |
| GTV | Skin |
| ARL | Skin |
| FGG | Skin |
| FGV | Skin |
| SGT | Skin |
| GVL | Multiple Organs |
| EGR | Multiple Organs |
| GFG | Multiple Organs |
| FGV | Multiple Organs |
| GFGV (SEQ ID NO: 5) | Multiple Organs |
| RFGG (SEQ ID NO: 6) | Multiple Organs |
| FGGS (SEQ ID NO: 7) | Multiple Organs |
| FGGSV (SEQ ID NO: 8) | Multiple Organs |
| FGGSW (SEQ ID NO: 9) | Multiple Organs |
| FGG | Multiple Organs |
| GERIS (SEQ ID NO: 10) | Multiple Organs |
| GERLS (SEQ ID NO: 11) | Multiple Organs |
| GERAG (SEQ ID NO: 12) | Multiple Organs |
| GER | Multiple Organs |
| PSGTS (SEQ ID NO: 13) | Multiple Organs |
| MSGTG (SEQ ID NO: 14) | Multiple Organs |
| VSGT (SEQ ID NO: 15) | Multiple Organs |
| LSGT (SEQ ID NO: 16) | Multiple Organs |
| ISGT (SEQ ID NO: 17) | Multiple Organs |
| SGT | Multiple Organs |
| NGR | Atherosclerosis |
| RGD | Atherosclerosis |
| CGFECVRQCPERC (SEQ ID NO: 18) | Lung |

All the above peptide sequences are organ specific moieties proposed for the targeted delivery of platinum complexes to carcinogenic tumors. All are recognized by vascular receptors. The NGR and RGD moieties, are also markers for atherosclerosis. These peptides are recognized by integrins, aminopeptidase N/CD13 and membrane dipeptidase. Check also Arap, W. Nature Medicine, February 2002, 8(2), page 125, Table 2, for a detailed description of the proteins that these peptides mimic.

In addition to peptides, other types of targeting moieties known in the art may be used to direct the cisplatin, with or without a therapeutic agent present in the coordination complex, to the targeted tumor cells. Non-limiting examples of additional targeting moieties include vitamins such as folic acid, vitamin $B_{12}$ (cobalamin, Cbl, or $VB_{12}$), riboflavin, and biotin. It will be understood that derivatives and analogs of vitamins are also within the scope of the present invention. Other non-limiting examples include peptidomimetics, which mimic the activity of a peptide; or a protein such as antibody or a growth factor receptor or a fragment thereof such as an Fv, single chain Fv(scFv), Fd or Fab fragment of an antibody, which contains a binding domain; cells including smooth muscle cells, leukocytes, B-lymphocytes, T-lymphocytes, monocytes, macrophages, foam cells, platelets, granulocytes, neutophilis, heme, porphoryns, and phthalocyanines; chemotactic proteins and peptides including monocyte chemotactic protein 1 (MCP-1), N-formyl-methionyl-leucyl-phenalanine; colony stimulating factors including GM-CSF, CSF-1, and receptors and antibodies thereto and platelet factor 4; growth factors including TGF-β and VEGF; adhesive cell-surface glycoproteins including E-selectin, VCAM-1, and VCAM1β; carbohydrates including $^{11}C$-deoxy-D-glucose, and $^{18}F$-2-fluorodeoxy-D-glucose; interleukins including IL-1, IL-1α, IL-1β, IL-2, IL-3, IL-6, IL-7, and IL-8; interferons including interferon α and interferon γ; tumor necrosis factor TNF-α; and lipids including liposomes, polyethylene glycol coated liposomes, cholesterol, esters of cholesterol, lipoproteins selected from the group consisting of LDL, HDL, oxidized LDL, and lipid receptors.

Platinum Containing Coordination Complexes

A. Platinum Containing Coordination Complexes Comprising Therapeutic Agents

Synthesis and Characterization of Various Platinum Containing Coordination Complexes (BEP1-5)

The syntheses of several subject coordination complexes comprising estrogen as the therapeutic agent tethered to a platinum(IV) metal ion are set forth below. As described above in Scheme 1 (and without limitation), the reducing environment of the cell is expected to convert those coordination complexes to cisplatin and tether-modified estrogen. The tethers contained in the therapeutic agent for these subject coordination complexes were designed to be susceptible to hydrolysis by intracellular esterases, which is expected to give rise to free estrogen.

Figure 2:
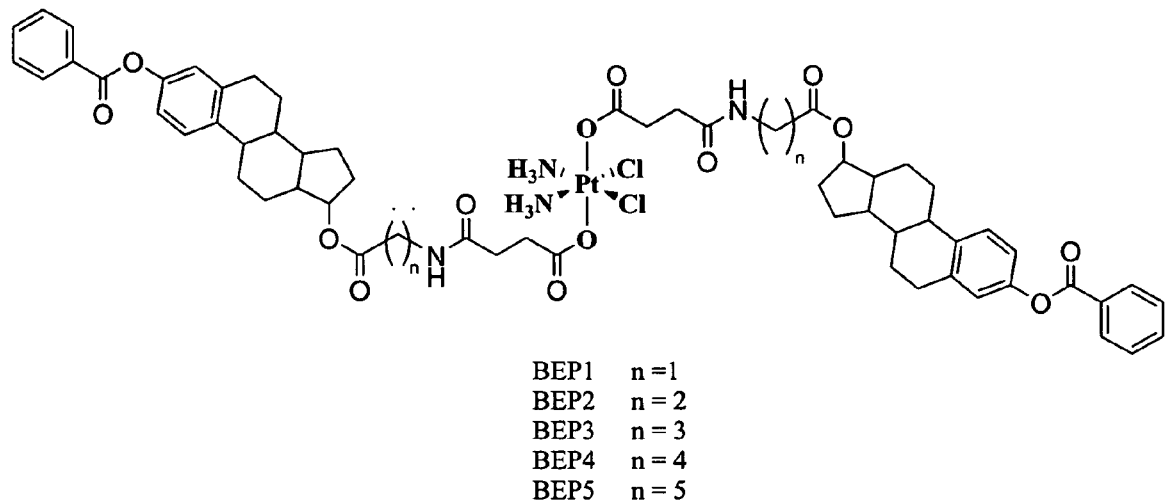
FIG. 2 depicts BEP1-5.

The subject coordination complexes shown in FIG. 2 were prepared by first preparing the tether-modified estrogen molecules shown in FIG. 1. (The various identifiers for those coordination compounds are provided in FIG. 2.) Synthesis of BEP1, was achieved in ~30% yield (Scheme 4).

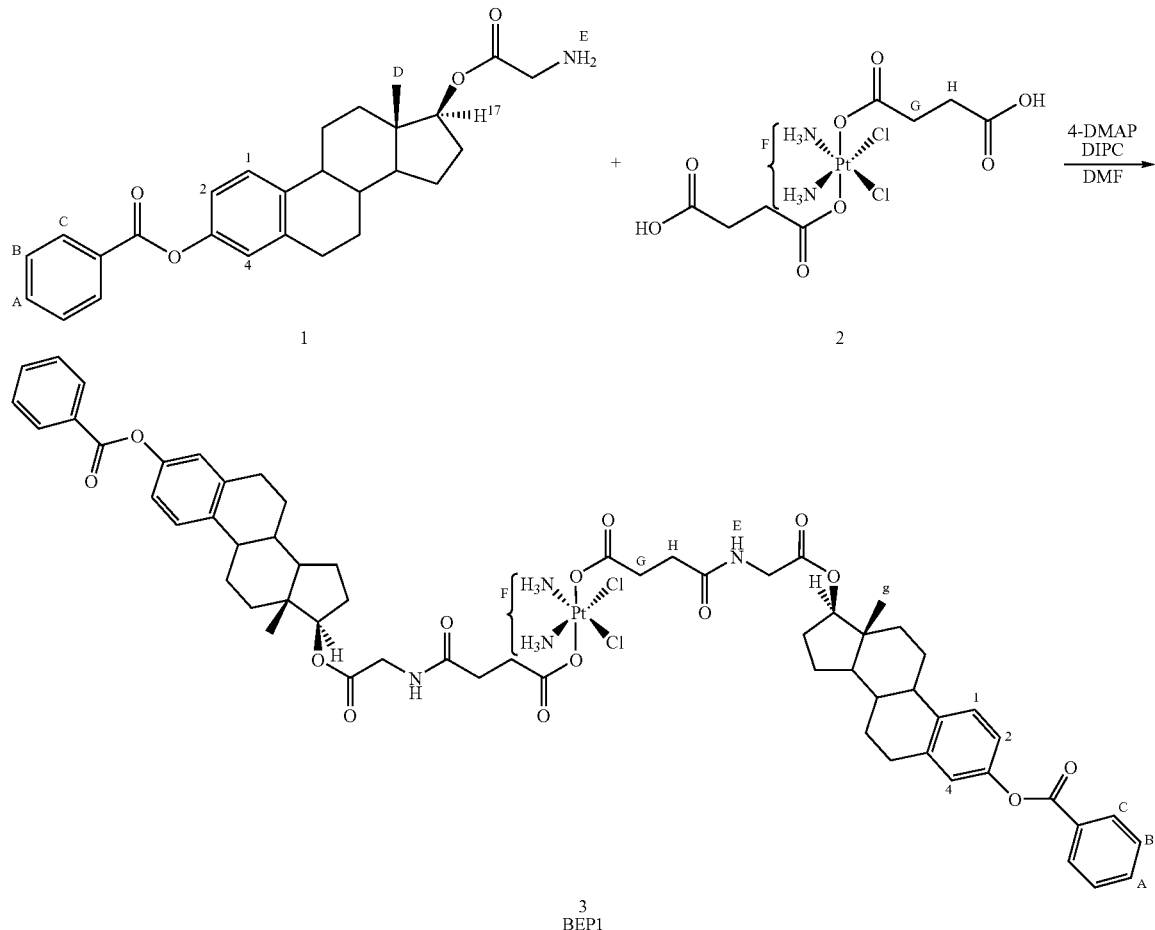

Scheme 4.
Synthesis and ¹H NMR proton designations for BEP1.

The series of tether-modified estrogens shown in FIG. 1 were obtained by coupling estradiol-3-benzoate and BOC-protected-amino-alkyl carboxylic acids using diisopropyl-carbodiimide (DIPC), followed by removal of the BOC-protecting group. Formation of the desired tether-modified estrogens were confirmed by ESI-MS and ¹H NMR (Table2). Formation of the new ester tether is supported by a significant downfield shift of the $H_{17}$ proton resonance. In addition, the amine protons ($H_E$) are observed as a broad singlet at 1.75 ppm. In addition, the integrated intensity of the $H_E$ protons is the same as the integrated intensity of the $H_B$ and $H_C$ aromatic protons.

TABLE 2

¹H NMR data (ppm) for the estrogen ligand and platinum complexes[a]

| | $H_A$ | $H_B$ | $H_C$ | $H_D$ | $H_E$ | $H_F$ | $H_G$ | $H_H$ | $H_1$ | $H_2$ | $H_4$ | $H_{17}$ |
|---|---|---|---|---|---|---|---|---|---|---|---|---|
| 1[b] | | | | | | 6.51 bs, 6H | 2.53 t, 4H | 2.45 t, 4H | | | | |
| EL1[c] | 7.74 t, 1H | 7.59 t, 2H | 8.12 d, 2H | 0.796 s, 3H | 1.75 s, 2H | | | | 7.34 d, 1H | 7.01 d, 1H | 6.96 s, 1H | 4.66 t, 1H |
| EL2[c] | 7.73 t, 1H | 7.58 t, 2H | 8.09 d, 2H | 0.814 s, 3H | 1.75 s, 2H | | | | 7.32 d, 1H | 7.00 d, 1H | 6.94 s, 1H | 4.67 t, 1H |
| EL3[c] | 7.73 t, 1H | 7.59 t, 2H | 8.09 d, 2H | 0.813 s, 3H | 1.70 s, 2H | | | | 7.33 d, 1H | 7.00 d, 1H | 6.95 s, 1H | 4.65 t, 1H |
| EL4[c] | 7.73 t, 1H | 7.59 t, 2H | 8.09 d, 2H | 0.815 s, 3H | 1.70 s, 2H | | | | 7.32 d, 1H | 7.00 d, 1H | 6.95 s, 1H | 4.65 t, 1H |
| EL5[c] | 7.72 t, 1H | 7.58 t, 2H | 8.08 d, 2H | 0.798 s, 3H | 1.70 s, 2H | | | | 7.32 d, 1H | 7.00 d, 1H | 6.93 s, 1H | 4.62 t, 1H |
| BEP1[d] | 7.74 t, 2H | 7.59 t, 4H | 8.10 d, 4H | 0.785 s, 6H | 8.33 t, 2H | 6.56 bs, 6H | 2.49 t, 4H | 2.36 t, 4H | 7.34 d, 2H | 7.01 d, 2H | 6.945 s, 2H | 4.65 t, 2H |

TABLE 2-continued $^1$H NMR data (ppm) for the estrogen ligand and platinum complexes[a]

| | $H_A$ | $H_B$ | $H_C$ | $H_D$ | $H_E$ | $H_F$ | $H_G$ | $H_H$ | $H_1$ | $H_2$ | $H_4$ | $H_{17}$ |
|---|---|---|---|---|---|---|---|---|---|---|---|---|
| BEP2[d] | 7.74 | 7.60 | 8.10 | 0.799 | 7.95 | 6.49 | 2.47 | 2.28 | 7.35 | 7.00 | 6.95 | 4.65 |
| | t, 2H | t, 4H | d, 4H | s, 6H | t, 2H | bs, 6H | m, 4H | t, 4H | d, 2H | d, 2H | s, 2H | t, 2H |
| BEP3[d] | 7.74 | 7.59 | 8.10 | 0.805 | 7.85 | 6.50 | 2.47 | 2.2 | 7.35 | 7.00 | 6.96 | 4.69 |
| | t, 2H | t, 4H | d, 4H | s, 6H | t, 2H | bs, 6H | m, 4H | t, 4H | d, 2H | d, 2H | s, 2H | t, 2H |
| BEP4[d] | 7.74 | 7.60 | 8.10 | 0.804 | 7.85 | 6.51 | 2.43 | 2.2 | 7.35 | 7.00 | 6.97 | 4.64 |
| | t, 2H | t, 4H | d, 4H | s, 6H | t, 2H | bs, 6H | m, 4H | t, 4H | d, 2H | d, 2H | s, 2H | t, 2H |
| BEP5[d] | 7.71 | 7.57 | 8.09 | 0.799 | 7.81 | 6.49 | 2.42 | 2.2 | 7.32 | 6.98 | 6.94 | 4.62 |
| | t, 2H | t, 4H | d, 4H | s, 6H | t, 2H | bs, 6H | m, 4H | t, 4H | d, 2H | d, 2H | s, 2H | t, 2H |

[a]See Scheme 4 for atom labeling diagram.
[b]Compound 1 refers to the platinum-succinato compound (see Scheme 4, compound 2, for atom labeling diagram).
[c]EL1–EL5 refer to the tether-modified estrogen.
[d]BEP1–BEP5 refer to the estrogen-linked platinum compounds.

Cisplatin is readily oxidized by hydrogen peroxide to obtain cis, cis, trans-diamminedichlorodihydroxoplatinum (IV). The trans-dihydroxyplatinum(IV) complex can be further modified upon reaction with succinic anhydride to yield a trans-dicarboxylatoplatinum(IV) complex. Both ESI-MS and $^1$H NMR (Table2) were used to characterize cis, cis, trans-diamminedichlorodisuccinatoplatinum(IV). The platinum-ammine proton resonance occurs as a broad singlet at 6.51 ppm, which is consistent the ammine chemical shifts of other trans-dicarboxylatoplatinum(IV) complexes. The succinato protons ($H_G$ and $H_H$) and ammine protons ($H_F$) integrate with a 4:3 ratio, indicating there are two succinato ligands per platinum center.

The amine-modified estrogens are coupled to the trans-dicarboxylatoplatinum(IV) complex utilizing diisopropylcarbodiimide, a common peptide coupling reagent. The ESI-MS and $^1$H NMR data (Table 2) confirm the presence of the desired estrogen-tethered platinum(IV) complexes. The coupling of the series of modified-estrogen species to cis, cis, trans-diamminedichlorodisuccinatoplatinum(IV) yield amide-tethered species. Formation of the amide bond is evident from the loss of the free amino $NH_2$ proton resonances at 1.70–1.75 ppm and the appearance of amide proton resonances at 7.8–8.33 ppm ($H_E$). The $^1$H NMR data provide quantitative evidence for the presence of two estrogen moieties for every one platinum center. The integrated intensity of the methyl protons ($H_D$) of the two estrogen moieties match that of the platinum-ammine protons ($H_F$). In addition, there are an equal number of amide protons ($H_E$) and estrogen 17-α-protons ($H_{17}$). The experimentally determined mass was in excellent agreement with the calculated value (±0.003%). The synthetic strategy presented provides a new method for preparing potential platinum(IV) anticancer prodrugs and has the potential to target such complexes to specific cell or tissue types.

HMGB1 Upregulation Induced by BEP

Figure 3:
FIG. 3 depicts immunofluorescence microscopy data. MCF-7 cells treated either with estrogen or BEP have upregulated levels of HMGB1, as exhibited by the increase in both nuclear and cytoplasmic staining. Cells treated with [2] have dull nuclei and dark cytoplasms, indicating no increase in HMGB1 synthesis.
Figure 3:
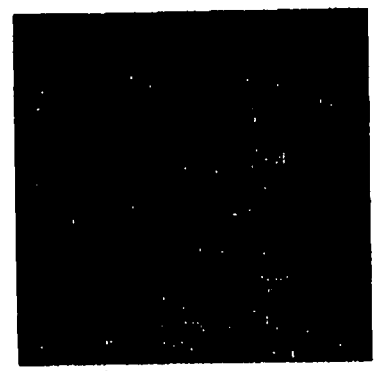
Figure 3:
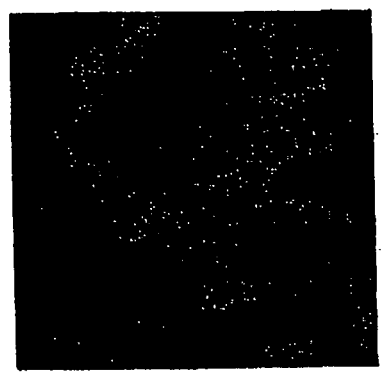
Figure 3:
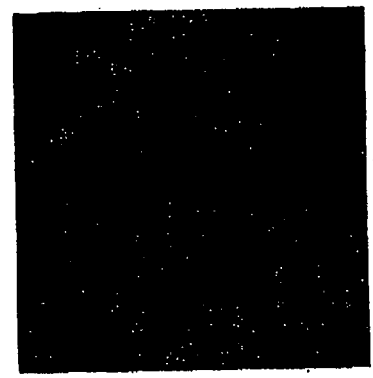
Figure 6:
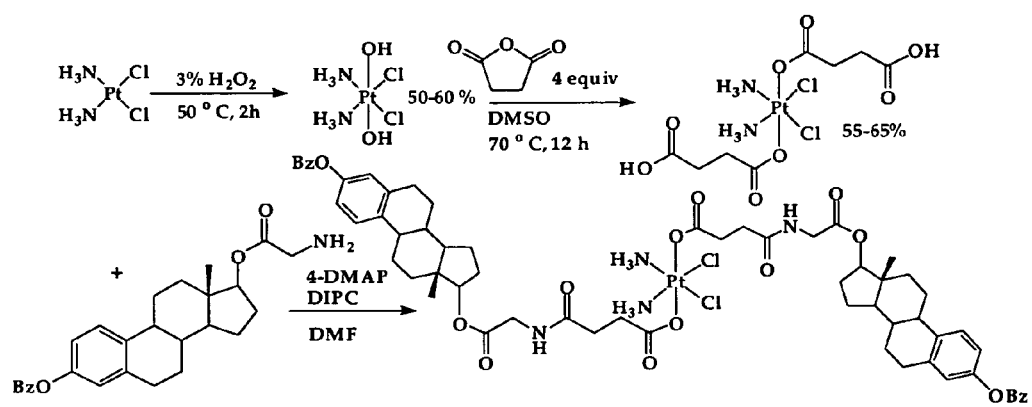
FIG. 6 depicts the synthesis of BEP and upregulated levels of HMGB1.
Figure 6:
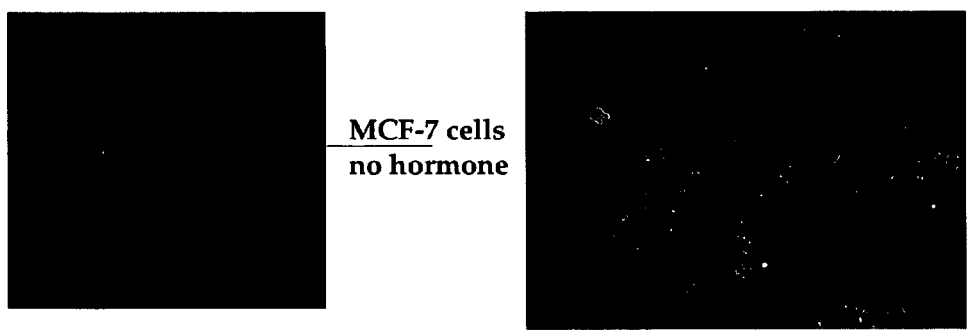

As discussed earlier, estrogen sensitizes ER(+) cells to cisplatin by inducing overexpression of HMGB1, a protein that is believed to shield cisplatin-DNA adducts from NER. In order for ER(+) cells to be more sensitive towards BEP treatment than ER(−) cells, BEP itself must be able to induce HMGB1 upregulation. Immunofluorescence microscopy was utilized to visualize cellular levels of HMGB1 in ER (+) MCF-7 cells. The MCF-7 cells were treated with either DMF (control), estrogen, cis, cis, trans-diamminedichloro-disuccinatoplatinum(IV) (2) or BEPn. As shown in FIGS. 3 and 6, MCF-7 cells treated only with DMF display an immunoresponse because there are between 10,000–100,000 copies of HMGB1 in a normal cell. We presently believe that the ability of a substance to upregulate HMGB1 levels can be evaluated by comparing the brightness of the treated cells to that of the untreated cells. Estrogen-treatment elevates these HMGB1 levels, as shown by increased fluorescence in both the nucleus and cytoplasm of the cell. Cells were treated with either 2 or BEP to determine whether the presence of a platinum cytotoxic agent effected cellular levels of HMGB1 after 2 hours. Cells that were treated with 2 did not have elevated levels of HMGB1; however, cells treated with BEP1 exhibit increased levels of fluorescence in the cytoplasm and nucleus, indicating an overexpression of HMGB1. BEP2 and BEP3 exhibited increased levels of fluorescence after 4 h of treatment. BEP4 and BEP5 displayed elevated immunoresponses after 6 h of treatment. The abilities of BEPn to upregulate HMGB1 suggest that ER (+) cells should be more sensitive to BEP than are ER (−) cells.

We presently believe that results demonstrated by immunofluorescence, that the kinetics of HMGB1 upregulation may be controlled by varying the estrogen-tether length. In order to interact with the estrogen receptor (or at least to increase the efficiency of the interaction), it is believed that the tether must first be hydrolyzed by intracellular esterases to afford unmodified β-estradiol. The rate of ester hydrolysis can be affected by both the length and nature of the tether.

Cytotoxicities of BEPn

Figure 4:
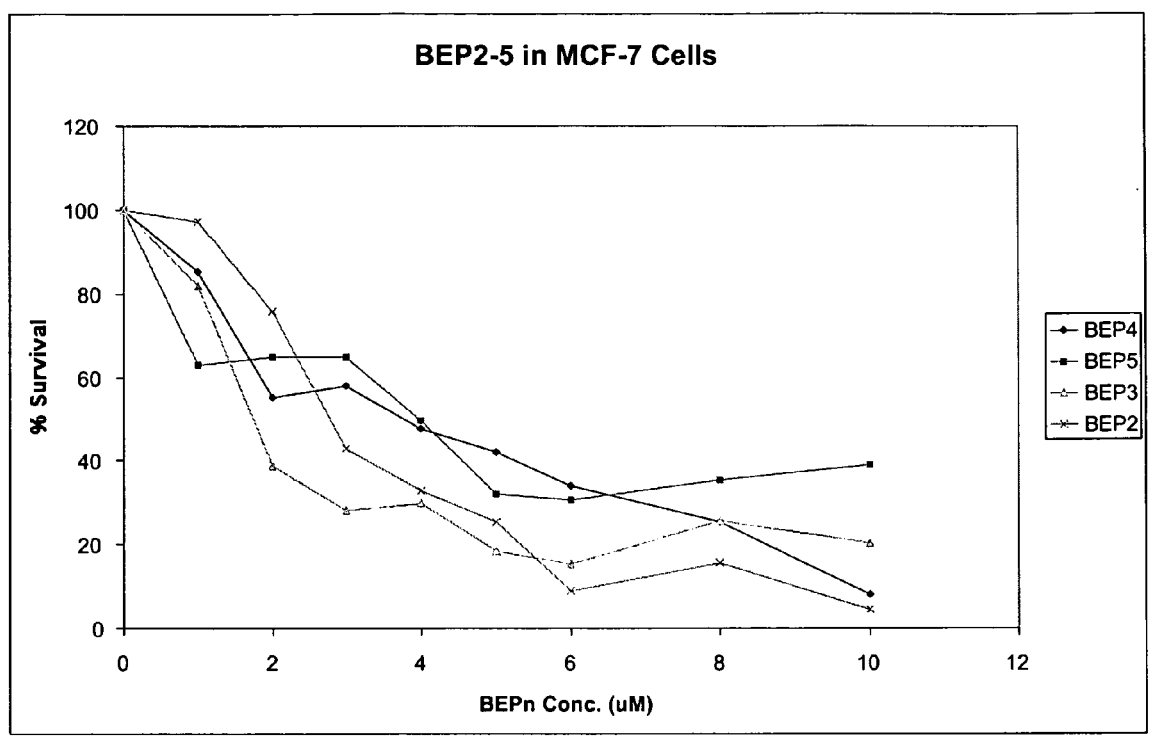
FIG. 4 depicts the cytotoxicity data for BEP in MCF-7 cells.
Figure 5:
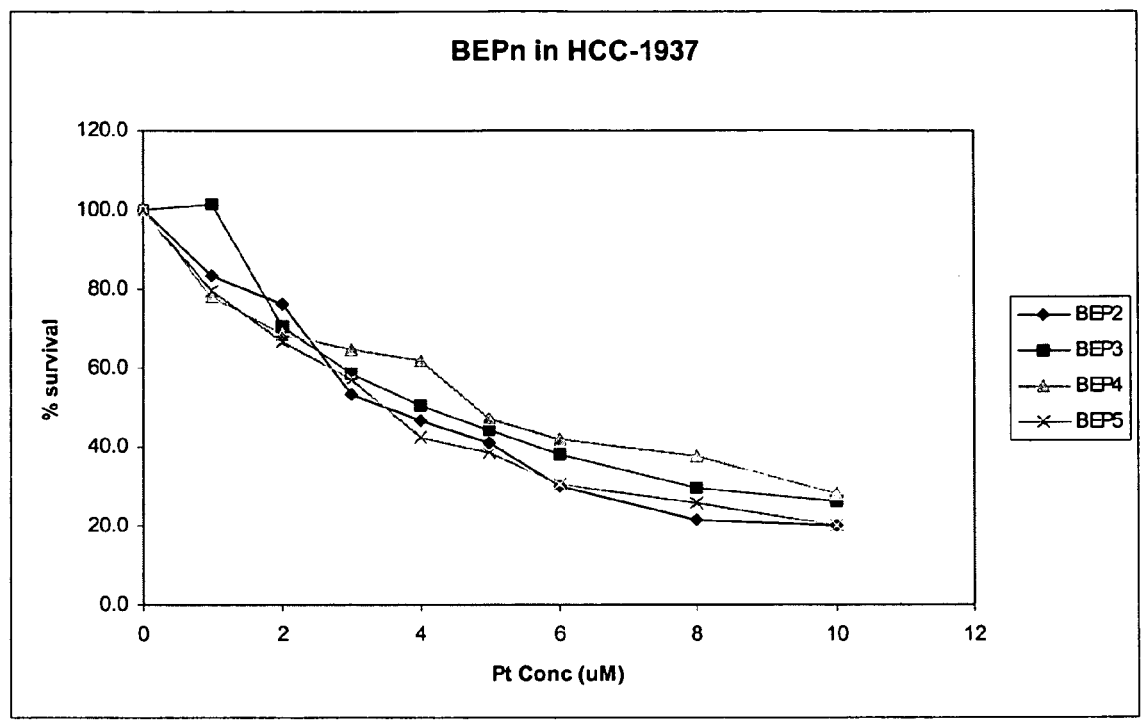
FIG. 5 depicts the cytotoxicity data for BEP in HCC-1937 cells.

The HCC-1937 cells were equally sensitive to BEP1-5 ($IC_{50}$(average)~3.7 µM). See FIGS. 4–5. As shown in Table 3, the cytotoxicities of BEP1-5 varied with linker-length in the MCF-7 cell line.

TABLE 3

Cytotoxicity data ($IC_{50}$) for BEP1–BEP5.

|  | MCF-7 | HCC-1937 |
| --- | --- | --- |
| BEP1 | 3.7 µM | 3.8 µM |
| BEP2 | 2.9 µM | 3.9 µM |
| BEP3 | 2.1 µM | 4.0 µM |
| BEP4 | 4.1 µM | 4.3 µM |
| BEP5 | 5.0 µM | 3.9 µM |

Compounds BEP1, BEP4, and BEP5 were similarly active in MCF-7 and HCC-1937 cell lines, indicating no HMGB1 upregulation-induced repair shielding. BEP2 was 1.3-fold more sensitive in MCF-7 cells. MCF-7 cells were 1.8-fold more sensitive than HCC-1937 towards BEP3. The differential toxicity in MCF-7 and HCC-1937 cells observed with BEP2 and BEP3 suggest that these compounds are able to upregulate HMGB1 and shield platinum-adducts from repair. These results also emphasize that the kinetics of estrogen-induced HMGB1 upregulation and cisplatin-DNA damage are crucial for sensitizing ER(+) cells to platinum treatment.

B. Platinum Containing Coordination Complexes Comprising a Peptide Targeting Moiety Platinum containing coordination complexes comprising a peptide targeting moiety were prepared by coupling a peptide described previously with complex 2 (Scheme 5). Complex 2 is soluble in DMF but only slightly in water. On the other hand the peptides are water-soluble, therefore a $H_2O/DMF$ mixture and the EDC/S-NHS coupling system was chosen for the coupling reaction.

The coupling in the presence of RGD—$NH_2$ did not produce the expected mono- and/or di-substituted adducts but an unidentified platinum complex with m/z of 690.2. The expected m/z for the mono- and di-substituted are 861.54 and 1188.88, respectively.

Scheme 5.
Synthesis of peptide containing cisplatin complex.

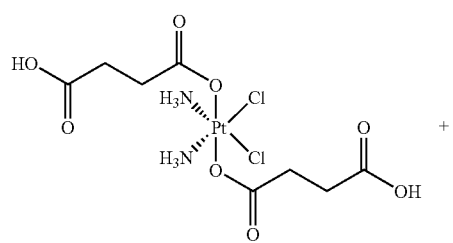

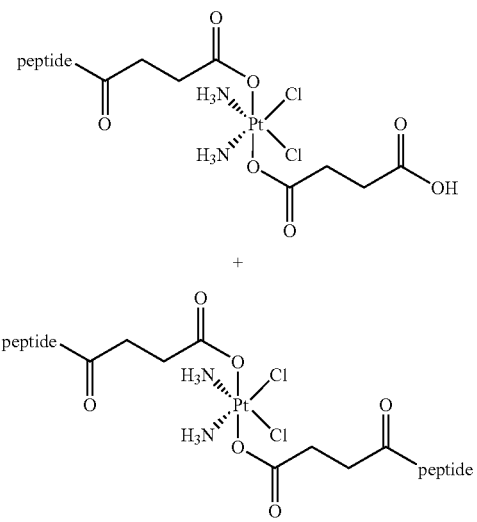

The isotopic pattern as well as the one mass unit difference in between each isotopic line points to a singly charged platinum complex, however, no conclusive chemical structure could be proposed. The non-protected Asp in the RGD—$NH_2$ peptide may have been activated during the coupling reaction leading to a non-desirable product. Thus, the protected Fmoc-Asp(ODmab)—OH amino acid was used in the synthesis of the RGD—$NH_2$ peptide. The Dmab protecting group is cleaved by 2% hydrazine in DMF allowing its specific cleavage while using TFA for the cleavage of the other protecting group. The MALDI-TOF analysis of the obtained product turned out to be that of Fmoc-Asp(ODmab)—OH (m/z (observ.)=666.13, m/z (calc.)=666.7). The calculated m/z for the expected RGD (Odmab)$NH_2$ peptide is 656.77. It is not clear at this point the cause for the failure of this reaction but the Fmoc on the Asp, which is the first amino acid to be loaded on the resin, was not cleaved thus impeding the elongation of the peptide chain. The RGD—$NH_2$ coupling approach wasn't pursued any longer but it is important to find a suitable procedure, which allows for the preparation of the RGD—$NH_2$ peptide containing the Asp side chain protected and for its cleavage under very mild acidic or basic conditions.

Figure 14:
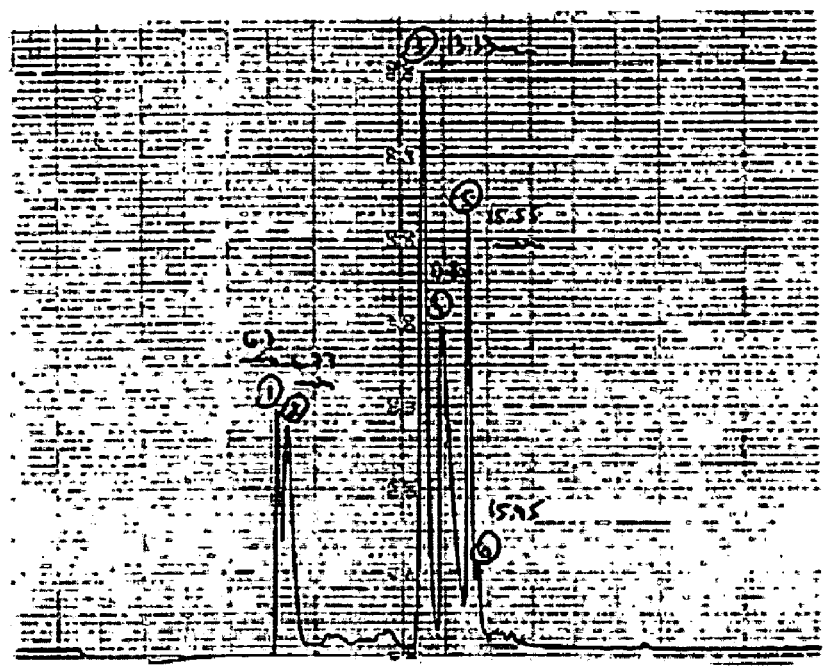
FIG. 14 depicts an HPLC chromatograph the mono- and di-substituted adducts SUN-M and SUN-D, respectively; the crude mixture was purified by C18-HPLC and peaks with retention times of 15.55 and 15.95 minutes are the two desired compounds.

The reaction in the presence of NGR—$NH_2$ produced the mono- and di-substituted adducts; the crude mixture was purified by C18-HPLC and peaks with retention times of 15.55 and 15.95 minutes are the two desired compounds (FIG. 14).

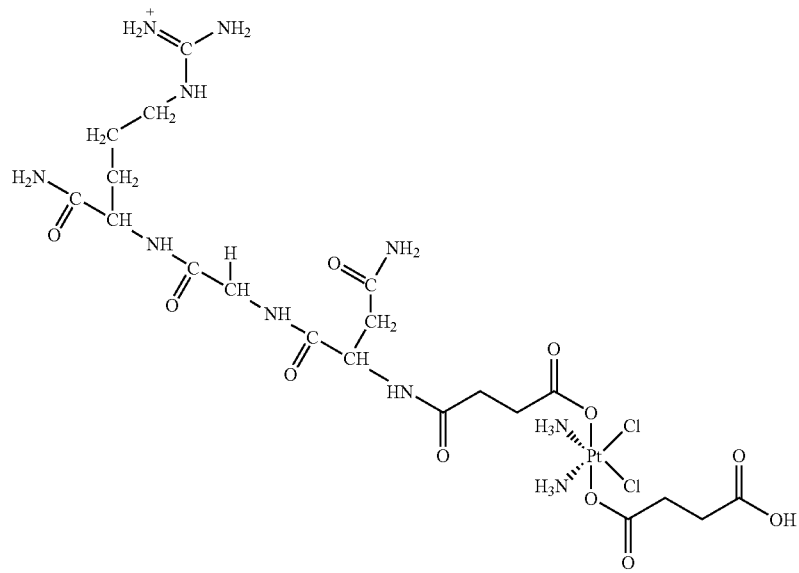
SUN-M
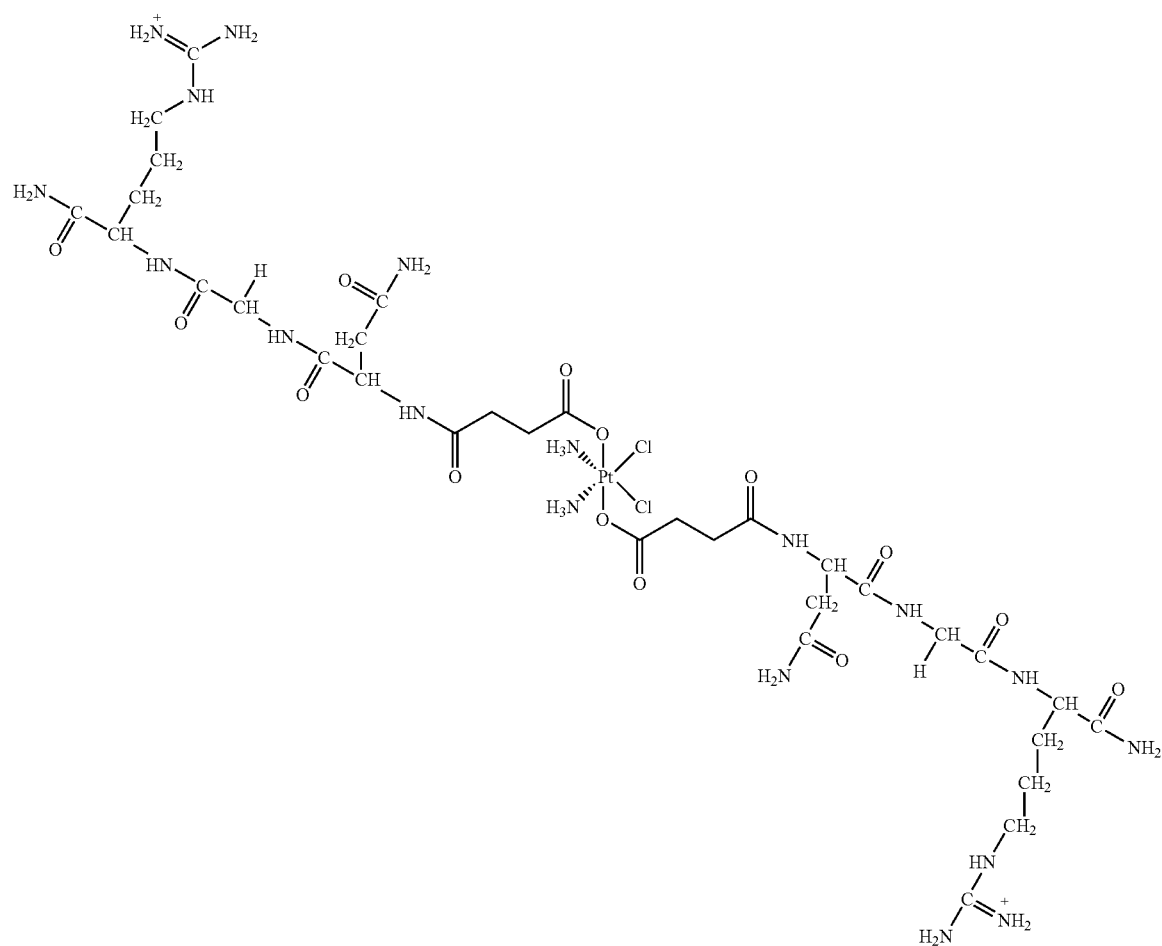
SUN-D

Figure 15:
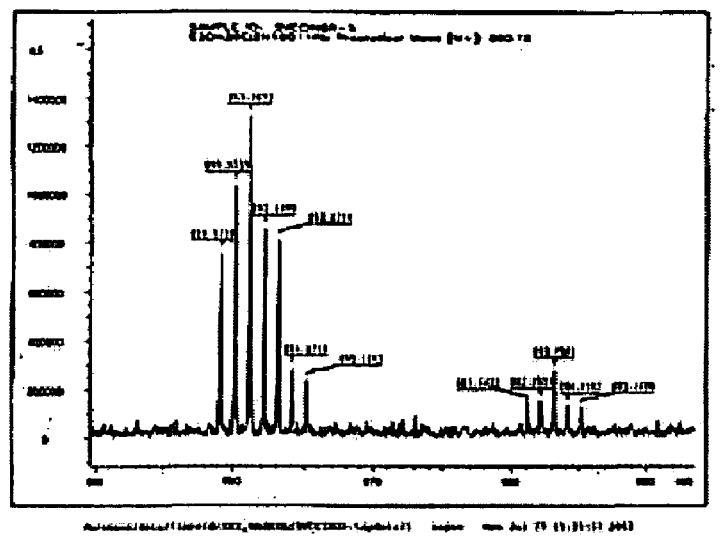
FIG. 15 depicts the mass spectrum for mon-substituted adduct SUN-M.
Figure 15:
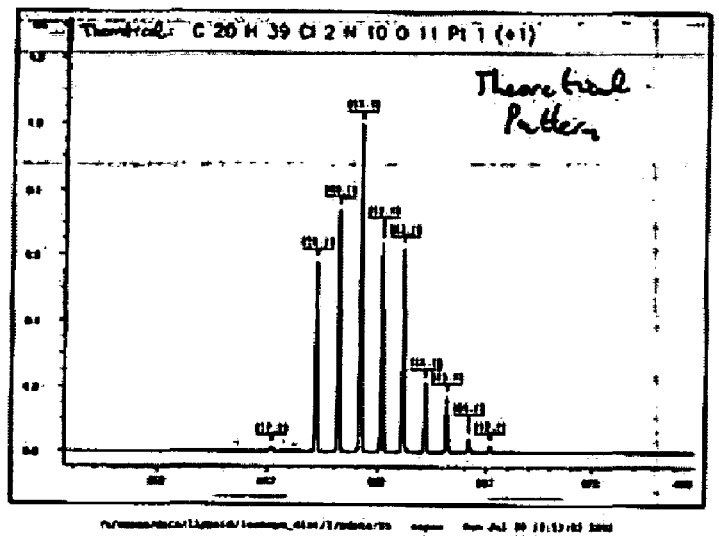

The mono-substituted compound is termed SUN-M (SUccinate platinum Ngr Monosubsituted) and the observed mass corresponds to a singly charged species (m/z (observ.) =860.17 [M+], 883.16 [M+Na]; m/z (calc.)=860.17 [M+]; FIG. 15).

Figure 16:
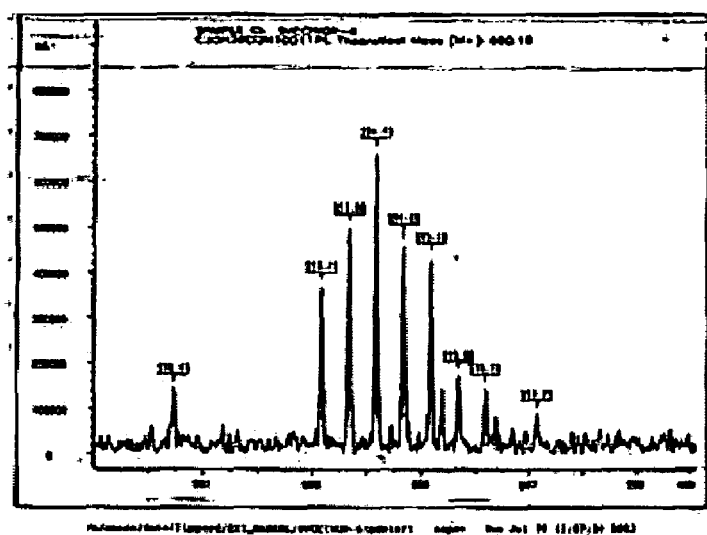
FIG. 16 depicts the mass spectrum for the di-substituted adduct SUN-D.
Figure 17:
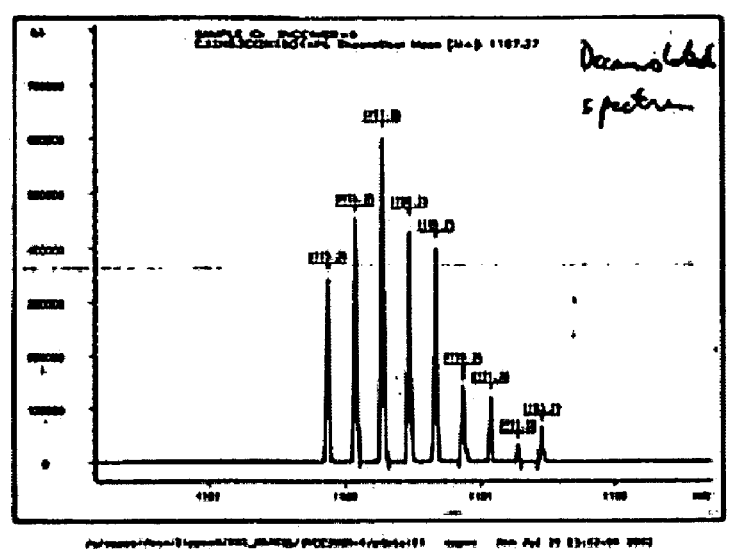
FIG. 17 depicts the deconvoluted mass spectrum of mono-substituted adduct SUN-M.

The Di-substituted complex termed SUN-D, however, appears as a doubly charged as can be clearly concluded from the half-mass unit difference in between each isotopic line (FIG. 16). The deconvolution of the spectrum (FIG. 17) is assigned to the singly charged species with an observed m/z of 1187.35 (m/z(calc.)=1187.37).

Figure 18:
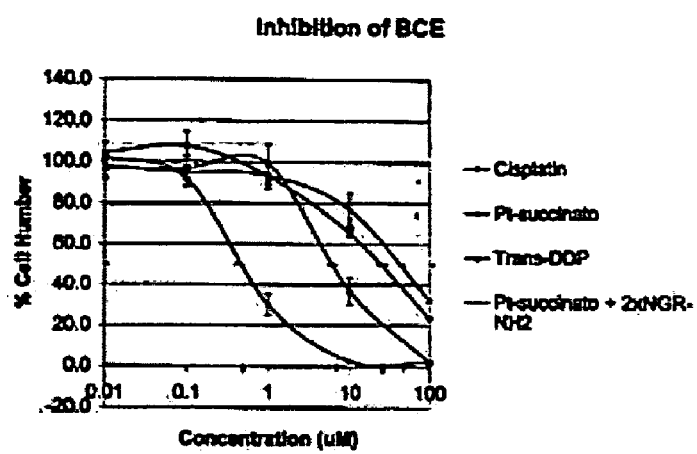
FIG. 18 depicts the results of an inhibition of BCE experiment for several standards as measured on a Coulter Counter.

In vitro activity studies of SUN-M and SUN-D on proliferating endothelial cells was pursued in collaboration with Carmen M. Barnés from the Folkman Group at The Children's Hospital Harvard Medical School. In the first phase of this project we have decided to analyze the compounds activity on Bovine Capillary Endothelial Cells (BCE). The first set of measurements were performed as control experiments, thus cisplatin, trans-DDP, complex 2 and complex 2 plus non-conjugated NGR—NH$_2$ were added at 0.01, 0.1, 1.0, 10 and 100 μM to 7,500 BCE cells in the presence of basic fibroblast growth factor (bFGF). The cell number percentage was counted after 72 hours on a Coulter Counter and it was found that the in vitro activity of complex 2 and complex 2 plus non-conjugated NGRNH$_2$ are comparable (FIG. 18). On the other hand, cisplatin was the most active among the four measured controls. It is important to point out that the percentage of non-induced cells (i.e. normal cells) was 44.8% after 72 hours. Therefore, as concluded from the results that are shown in FIG. 18, concentrations above 1.0 μM for cisplatin, 10 μM for trans-DDP and 100 μM for complex 2 are toxic also to non-induced proliferating cells.

Figure 19:
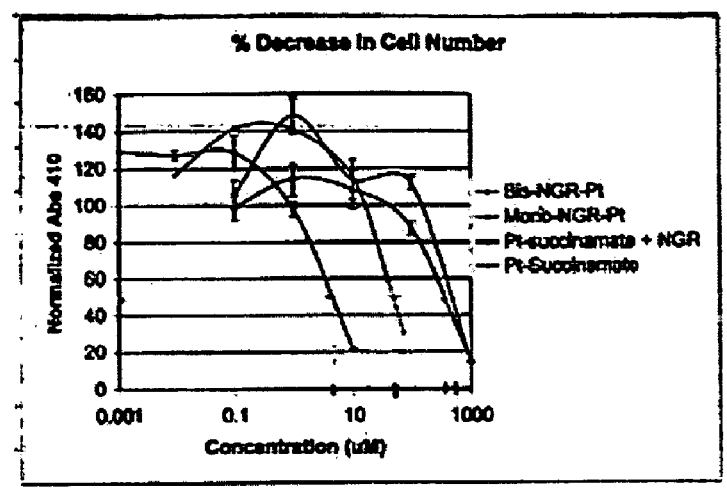
FIG. 19 depicts the decrease in cell number percentages for SUN-M and SUN-D as measured by the cell-counting procedure.

The in vitro activity measurements for SUN-M and SUN-D were first performed with a colorimetric assay, which uses the acid phosphatase enzymes to catalyze the hydrolysis of monophosphate esters (R—O—P(O)(OH)$_2$) to inorganic phosphate (Pi) and an alcohol (R—OH). The optimum pH for acid phosphatases is usually much below pH 7.0. A 5.0 or 5.5 buffer was used in the present reaction. P-nitrophenyl phosphate is hydrolyzed to p-nitrophenol which is yellow and absorbs at 410 nm. This method was not as accurate as the cell-counting procedure and this can also be concluded from the results shown in FIG. 19.

At 100 μM concentration of complex 2, most of the cells are intact. At the same concentration using a Coulter Counter only 20% of the cells are still alive. Although the colorimetric measurements are not comparable to those performed by the counting method the trend is clear and it is concluded that both SUN-M and SUN-D complexes are more active than complex 2. Based on these measurements SUN-D is more active than SUN-M by ~10-fold. One possible explanation may be a synergetic effect created from the interaction of each attached peptide in SUN-D with two neighboring cell-surface receptors.

Figure 20:
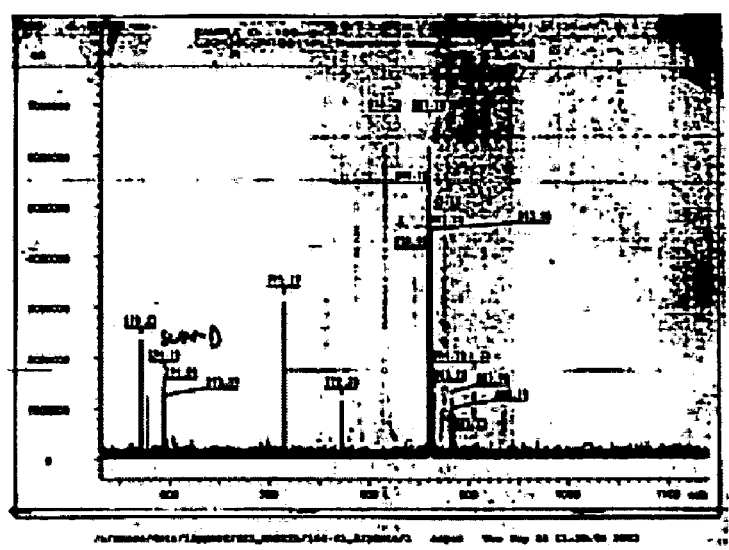
FIG. 20 depicts the mass spectrum of a mixture (S1) of SUN-M and SUN-D.

The purification of an additional batch of the coupled-peptide complexes was not as successful as described above, thus a mixture of the complexes SUN-M and SUN-D was obtained (FIG. 20).

Figure 21:
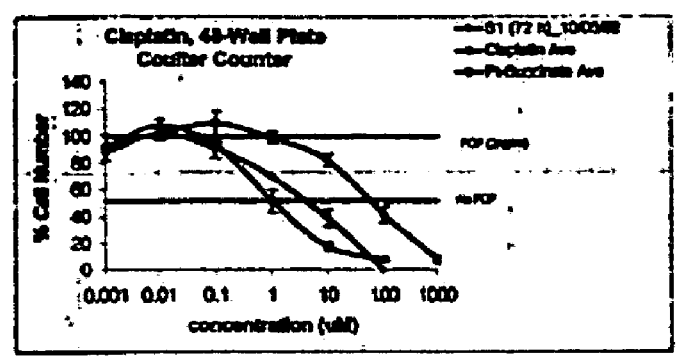
FIG. 21 depicts the percent cell number decreases for a mixture (S1) of SUN-M and SUN-D compared to the standards described previously using the Coulter Counter methodology.

This mixture named S1 was used to run an activity assay using the Coulter Counter methodology and these results can be compared to the control experiments described before (FIG. 21).

The mixture S1 is more active by 7–10-fold than complex 2 but not as active as cisplatin. The fact that these complexes are more potent than complex 2 is a very promising result and the goal at this point is to show that the selectivity of these compounds is greater than cisplatin. The selectivity of these complexes was investigated by coupling a 'mutated' peptide, AGR—NH$_2$ to complex 2. The mono- and di-substituted complex was termed SAN-M and SAN-D, respectively.

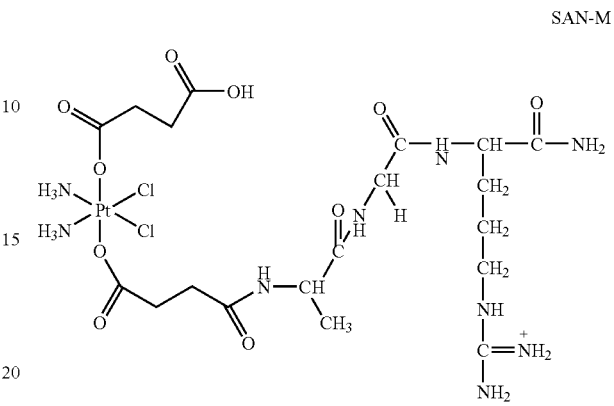

SAN-M

Figure 22:
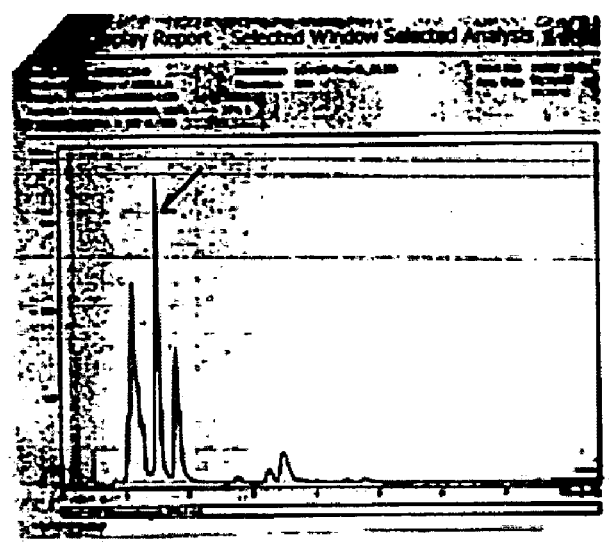
FIG. 22 depicts the LC-MS spectrum for mono-substituted adduct SAN-M.
Figure 23:
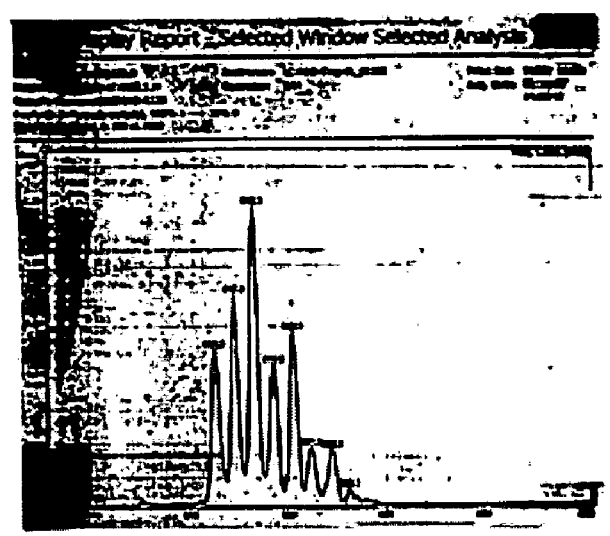
FIG. 23 depicts the LC-MS spectrum for mono-substituted adduct SAN-M.

The coupling reaction was performed as shown in Scheme 4 and analyzed by LC-MS. The only platinum complex obtained in this reaction at retention time of 1.5 minutes was the mono substituted compound (FIGS. 22 and 23). The observed m/z of 818.3 matches the calculated of 818.54.

The separation of the desired product from the impurities was successful on an analytical column (FIG. 22) but was found to be challenging in either a semi-preparative or preparative columns. This is still being pursued at this moment.

Another approach taken to investigate the selectivity of these compounds was by the labeling of NGR—NH$_2$, RGD—NH$_2$ and the 'mutated' peptides AGR—NH$_2$, ARA—NH$_2$ with biotin. The latter sequence was the one chosen by Ellerby et al to show internalization of CNGRC-GG-(pro-apoptotic peptide) (SEQ ID NO: 3) into KS1767 cells derived from Kaposi Sarcoma.

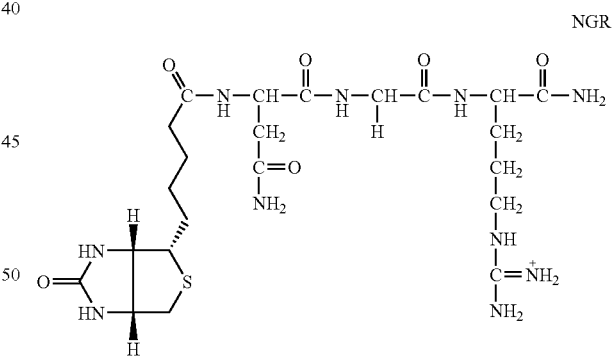

NGR

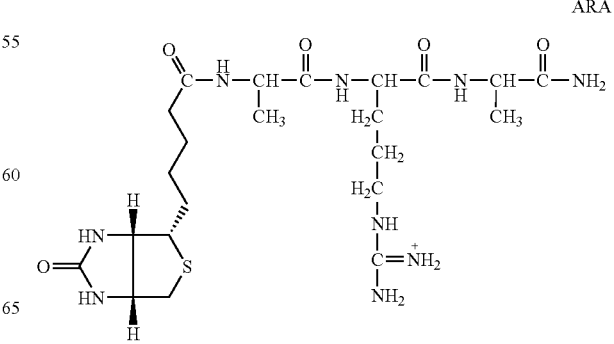

ARA

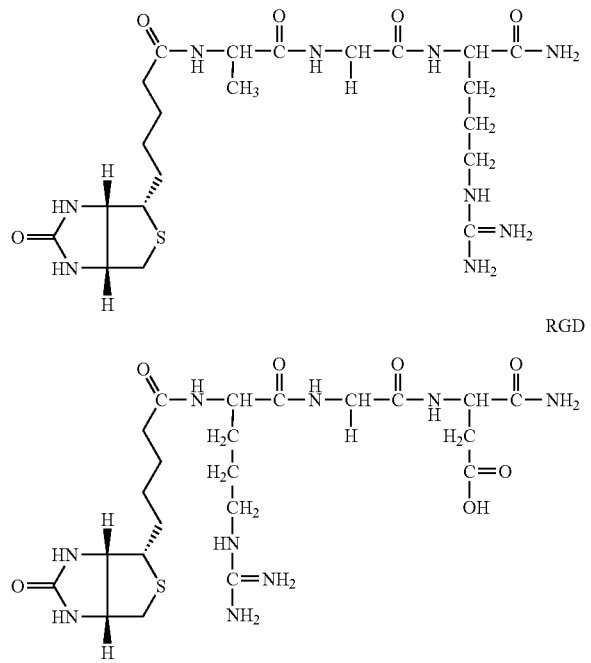

The interaction of biotin with streptavidin-FITC (FITC=fluorescein isothiocyanate) will be used as a probe for internalization. Streptavidin-FITC is known to contain 4–8 moles of (FITC) per mol of streptavidin thus amplifying the fluorescence signal compared to an approach in which only one fluorescein molecule is attached to the peptide. The four biotin labeled compounds were synthesized in the peptide synthesizer and analyzed by LC-MS. The large-scale purification of the labeled peptides is underway.

Dosages

The dosage of any compound of the present invention will vary depending on the symptoms, age and body weight of the patient, the nature and severity of the disorder to be treated or prevented, the route of administration, and the form of the supplement. Any of the subject formulations may be administered in a single dose or in divided doses. Dosages for the compounds of the present invention may be readily determined by techniques known to those of skill in the art or as taught herein. Also, the present invention contemplates mixtures of more than one subject compound, as well as other therapeutic agents. Further, the present invention contemplates administration of the therapeutic agent that is contained in a subject coordination complex (or a related agent) in conjunction with the complex itself to increase the ratio of the therapeutic agent to the coordination complex formed upon release of the therapeutic agent, In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible affects on the timing of administration of the formulation, may need to be identified for any particular compound of the present invention. This may be accomplished by routine experiment as described herein, using one or more groups of animals (preferably at least 5 animals per group), or in human trials if appropriate. The effectiveness of any compound and method of treatment or prevention may be assessed by administering the supplement and assessing the effect of the administration by measuring one or more indices associated with the neoplasm of interest, and comparing the post-treatment values of these indices to the values of the same indices prior to treatment.

The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. Treatment, including supplement, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments to the amount(s) of agent administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The combined use of several compounds of the present invention, or alternatively other chemotherapeutic agents, may reduce the required dosage for any individual component because the onset and duration of effect of the different components may be complimentary. In such combined therapy, the different active agents may be delivered together or separately, and simultaneously or at different times within the day.

Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. Although compounds that exhibit toxic side effects may be used, care should be taken to design a delivery system that targets the compounds to the desired site in order to reduce side effects.

The data obtained from the cell culture assays and animal studies may be used in formulating a range of dosage for use in humans. The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For agents of the present invention, the therapeutically effective dose may be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

Formulation

The compounds of the present invention may be administered by various means, depending on their intended use, as is well known in the art. For example, if compounds of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compounds of the present invention may be formulated as eyedrops or eye ointments. These formulations may be prepared by conventional means, and, if desired, the compounds may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compounds may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of agent that may be combined with a carrier material to produce a single dose vary depending upon the subject being treated, and the particular mode of administration.

Methods of preparing these formulations include the step of bringing into association agents of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a compound thereof as an active ingredient. Compounds of the present invention may also be administered as a bolus, electuary, or paste.

In solid dosage forms for oral administration (capsules, tablets, pills, dragees, powders, granules and the like), the coordination complex thereof is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the supplement or components thereof moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the compound, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a coordination complex of the present invention with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a supplement or component includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required. For transdermal administration of transition metal complexes, the complexes may include lipophilic and hydrophilic groups to achieve the desired water solubility and transport properties.

The ointments, pastes, creams and gels may contain, in addition to a supplement or components thereof, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a supplement or components thereof, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compound.

Ordinarily, an aqueous aerosol is made by formulating an aqueous solution or suspension of the compound together with conventional pharmaceutically acceptable carriers and stabilizers. The carriers and stabilizers vary with the requirements of the particular compound, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise one or more components of a supplement in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

Kits

This invention also provides kits for conveniently and effectively implementing the methods of this invention. Such kits comprise any of the compounds of the present invention or a combination thereof, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

Exemplification

EXAMPLE 1

Synthesis of cis, cis, trans-$(NH_3)_2Pt(OH)_2Cl_2$ To a 0.57 g (1.89 mmol) portion of cisplatin was added 20.3 mL 30% $H_2O_2$ (v/v). The obtained brownish slurry was stirred for 2 hours at 55° C. then cool down to −10° C. for one hour. The obtained brownish solid filtered out and dried in the lypholizer overnight. Yield=58.4% (369 mg). I.R. (KBr): 3514 $cm^{-1}$.

EXAMPLE 2

Synthesis of cis, cis, trans-Diamminedichlorodisuccinato-platinum(IV) (2) Succinic anhydride (4.1 g, 41 mmol) and cis, cis, trans-diamminedichlorodihydroxyplatinum(IV) (3.3 g, 10 mmol) were dissolved in 5 mL of DMSO. The solution was heated to 70° C. for 15 h with constant stirring, cooled to room temperature, filtered, and the DMSO was removed from the filtrate by lyophilization to yield a yellow solid. Recrystallization from acetone at −20° C. afforded a pale yellow powder (3.7 g, 6.9 mmol, 69% yield). $^1$H NMR ($d_6$-acetone, 300 MHz): δ 2.45 (m, 4H, $CH_2$), 2.53 (m, 4H, $CH_2$), 6.511 (broad singlet, 6H, $NH_3$). $^{195}$Pt NMR: δ($^{195}$Pt) 1226.531 ppm. ESI-MS: [M+H]=534.0004 amu (calculated); 534.0001 amu (observed).

EXAMPLE 3

Synthesis of 3-tert-butoxycarbonylaminopropionic acid (L2). Triethylamine (6.2 mL, 45 mmol) was added to a solution of 3-aminopropionic acid (2.67 g, 30.0 mmol) in 50% aqueous dioxane (30 mL). BOC-ON (8.15 g, 33.1 mmol) was added and the reaction stirred for 3 h at room temperature. The reaction solution was diluted with $H_2O$ (40 mL) and ethyl acetate (60 mL). The aqueous layer was isolated, washed with ethyl acetate, and acidified with a 5% citric acid solution. The aqueous layer was subsequently extracted with ethyl acetate. The organic fractions were combined and evaporated to yield L2 as a cream solid (3.64 g, 62.8%). $^1$H NMR ($d_6$-DMSO, 300 MHz): δ 1.35 (s, 9H, $CH_3$), 2.33 (t, 2H, $CH_2$), 3.11 (q, 2H, $CH_2$), 6.67 (t, 1H, NH).

EXAMPLE 4

Synthesis of 4-tert-butoxycarbonylaminobutyric acid (L3). Prepared as described for L2 from stirring 4-aminobutyric acid (3.94 g, 38.2 mmol) in 50% aqueous dioxane with triethylamine (8.0 mL, 57 mmol) and BOC-ON (10.4 g, 42.2 mmol). A yellow oil was obtained that solidified upon addition of hexanes and cooling to −20° C. to yield a cream solid (4.03 g, 51.8%). $^1$H NMR ($d_6$-DMSO, 300 MHz): δ 1.36 (s, 9H, $CH_3$), 1.57 (m, 2H, $CH_2$), 2.17 (t, 2H, $CH_2$), 2.90 (m, 2H, $CH_2$), 6.80 (t, 1H, NH).

EXAMPLE 5

Synthesis of 5-tert-butoxycarbonylpentanoic acid (L4). Prepared as described for L3 from stirring 5-aminopentanoic acid (3.40 g, 29.1 mmol) in 50% aqueous dioxane with triethylamine (6.0 mL, 43.1 mmol) and BOC-ON (7.91 g, 32.1 mmol) to yield a cream solid (3.10 g, 48.8%).

$^1$H NMR (d$_6$-DMSO, 300 MHz): δ 1.36 (s, 9H, CH$_3$), 1.43 (m, 4H, 2CH$_2$), 2.17 (t, 2H, CH$_2$), 2.88 (m, 2H, CH$_2$), 6.73 (t, 1H, NH).

EXAMPLE 6

Synthesis of 6-tert-butoxycarbonylamimnohexanoic acid (L5). Prepared as described for L3 from stirring 6-amino-hexanoic acid (3.49 g, 26.7 mmol) in 50% aqueous dioxane with triethylamine (5.5 mL, 39.5 mmol) and BOC-ON (7.45 g, 30.2 mmol) to yield a pale yellow solid (2.96 g, 48.1%). $^1$H NMR (d$_6$-DMSO, 300 MHz): δ 1.2 (m, 2H, CH$_2$), 1.3 (m, 2H, CH$_2$), 1.36 (s, 9H, CH$_3$), 1.46 (m, 2H, CH$_2$), 2.16 (t, 2H, CH$_2$), 2.87 (m, 2H, CH$_2$), 6.74 (t, 1H, NH).

EXAMPLE 7

Synthesis of 17-(aminoacetoxy)-estradiol-3-benzoate (EL1). Diisopropylcarbodiimide (3.72 mL, 23.9 mmol) was added to a solution of N-tert-butoxycarbonyl-glycine (4.23 g, 24.2 mmol) and 4-dimethylaminopyridine (2.97 g, 24.3 mmol) in THF (200 mL). The solution was allowed to stir for 10 minutes before the addition of estradiol-3-benzoate (5.0 g, 13 mmol). After being stirred overnight, the solution was filtered and the solvent was removed by rotary evaporation. The residue obtained was redissolved in a 1M HCl/dioxane solution (265 mL) and stirred for an additional 6 h. Following evaporation of dioxane, the residue was resuspended in 100 mL H$_2$O and the pH was adjusted with ammonium hydroxide to 10. The solution was stirred for several hours and filtered to collect a white solid (4.32 g, 75.0%). $^1$H NMR (d$_6$-DMSO, 300 MHz): δ 8.118 (d, 2H, ArH), 7.742 (t, 1H, ArH), 7.599 (t, 2H, ArH), 7.34 (d, 1H, ArH), 7.01 (d, 1H, ArH), 6.963 (s, 1H, ArH), 4.655 (t, 1H, CH), 3.829 (d, 1H, CH), 2.832 (m, 2H, CH), 1.75 (broad singlet, 2H, NH$_2$); 2.3–1.2 (m, 13H, CH), 0.796 (s, 3H, CH$_3$). ESI-MS [M+H]$^+$: 434.2326 amu (calculated); 434.2342 amu (observed).

EXAMPLE 8

Synthesis of 17-(3-aminopropionate)-estradiol-3-benzoate (EL2). A solution of L2 (2.07 g, 10.9 mmol) and 4-DMAP (1.34 g, 10.9 mmol) was prepared in 100 mL DMF. Diisopropylcarbodiimide (1.7 mL, 11 mmol) was added and the solution was stirred for 10 minutes. Estradiol-3-benzoate (2.59 g, 6.88 mmol) was added and the reaction was allowed to stir for 7 h. The solution was filtered, diluted with water, and extracted with ether. The organic fractions were combined and evaporated to dryness to yield a pink residue. The residue was dissolved in 800 mL of methylene chloride; 120 mL TFA was added and the solution stirred for 2 h. The methylene chloride was evaporated to yield a pink oil, which was dissolved in H$_2$O and the pH adjusted to 10 with ammonium hydroxide. A white solid began to precipitate and the slurry was stirred for an additional hour. The solution was filtered to collect a white solid (~3 g crude). $^1$H NMR (d$_6$-DMSO, 300 MHz): δ 8.085 (d, 2H, ArH), 7.73 (t, 1H, ArH), 7.58 (t, 2H, ArH), 7.32 (d, 1H, ArH), 7.0 (d, 1H, ArH), 6.94 (s, 1H, ArH), 4.67 (t, 1H, CH), 3.04 (t, 2H, CH$_2$), 2.83 (m, 2H, CH), 2.68 (m, 2H, CH$_2$), 2.3–1.2 (m, 11H, CH), 1.7 (bs, 2H, NH$_2$) 0.814 (s, 3H, CH$_3$). ESI-MS [M+H]$^+$: 448.25 amu (calculated); 448.25 (observed).

EXAMPLE 9

Synthesis of 17-(4-aminobutanoate)-estradiol-3-benzoate (EL3). Prepared as described for EL2 using L3 (1.81 g, 8.92 mmol), 4-DMAP (1.11 g, 9.07 mmol), diisopropylcarbodi-imide (1.4 mL, 8.9 mmol), and estradiol-3-benzoate (2.15 g, 5.71 mmol). The BOC-protecting group was removed by stirring in 200 mL methylene chloride and 100 mL TFA. A white solid was isolated (2.56 g crude) and used without purification. $^1$H NMR (d$_6$-DMSO, 300 MHz): δ 8.09 (d, 2H, ArH), 7.73 (t, 1H, ArH), 7.59 (t, 2H, ArH), 7.33 (d, 1H, ArH), 7.0 (d, 1H, ArH), 6.95 (s, 1H, ArH), 4.65 (t, 1H, CH), 2.83 (m, 3H, CH/CH$_2$), 2.44 (t, 2H, CH$_2$), 2.4–2.0 (m, 4 H, CH$_2$) 1.81 (m, 4H, CH$_2$) 1.6–1.2 (m, 8H, CH), 1.7 (bs, 2H, NH$_2$) 0.813 (s, 3H, CH$_3$). ESI-MS [M+H]$^{30}$ : 462.26 amu (calculated); 462.26 (observed).

EXAMPLE 10

Synthesis of 17-(5-aminopentanoate)-estradiol-3-benzoate (EL4). Prepared as described for EL2 using L4 (1.26 g, 6.60 mmol), 4-DMAP (0.815 g, 6.67 mmol), diisopropylcarbodiimide (1.0 mL, 6.4 mmol), and estradiol-3-benzoate (1.55 g, 4.13 mmol). Deprotection of the amine was carried out by stirring in 480 mL methylene chloride and 72 mL TFA. A white solid was isolated (1.89 g crude). $^1$H NMR (d$_6$-DMSO, 300 MHz): δ 8.09 (d, 2H, ArH), 7.73 (t, 1H, ArH), 7.59 (t, 2H, ArH), 7.32 (d, 1H, ArH), 7.0 (d, 1H, ArH), 6.95 (s, 1H, ArH), 4.65 (t, 1H, CH), 2.83 (m, 3H, CH/CH$_2$), 2.36 (m, 3H, CH/CH$_2$), 2.3–2.0 (m, 3H, CH), 1.9–1.72 (m, 4H, CH) 1.7 (bs, 2H, NH$_2$), 1.57 (m, 4H, CH$_2$), 1.42–1.2 (m, 6H, CH), 0.815 (s, 3H, CH$_3$). ESI-MS [M+H]$^+$: 476.28 amu (calculated); 476.28 (observed).

EXAMPLE 11

Synthesis of 17-(6-aminohexanoate)-estradiol-3-benzoate (EL5). Prepared as described for EL2 using L5 (1.06 g, 4.57 mmol), 4-DMAP (0.582 g, 4.76 mmol), diisopropylcarbo-diimide (725 μL, 4.65 mmol), and estradiol-3-benzoate (0.511 g, 1.36 mmol). Removal of the BOC-group was achieved by stirring in a solution of TFA (25 mL) in methylene chloride (240 mL). A white solid was isolated by filtration (~0.6 g crude). $^1$H NMR (d$_6$-DMSO, 300 MHz): δ 8.08 (d, 2H, ArH), 7.72 (t, 1H, ArH), 7.58 (t, 2H, ArH), 7.32 (d, 1H, ArH), 7.0 (d, 1H, ArH), 6.93 (s, 1H, ArH), 4.62 (t, 1H, CH), 2.82 (m, 1H, CH), 2.77 (m, 4H, CH$_2$), 2.31 (t, 2H, CH$_2$), 2.23–1.7 (m, 6H, CH), 1.7 (bs, 2H, NH$_2$), 1.57 (m, 4H, CH$_2$), 1.42–1.2 (m, 8H, CH), 0.798 (s, 3H, CH$_3$). ESI-MS [M+H]$^+$: 490.29 amu (calculated); 490.29 (observed).

EXAMPLE 12

Synthesis of cis, cis, trans-diamminedichloro-bis-(17-(N-carbonylmethylsuccinato)-estradiol-3-benzoate)platinum (IV) (BEP1). Diisopropylcarbodiimide (0.57 mL, 3.7 mmol) was added to a solution of 1 (0.81 g, 1.5 mmol) and 4-DMAP (0.48 g, 3.9 mmol) in DMF (100 mL). The solution was allowed to stir for 10 min at room temperature before the addition of EL1 (1.6 g, 3.7 mmol). The solution was stirred for 15 h at room temperature, filtered, and the filtrate was diluted with 200 mL of ether. The resultant solution was cooled at −20° C. for 10 h to facilitate precipitation. The crude product was filtered, redissolved in 90:10 MeCN:H$_2$O, and purified by normal phase column chromatography (90: 10 MeCN: H$_2$O) to yield a pale yellow solid (0.72 g, 35%).

¹H NMR (d₆-DMSO, 300 MHz): δ 8.325 ppm (t, 2H, NH), 8.103 ppm (d, 4H, ArH), 7.736 ppm (t, 2H, ArH), 7.592 ppm (t, 4H, ArH), 7.34 ppm (d, 2H, ArH), 7.01 ppm (d, 2H, ArH), 6.945 ppm (s, 2H, ArH), 6.559 ppm (bs, 6H, NH₃), 4.649 ppm (t, 2H, CH), 3.829 ppm (d, 2H, CH₂), 2.832 ppm (m, 4H, CH), 2.6–1.2 ppm (m, 36H, CH), 0.785 ppm (s, 6H, CH₃). ESI-MS [M+H]⁺: 1364.4299 amu (calculated); 1364.4253 amu (observed).

EXAMPLE 13

Synthesis of cis, cis, trans-diamminedichloro-bis-(17-(N-(2-carboxy-ethyl)-succinato)-estradiol-3-benzoate)platinum (IV) (BEP2). Prepared as described for BEP1 using 1 (0.366 g, 0.685 mmol), 4-DMAP (0.356 g, 2.91 mmol), diisopropylcarbodiimide (427 µL, 2.74 mmol), and EL2 (1.24 g, 2.78 mmol). Crude BEP2 was purified by flash chromatography (90:10 acetonitrile:water) to yield a pale yellow solid (0.133 g, 14%). ¹H NMR (d₆-DMSO, 300 MHz): δ 8.10 (d, 4H, ArH), 7.95 (t, 2H, NH), 7.74 (t, 2H, ArH) 7.60 (t, 4H, ArH), 7.35 (d, 2H, ArH), 7.0 (d, 2H, ArH), 6.95 (s, 2H, ArH), 6.49 (bs, 6H, NH₃), 4.65 (t, 2H, CH), 3.26 (t, 4H, CH₂), 2.83 (m, 4H, CH), 2.47 (m, 4H, CH₂), 2.28 (t, 4H, CH₂), 1.83 (t, 4H, CH₂), 1.6–1.2 (m, 26H, CH), 0.799 (s, 6H, CH₃).

EXAMPLE 14

Synthesis of cis, cis, trans-diamminedichloro-bis-(17-(N-(3-carboxy-propyl)-succinato)-estradiol-3-benzoate)platinum(IV) (BEP3). Prepared as described for BEP1 using 1 (0.652 g, 1.22 mmol), 4-DMAP (0.612 g, 5.01 mmol), diisopropylcarbodiimide (760 µL, 4.88 mmol), and EL3 (2.29 g, 4.97 mmol). Crude material was purified by flash chromatography (90: 10 acetonitrile:water) to yield a pale yellow solid (0.124 g, 7%). ¹H NMR (d₆-DMSO, 300 MHz): δ 8.1 (d, 4H, ArH), 7.85 (t, 2H, NH), 7.74 (t, 2H, ArH) 7.59 (t, 4H, ArH), 7.35 (d, 2H, ArH), 7.0 (d, 2H, ArH), 6.96 (s, 2H, ArH), 6.50 (bs, 6H, NH₃), 4.69 (t, 2H, CH), 3.26 (t, 4H, CH₂), 2.83 (m, 4H, CH), 2.47 (m, 4H, CH₂), 2.4–2.24 (m, 12H, CH₂), 1.83 (t, 4H, CH₂), 1.6–1.2 (m, 22H, CH), 0.805 (s, 6H, CH₃).

EXAMPLE 15

Synthesis of cis, cis, trans-diamminedichloro-bis-(17-(N-(4-carboxy-butyl)-succinato)-estradiol-3-benzoate)platinum (IV) (BEP4). Prepared as described for BEP1 using 1 (0.407 g, 0.762 mmol), 4-DMAP (0.367 g, 3.00 mmol), diisopropylcarbodiimide (466 µL, 2.99 mmol), and EL4 (1.42 g, 2.99 mmol). Crude material was purified by flash chromatography (90:10 acetonitrile:water) to yield a pale yellow solid (0.237 g, 21%). ¹H NMR (d₆-DMSO, 300 MHz): δ 8.10 (d, 4H, ArH), 7.85 (t, 2H, NH), 7.74 (t, 2H, ArH) 7.60 (t, 4H, ArH), 7.35 (d, 2H, ArH), 7.0 (d, 2H, ArH), 6.97 (s, 2H, ArH), 6.51 (bs, 6H, NH₃), 4.64 (t, 2H, CH), 3.01 (t, 4H, CH₂), 2.84 (m, 4H, CH), 2.43 (m, 4H, CH₂), 2.3–2.2 (m, 8H, CH₂), 2.2–1.2 (m, 32H, CH), 0.804 (s, 6H, CH₃).

EXAMPLE 16

Synthesis of cis, cis, trans-diamminedichloro-bis-(17-(N-(5-carboxy-pentyl)-succinato)-estradiol-3-benzoate)platinum(IV) (BEP5). Prepared as described for BEP1 using 1 (0.179 g, 0.336 mmol), 4-DMAP (0.232 g, 1.89 mmol), diisopropylcarbodiimide (258 µL, 1.65 mmol), and EL5 (0.809 g, 1.66 mmol). Crude product was purified by flash chromatography (90:10 acetonitrile:water) to yield a pale yellow solid (0.0958 g, 19%). ¹H NMR (d₆-DMSO, 300 MHz): δ 8.09 (d, 4H, ArH), 7.81 (t, 2H, NH), 7.71 (t, 2H, ArH) 7.57 (t, 4H, ArH), 7.32 (d, 2H, ArH), 6.98 (d, 2H, ArH), 6.94 (s, 2H, ArH), 6.49 (bs, 6H, NH₃), 4.62 (t, 2H, CH), 3.0 (t, 4H, CH₂), 2.82 (m, 4H, CH), 2.42 (m, 4H, CH₂), 2.3–2.2 (m, 12H, CH₂), 2.1–1.2 (m, 34H, CH), 0.799 (s, 6H, CH₃). ESI-MS [M+Na]: 1497.53 (calculated); 1497.59 (observed).

EXAMPLE 17

Cell Culture. MCF-7 and MDA-MB231 cells were grown in DMEM (GIBCO/BRL) containing 10% FBS (GIBCO/BRL) and 2 mM glutamine. HCC-1937 cells were grown in RPMI-1640 media (ATCC) containing 10% FBS. All cells were incubated at 37° C. under a 5% CO₂ atmosphere.

EXAMPLE 18

Upregulation of HMGB1 induced by BEP. MCF-7 cells were grown to 70% confluence on 12-mm glass coverslips in 24-well plates. The cells were treated with either estrogen or BEPn and incubated for 0–24 h. The cells were then permeabilized with 25% acetic acid in methanol for 10 min at RT, washed with PBS, and incubated with 1: 100 dilution of anti-HMGB1 polyclonal antibody (PharMingen) for 1 h at 37° C. The cells were subsequently incubated with a 1:50 dilution of goat anti-rabbit IgG conjugated to fluorescein (Biosource International, Camarillo, Calif.) for 1 h at 37° C. The coverslips were then placed on microscope slides, fixed with gelvatol, and incubated at 4° C. for 12 h. HMGB1 levels were then visualized under a fluorescent light microscope (Zeiss Axiophot).

EXAMPLE 19

Cytotoxic Profile of BEP. Cells were seeded onto 96-well plates at a density of 1000 cells per well and allowed to grow for 24 h. Cells were treated with BEP1-5 at the following concentrations: 1, 2, 3, 4, 5, 6, 8, 10 µM. The 96-well plates were covered with Breathe-Easy gas permeable membranes (Diversified Biotech) and the cells incubated at 37° C. for 5–7 days. After the incubation period, the cells were fixed by addition of 25 µL of 50% TCA and subsequent incubation at 4° C. for 30 min. The viable cells were then stained by addition of 100 µL of sulforhodamine B (SRB) in 0.1% acetic acid followed by incubation for 30 min at RT. The cells were washed with PBS and allowed to dry overnight. The SRB was solubilized by the addition of 100 µL of 10 mM Tris (pH 10.5) followed by shaking for 5 min. The number of viable cells were then quantified by measuring the absorbance at 492 nm.

EXAMPLE 20

Synthesis of NGRNH₂, RGDNH₂ AGRNH₂ and biotin-labeled peptides All the amino acids and reagents were automatically delivered unless stated otherwise. All amino acids and HOBt were purchased from NovaBiochem, DMF biosynthesis grade from VWR and piperidine, DIC, TFA, acetic anhydride, diisopropylethyl amine (DIPEA), Triisopropylsilane (TIPS) from Sigma-Aldrich. Table 4 below summarizes the amounts of Rink amide resin, amino acids (0.5 M) and reagents (0.5 M) used in the synthesis. The amino acids are dissolved in N-methyl pyrrilidinone (NMP) and all the other reagents in DMF. All peptides were synthesized in the laboratory automated 348Ω Advanced Chemtec instrument. The following procedure was used for all syntheses. For more details about the instrument and synthetic procedures see 348Ω Advanced Chemtec Manual. An easy to make computer program should be made each time in order to run a peptide synthesis. The main body of the computer program needs to be written only one time and minor changes are made as necessary for each specific synthesis run. In a one synthesis run several wells, up to 96, can be potentially used and in each well a different peptide can be made. One computer program will command all different wells by stating the specific amino acids to be delivered to each one of them. The amount of resin needed for the synthesis of each peptide is added manually to each one of the reaction block wells. In general 2–16 wells were used and a maximum total volume of 1.5 mL was added in every step to each of them. (A) The resin is washed three times with 1.5 mL of DMF, shaking each time the reaction block (rv block) for 5 minutes and then emptying the wells for 3 minutes under $N_2$ pressure. It is important to choose the section of the rv that needs to be emptied. The rv block is divided in four sections each one containing 24 wells: front, middle front, middle back and back. If only one section is used it is necessary to check under the rv block empty valve command only the section to be used. (B) This is followed by the three times deprotection of the Fmoc-protected Rink amide resin by 1.5 mL piperidine(20%)/DMF. Each time the reaction block (rv) is left to shake for 5 minutes and then emptying the wells for 3 minutes under $N_2$ pressure. The exact washing procedure (A) was then repeated. (C) This amino acid coupling step is repeated twice. 0.6 mL of the amino acid, 0.5 mL DIC and 0.5 mL HOBt are added to each well. The rv block shake for 1 hour and the wells emptied for 3 minutes. Step (A) is then repeated. (D) To avoid formation of undesirable peptides acetic anhydride and DIPEA are used to cap the remaining free amines by adding 0.75 mL of each reagent, shaking for 20 minutes and emptying for 5 minutes. This procedure is repeated but with only 5 minutes shaking followed by (A). (E) The resin-attached Fmoc-protected amino acid or peptide is deprotected by adding 1.5 mL 20% piperidine/DMF, shaking the rv block for 5 minutes and emptying for 3 minutes. This is repeated two additional times followed by (A). (F) Steps (C), (D) and (E) are repeated for all additional amino acids. (G) At the end of the synthesis the resin is washed with 3×2 mL MeOH and $CH_2Cl_2$ and dried overnight under air. (H) The cleavage of the peptide out of the resin is accomplished by adding manually to the resin a called 'cleavage cocktail' which contains TFA (95%)/Triisopropylsilane (TIPS, 2.5%)/$H_2O$ (2.5%). NovaBiochem Catalog, 2000, pg. 15. (I) The peptide is precipitated out of the cleavage cocktail solution by adding it to a 10-fold (v/v) cold ether solution. The precipitate is spin down in a centrifuge and the supernatant decanted. The obtained white solid is dissolved in 5 mL $H_2O$ or $H_2O$/ACN, lypholyzed andand purified by RP-HPLC.

TABLE 4

|  | NGR-/RGD-$NH_2$ | AGR$NH_2$ | Biotin-NGR$NH_2$ |
|---|---|---|---|
| Fmoc-Asn(Trt)OH | 6 mmol, 3.58 g | — | 3.5 mmol, 2.1 g |
| Fmoc-Arg(Pbf)O | 9 mmol, 5.84 g | 6 mmol, 3.89 g | 3.5 mmol, 2.3 g |
| Fmoc-Gly-OH | 9 mmol, 2.68 g | 6 mmol, 1.78 g | 3.5 mmol, 1.1 g |
| Fmoc-Ala-OH | — | 6 mmol, 1.87 g | — |
| Fmoc-Asp-OH | 3 mmol, 1.24 g | — | — |
| Biotin | — | — | 3.5 mmol, 0.9 g |
| Rink Amide | 0.046 mmol, 75 mg | 0.046 mmol, 75 mg | 0.05 mmol, 88 mg |
| DIC | 35 mmol, 5.5 mL | 20 mmol, 3.12 mL | 16 mmol, 2.5 mL |
| HOBt | 35 mmol, 4.73 g | 20 mmol, 2.7 g | 16 mmol, 2.2 g |
| $Ac_2O$ | 35 mmol, 2.11 mL | 20 mmol, 1.21 mL | 16 mmol, 1 mL |
| DIPEA | 35 mmol, 6.11 mL | 20 mmol, 3.50 mL | 16 mmol, 2.8 mL |

NGR$NH_2$ was purified by HPLC with a 250 mm semi-preparative C18 column, 100% $H_2O$ to 50% $H_2O$/ACN over 30 minutes. The desired products were collected at 4.8 and 6.4 minutes. RGD$NH_2$ was purified by HPLC with a 250 mm semi-preparative C18 column, 100% $H_2O$ to 50% $H_2O$/ACN over 40 minutes. The desired products were collected at 4.8 and 5.6 minutes. AGR$NH_2$ was purified by HPLC with a 250 mm semi-preparative and preparative C18 column, 95% $H_2O$/5% ACN to 50% $H_2O$/ACN over 30 minutes. The desired products were collected at 5.16 and 7.4 minutes for each column, respectively. Biotin-NGR$NH_2$, Biotin-AGR$NH_2$, Biotin-ARAN$NH_2$, Biotin-RGD$NH_2$ were purified by HPLC with a 100 mm analytical C18 column, 95% $H_2O$/5% ACN to 5% $H_2O$/95% ACN over 60 minutes. The desired products were all collected at 0.9 minutes.

EXAMPLE 21

Synthesis of $(NH_3)_2Pt(OCH_2CH_2CO\text{-}NGRNH_2)_nCl_2$ (n=1-2) To a 2.83 mg ($5.3\times10^{-3}$ mmol) portion of complex 2 in 200 μL DMF was added 10.16 mg EDC ($5.3\times10^{-2}$ mmol), 11.72 mg S—NHS ($5.3\times10^{-2}$ mmol) each in 50 μL $H_2O$. This mixture was protected from light, stirred for 2 hours at room temperature and then added to it 18.2 mg NGR$NH_2$ ($5.3\times10^{-2}$ mmol) in 200 μL $H_2O$ and the mixture stirred for 12 hours at r.t. The reaction was quenched by diluting 100 μL of the crude material in 400 μL $H_2O$ and purifying it in a preparative HPLC column using a 100% $H_2O$–75% $H_2O$ gradient over 25 minutes. The desired mono- and di-substituted products were collected at 15.55 and 15.95 minutes respectively. The platinum concentration was measured by atomic absorption.

EXAMPLE 22

Synthesis of $(NH_3)_2Pt(OCH_2CH_2CO\text{-}AGRNH_2)Cl_2$ To a 25.6 mg ($4.8\times10^{-2}$ mmol) portion of complex 2 in 200 μL DMF was added 46.0 mg EDC (0.24 mmol), 53 mg S—NHS (0.24 mmol) each in 100 μL $H_2O$. This mixture was protected from light, stirred for 2 hours at room temperature and then added to it 72.8 mg AGR$NH_2$ (0.24 mmol) in 200 μL $H_2O$ and the mixture stirred for 24 hours at r.t. The reaction was quenched by diluting 5 μL of the crude material in 90

μL H₂O and purifying it in a C18 analytical HPLC column using a 95% H₂O/5% ACN-5% H₂O/95% ACN gradient over 60 minutes. The desired mono-substituted product was collected at 1.5 minutes. Purification in a semi-preparative column by using a 100% H₂O–50% H₂O/ACN over 60 minutes afforded the product at 7.8 minutes. The platinum concentration was measured by atomic absorption.

EXAMPLE 23

Kill Curves on BCE cells The kill curves were performed on BCE cells. Growth conditions: DMEM+10% CS (Calf Serum), 3 ng/ml bFGF(basic fibroblast growth factor), 1% gps (glutamine penicillin streptamycin antibiotic. Plating Conditions: DMEM, 10% CS, 1% gps, 7,500 cells/well on a 48-well plate, plates are pre-coated with 1.5% gelatin in PBS so the cells plate better. Challenge: after 24 hours, change media to DMEM with 5% CS, 1% gps, add 10 nM–100 uM/well of platinated compound. The drug was re-suspended immediately before adjusting in PBS to a final concentration of 1 mM. 10-fold serial dilutions were prepared in PBS and added 10% volume per well and 2 ng/mL bFGF/well. After 72 hours the cells were counted on a Coulter Counter.

REFERENCES

All publications and patents mentioned herein, including those items listed below, are hereby incorporated by reference in their entirety as if each individual publication or patent was specifically and individually incorporated by reference. In case of conflict, the present application, including any definitions herein, will control.

Nature, 1965, 205, 698–699; Essays in Biochemistry, 1999, 34, 191–211; Chemical Reviews, 1999, 99, 2451–2466; Progress in Nucleic Acid Research and Molecular Biology, 2001, 67, 93–130; Pure and Applied Chemistry, 1987, 59, 181–192; Chemical Reviews, 1999, 99, 2467–2498; Proceedings of the National Academy of Sciences, 2002, 99, 4239–4244; Mutation Research, 2001, 478, 1–21; Journal of the American Chemical Society, 1996, 118, 12309–12321; Proceedings of the National Academy of Sciences USA, 1994, 91, 5672–5676; Proceedings of the National Academy of Sciences, 1994, 91, 10394–10398; Science, 1993, 261, 603–605; Proceedings of the National Academy of Sciences, 2000, 97, 5768–5772; Journal of Medicinal Chemistry, 2000, 43, 1409–1412; Journal of Inorganic Biochemistry, 1999, 77, 3–12; Inorganic Chemistry, 1996, 35, 3498–3503; J. Chem. Soc., Dalton Trans., 1999, 1209–1212; 1J. Chem. Soc., Dalton Trans., 1997, 2073–2077; Inorganic Chemistry, 2000, 39, 1728–1734; Inorganic Chemistry, 1995, 34, 1015–1021; Journal of Bioinorganic Chemistry, 2000, 5, 300–306; Inorganic Chimica Acta, 2002, 331, 98–108; Bioorganic and Medicinal Chemistry Letters, 1994, 4, 1375–1380; Endocrinology, 1989, 124, 318–324; Indian Journal of Chemistry, 1970, 8, 193–194. Folkman, J. in "Biologic Therapy of Cancer", Eds: DeVita, V.; Hellman, S.; Rosenberg, S. A., Lippincott Co., Philadelphia, 1991, 743. (b) Folkman, J. J. Natl. Cancer Inst. 1990, 82, 4; Folkman, J.; Shing, Y. J. Biol. Chem. 1992, 267(16), 10931; Rajotte, D.; Arap, W.; Hagedorn, M.; Koivunen, E.; Pasqualini, R.; Ruoslahti, E. J. Clin. Invest. 1998, 102(2), 430. (b) Pasqualini, R.; Ruoslahti, E. Nature 1996, 380, 364. (c) Trepel, M.; Arap, W.; Pasqualini, R. Gene Ther. 2000, 7, 2059; Ruoslahti, E. Nature Reviews Cancer 2002, 2, 83; Alberts, B.; Bray, D.; Lewis, J.; Raff, M.; Roberts, K.; Watson, J. "Molecular Biology of The Cell" 1994, 995, 3$^{rd}$ Ed.; Pasqualini, R.; Ruoslahti, E. Nature 1996, 380, 364; Koivunen, E.; Gay, D.; Ruoslahti, E. J. Biol. Chem. 1993, 268, 20205; Koivunen, E.; Wang, B.; Ruoslahti, E. Biotechnology 1995, 13, 265; Koivunen, E.; Wang, B.; Ruoslahti, E. J. Cell Biology 1994, 124(3), 373. (b) Healy, J. M.; Murayama, O.; Maeda, T.; Yoshino, K.; Sekiguchi, K.; Kikuchi, M. Biochemistry 1995, 34, 3948s; Hammes, H. P.; Brownlee, M.; Jonczyk, A.; Sutter, A.; Preissner, K. T. Nat. Med. 1996, 2, 529; Hart, S. L.; Knight, A. M.; Harbottle, R. P.; Mistry, A.; Hunger, H-D.; Cutler, D. F.; Williamson, R.; Coutelle, C. J. Biol. Chem. 1994, 269(17), 12468; Arap, W.; Pasqualini, R.; Ruoslahti, E. Science 1998, 279, 377; Ellerby, H. M.; Arap, W.; Ellerby, L. M.; Kain, R.; Andrusiak, R.; Del R10, G.; Krajewsky, S.; Lombardo, C. R.; Rao, R.; Ruoslahti, E., Bredesen, D. E.; Pasqualini, R.; Nature Med. 1999, 5(9), 1032; Jamieson, E. R.; Lippard, S. J. Chem Rev. 1999, 99, 2467. (b) Cohen, S. M.; Lippard, S. J. L. Prog. Nucl. Acid Res.Mol. Biol. 2001, 67, 93. (c) Cisplatin-Chemistry and Biochemistry of a Leading Anticancer Drug, Ed: Lippert, B., Wiley-VCH, Weinheim, 1999; Kutikov, A. "Year End Report", 2001; NovaBiochem Catalogue, 2000, P15; Houston, P.; et al. FEBS Letters, 2001, 492, 73–77. U.S. Provisional Patent Application 60/439,729; and 60/505,088.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A compound comprising: (a) a platinum(IV) metal center (b) two cis labile ligands bonded to the platinum metal center, and (c) one or more therapeutic agents covalently attached to the platinum metal center directly or through a tether, wherein the therapeutic agent is a steroid and is not covalently attached to the platinum metal center through the cis labile ligands.

2. The compound of claim 1, wherein the compound further comprises two cis non-labile ligands bonded to the platinum metal center, and wherein the therapeutic agent is not covalently attached to the platinum metal center through the cis non-labile ligands.

3. The compound of claim 1, wherein the two cis labile ligands are halides.

4. The compound of claim 3, wherein the halides are chlorides.

5. The compound of claim 1, wherein the steroid is estrogen.

6. The compound of claim 1, wherein the therapeutic agent is covalently attached to the metal center through a tether.

7. The compound of claim 6, wherein the steroid is estrogen.

8. The compound of claim 1, wherein the compound has the following formula:

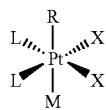

wherein:
X, independently for each occurrence, represents a labile covalently bonded ligand, or both of X taken together represent a bidentate ligand;
L, independently for each occurrence, represents a ligand bonded to the platinum metal center through a covalent bond, or both of L taken together represent a bidentate ligand;
M represents a therapeutic agent, a targeting moiety, or a labile covalently bonded ligand; and
R represents a steroid, wherein R and/or M is attached directly to the platinum metal center or through a tether.

9. The compound of claim 8, wherein M is a labile covalently bonded ligand and not a therapeutic agent or targeting moiety.

10. The compound of claim 8, wherein the compound is charged.

11. The compound of claim 8, wherein M is a therapeutic agent and is the same as R.

12. The compound of claim 8, wherein M is a therapeutic agent and is different than R.

13. The compound of claim 8, wherein X, independently for each occurrence, is selected from the group consisting of halide, —O-alkyl, —O-aryl, alkyl, and aryl.

14. The compound of claim 8, wherein both of X are Cl.

15. The compound of claim 8, wherein at least one L is $NH_3$.

16. The compound of claim 8, wherein both of X are Cl, both of L are $NH_3$, R is a tethered steroid wherein the steroid is estrogen, and the tether comprises an amide moiety.

17. The compound of claim 8, wherein both of X are Cl, both of L are $NH_3$, both R and M are tethered steroids wherein the steroids are estrogen, and the tethers comprise an amide moiety.

18. The compound of claim 8, wherein both of X are Cl, both of L are $NH_3$, both R and M are tethered steroids wherein one steroid is estrogen and the other steroid is not, and the tethers comprise an amide moiety.

19. The compound of claim 8, wherein both of X are Cl, both of L are $NH_3$, R is a tethered steroid wherein the steroid is estrogen, M is a tethered peptide comprising asparagine, glycine, and arginine, and the tethers comprise an amide moiety.

20. A compound comprising a platinum metal center, two cis labile ligands covalently bonded to the platinum metal center, two cis non-labile ligands covalently bonded to the platinum metal center, and at least one therapeutic agent covalently attached to the platinum metal center, wherein the therapeutic agent is a steroid attached directly to the platinum metal center or through a tether, and wherein upon reduction in the platinum metal center from a +4 oxidation state to a +2 oxidation state the therapeutic agent is released from the platinum metal center.

21. The compound of claim 20, wherein after release of the therapeutic agent from the platinum metal center, the compound comprising the platinum metal center is therapeutically effective.

22. A composition comprising a compound of any one of claims 1–4, 5, 6, 7, 8–12, 13–16, 17, 18–20, or 21 and a pharmaceutically effective excipient.

23. A kit comprising a compound of any one of claims 1–4, 5, 6, 7, 8–12, 13–16, 17, 18–20, or 21 and instructions for administering the compound to a patient.

* * * * *

SEQUENCE LISTING

<160> NUMBER OF SEQ ID NOS: 18

<210> SEQ ID NO 1
<211> LENGTH: 13
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 1

Cys Asn Gly Arg Cys Val Ser Gly Cys Ala Gly Arg Cys
 1               5                  10

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Asp Cys Arg Gly Asp Cys Phe Cys
 1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Asn Gly Arg Cys Gly Gly
 1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Met Ser Ile Ala Arg Leu
 1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Phe Gly Val
 1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Phe Gly Gly
 1
```

```
<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Phe Gly Gly Ser
 1

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Gly Gly Ser Val
 1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Phe Gly Gly Ser Trp
 1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Glu Arg Ile Ser
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Glu Arg Leu Ser
 1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 12

Gly Glu Arg Ala Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Pro Ser Gly Thr Ser
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Ser Gly Thr Gly
1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Ser Gly Thr
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Ser Gly Thr
1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Ser Gly Thr
1

<210> SEQ ID NO 18
<211> LENGTH: 13
<212> TYPE: PRT
```

```
-continued

<213> ORGANISM: Artificial Sequence
<220> FEATURE:
<223> OTHER INFORMATION: Description of Artificial Sequence: Synthetic
      peptide

<400> SEQUENCE: 18

Cys Gly Phe Glu Cys Val Arg Gln Cys Pro Glu Arg Cys
1               5                   10
```